US009593071B2

(12) United States Patent
Adamo

(10) Patent No.: US 9,593,071 B2
(45) Date of Patent: Mar. 14, 2017

(54) PROCESS FOR THE PREPARATION OF GAMMA AMINO ACIDS AND INTERMEDIATES USED IN SAID PROCESS

(71) Applicant: Royal College of Surgeons in Ireland, Dublin (IE)

(72) Inventor: Mauro Adamo, Dublin (IE)

(73) Assignee: Royal College of Surgeons In Ireland, Dublin (IE)

( * ) Notice: Subject to any disclaimer, the term of this patent is extended or adjusted under 35 U.S.C. 154(b) by 0 days.

(21) Appl. No.: 14/360,201

(22) PCT Filed: Nov. 22, 2012

(86) PCT No.: PCT/EP2012/073420

§ 371 (c)(1),
(2) Date: May 22, 2014

(87) PCT Pub. No.: WO2013/076225

PCT Pub. Date: May 30, 2013

(65) Prior Publication Data

US 2014/0336412 A1 Nov. 13, 2014

Related U.S. Application Data

(60) Provisional application No. 61/562,748, filed on Nov. 22, 2011, provisional application No. 61/683,605, filed on Aug. 15, 2012.

(30) Foreign Application Priority Data

Nov. 22, 2011 (EP) .................................... 11190187

(51) Int. Cl.

*C07C 227/32* (2006.01)
*C07C 227/02* (2006.01)
*C07C 227/04* (2006.01)
*C07D 261/14* (2006.01)
*C07D 453/04* (2006.01)
*C07D 401/06* (2006.01)

(52) U.S. Cl.

CPC .......... *C07C 227/32* (2013.01); *C07C 227/02* (2013.01); *C07C 227/04* (2013.01); *C07D 261/14* (2013.01); *C07D 401/06* (2013.01); *C07D 453/04* (2013.01); *C07B 2200/07* (2013.01); *C07C 2101/14* (2013.01)

(58) Field of Classification Search

None

See application file for complete search history.

(56) References Cited

PUBLICATIONS

Adamo, Mauro F.A., et al., "An improved synthesis of 3-methyl-4-nitro-5-(heteroarylethenyl)isoxazoles," *Heterocycles*, 71(5), pp. 1173-1181, (2007).

Baschieri, Andrea et al., "Catalytic Asymmetric Conjugate Addition of Nitroalkanes to 4-Nitro-5-styrylisoxazoles," *Angewandte Chemie*, International Edition, 48(49), pp. 9342-9345, (2009).

Chen, Ya Peng et al., "A thermal Wolff rearrangement-benzannulation route to naphtha[2,1-d]isoxazoles, [1]benzofuro[6,7-3]- or [5,4-d]isoxazoles and 1,2-benzisoxazoles," *Heterocycles*, 41(1), pp. 175-186, (1995).

Database CA [Online] Chemical Abstracts Service (citing Musante, Carlo, "Some .beta.-nitro derivatives of isoxazole. Reactions with hydrazine and aromatic aldehydes," 73 Gazzetta Chimica Italiana 355-365 (1943)).

Del Fiandra, Claudia et al., "Phase transfer catalyzed enantioselective cyclopropanation of4-nitro-5-styrylisoxazoles," *Chemical Communications* (Cambridge, UK), 48(32), pp. 3863-3865, (Feb. 24, 2012).

Felluga, F. et al., 19 *Tetrahedron: Asymm.* 945 (2008).

Gotoh Hiroaki et al., "Diphenylprolinol Silyl Ether as Catalyst of an Asymmetric, Catalytic, and Direct Michael Reaction of Nitroalkanes with .alpha.,.beta.-Unsaturated Aldehydes," *Organic Letters, American Chemical Society*, US, vol. 9, No. 25, pp. 5307-5309, (Jan. 1, 2007).

Krishnamurthy, A. et al., "Isoxazolyl sulfanilamides," *Indian Journal of Applied Chemistry*, 35, pp. 4-6), (1972).

Murty, A. Krishna et al., "Spectroscopic evidence for the formation of 5-styryl derivatives during condensation of 3, 5-dimethyl-4-nitroisoxazole with aldehydes," *Indian Journal of Chemistry*, 11(10), pp. 1074-1076, (1973).

Pei, Qing-Lan et al., "Catalytic Asymmetric 1,6-Michael Addition of Arylthiols to 3-Methyl-4-nitro-5-alkenyl-isoxazoles with Bifunctional Catalysts," *Journal of Organic Chemistry*, 76(19), pp. 7849-7859, (Aug. 30, 2011).

*Primary Examiner* — Fereydoun G Sajjadi
*Assistant Examiner* — Ana Z Muresan
(74) *Attorney, Agent, or Firm* — Brinks Gilson & Lione

(57) ABSTRACT

The invention relates to the preparation of gamma amino acids of formula (I) and pharmaceutically acceptable salts, solvates and prodrugs thereof, and to intermediates used for their preparation. (formula I) wherein $R^1$ is selected from an alkyl group, an alkenyl group, an alkynyl group and a cycloalkyl group, each of which may be optionally substituted and * denotes a chiral center. In particular, the present invention provides an efficient synthesis of (S)-pregabalin which is suitable for carrying out on an industrial scale.

(I)

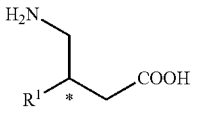

16 Claims, No Drawings

PROCESS FOR THE PREPARATION OF GAMMA AMINO ACIDS AND INTERMEDIATES USED IN SAID PROCESS

TECHNICAL FIELD

The present invention relates to the preparation of gamma amino acids, and pharmaceutically acceptable salts, solvates and prodrugs thereof.

In particular, the invention relates to an preparation of both (S)- and (R)-enantiomers of gamma amino acids. In particular, the invention relates to the preparation of (S)-pregabalin and pharmaceutically acceptable salts, solvates and prodrugs thereof. The invention further relates to intermediates used in said preparations, processes for their synthesis and use thereof to prepare gamma amino acids.

BACKGROUND (S)-pregabalin is an anticonvulsive drug which is also indicated in the treatment of generalised anxiety disorder (GAD) in adults, and the treatment of peripheral and central neuropathic pain in adults. Its chemical name is (3S)-3-(aminomethyl)-5-methylhexanoic acid or (S)-(+)-4-amino-3-(2-methylpropyl)butanoic acid, and it has the following chemical structure:

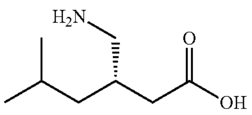

A synthesis of (S)-pregabalin is described by Hayashi et al. (Organic Letters, 2007, Vol. 9, No. 25, 5307-5309). The synthesis comprises conjugate addition of nitromethane to α,β-unsaturated aldehydes in the presence of a diphenylprolinol silyl ether catalyst to give an aliphatic nitro compound which undergoes oxidation followed by reduction to (S)-pregabalin (Scheme 1).

Scheme 1

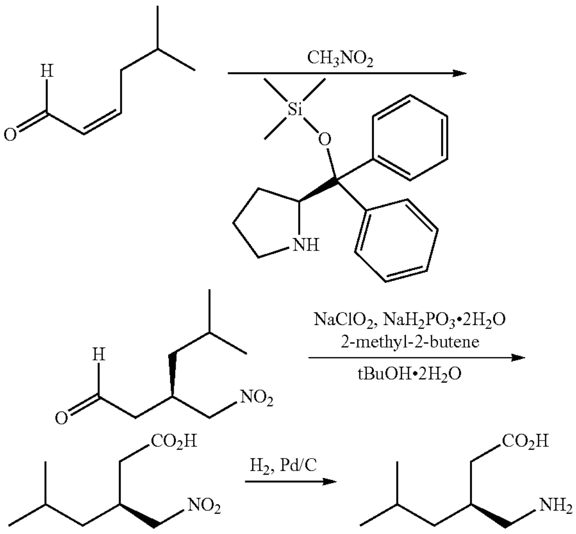

The catalyst is prepared in six steps. The scale up of the synthesis is difficult making it unsuitable for use on an industrial scale.

The present invention provides an efficient method for preparing gamma amino acids such as (S)-pregabalin, preferably in high enantiomeric purity.

SUMMARY OF THE INVENTION

One aspect of the invention relates to a process for the preparation of a compound of formula (I), and pharmaceutically acceptable salts, solvates and prodrugs thereof:

(I)

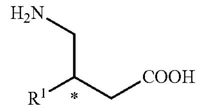

wherein:
$R^1$ is selected from an alkyl group, an alkenyl group, an alkynyl group and a cycloalkyl group, each of which may be optionally substituted; and * denotes a chiral centre;
which process comprises the step of reacting a compound of formula (IV) with nitromethane in the presence of a catalyst to provide a compound of formula (V);

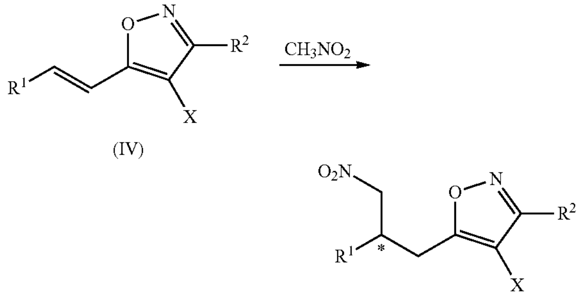

(IV)

(V)

wherein:
$R^1$ and * are as defined above in relation to the compound of formula (I); $R^2$ is an alkyl group or aryl group, each of which may be optionally substituted; and X is an electron withdrawing group.

A further aspect of the invention relates to a process for the preparation of a compound of formula (I), and pharmaceutically acceptable salts, solvates and prodrugs thereof (I)

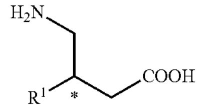

wherein:
$R^1$ is selected from an alkyl group, an alkenyl group, an alkynyl group and a cycloalkyl group, each of which may be optionally substituted; and * denotes a chiral centre;
which process comprises the step of preparing a compound of formula (IV) by reacting a compound of formula (III) with a compound of formula (II):

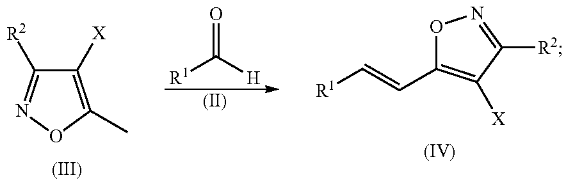

(III) (IV)

wherein:

$R^1$ is defined above in relation to the compound of formula (I); $R^2$ is an alkyl group or aryl group, each of which may be optionally substituted; and X is an electron withdrawing group.

A further aspect of the invention relates to a compound of formula (V), and salts, thereof,

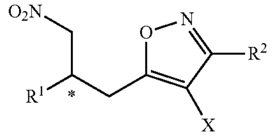

(V)

wherein:

$R^1$ is selected from an alkyl group, an alkenyl group, an alkynyl group and a cycloalkyl group, each of which may be optionally substituted; $R^2$ is an alkyl group or an aryl group, each of which may be optionally substituted; * denotes a chiral centre; and X is an electron withdrawing group.

A further aspect of the invention relates to a process for the preparation of a compound of formula (V), and salts thereof, which process comprises reacting a compound of formula (IV), with nitromethane in the presence of a catalyst:

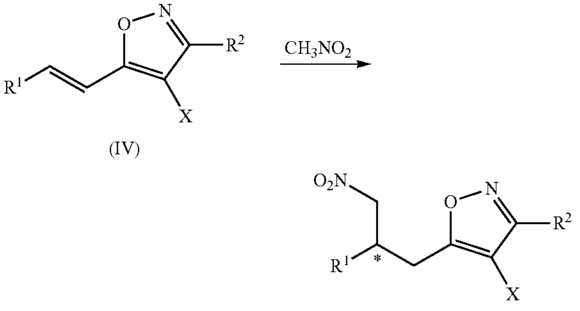

(IV) (V)

wherein:

$R^1$ is selected from an alkyl group, an alkenyl group, an alkynyl group and a cycloalkyl group, each of which may be optionally substituted; * denotes a chiral centre; $R^2$ is an alkyl group or aryl group, each of which may be optionally substituted; and X is an electron withdrawing group.

A further aspect of the invention relates to the use of a compound of formula (V):

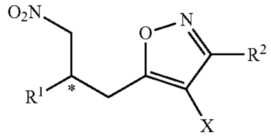

(V)

wherein:

$R^1$ is selected from an alkyl group, an alkenyl group, an alkynyl group and a cycloalkyl group, each of which may be optionally substituted; * denotes a chiral centre; $R^2$ is an alkyl group or aryl group, each of which may be optionally substituted; and X is an electron withdrawing group for the preparation of a compound of formula (I), in particular (S)-pregabalin.

A further aspect of the invention relates to a compound of formula (IV), or salt, thereof,

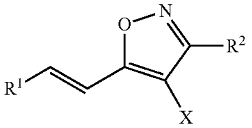

(IV)

wherein:

$R^1$ is selected from an alkyl group, an alkenyl group, an alkynyl group and a cycloalkyl group, each of which may be optionally substituted; $R^2$ is an alkyl group or aryl group, each of which may be optionally substituted; and X is an electron withdrawing group.

A further aspect of the invention relates to a process for the preparation of a compound of formula (IV), and salts thereof, which process comprises reacting a compound of formula (III) with a compound of formula (II):

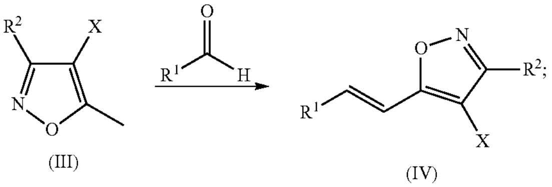

(III) (IV)

wherein:

$R^1$ is selected from an alkyl group, an alkenyl group, an alkynyl group and a cycloalkyl group, each of which may be optionally substituted; $R^2$ is an alkyl group or aryl group, each of which may be optionally substituted; and X is an electron withdrawing group.

A further aspect of the invention relates to the use of compound (IV):

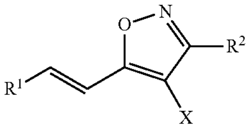

(IV)

wherein:

$R^1$ is selected from an alkyl group, an alkenyl group, an alkynyl group and a cycloalkyl group, each of which may be optionally substituted; $R^2$ is an alkyl group or aryl group, each of which may be optionally substituted; and X is an electron withdrawing group for the preparation of a compound of formula (I), in particular (S)-pregabalin.

A further aspect of the invention relates to a process for the preparation of a compound of formula (I), and pharmaceutically acceptable salts, solvates and prodrugs thereof:

(I)

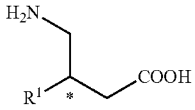

wherein:

$R^1$ is selected from an alkyl group, an alkenyl group, an alkynyl group and a cycloalkyl group, each of which may be optionally substituted; and * denotes a chiral centre;

which process comprises preparing a compound of formula (IV) by reacting a compound of formula (IIIA) with a compound of formula (II) to form a compound of formula (IIIB):

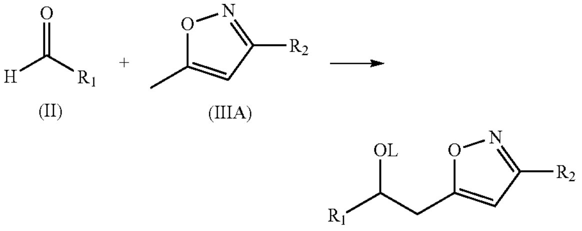

(II) (IIIA)

(IIIB)

wherein:

L is a hydroxyl activating group, $R^1$ is defined above in relation to the compound of formula (I); and $R^2$ is an alkyl group or aryl group, each of which may be optionally substituted; and converting the compound of formula (IIIB) to a compound of formula (IIIC):

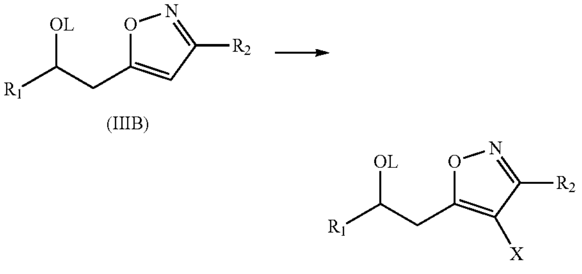

(IIIB)

(IIIC)

wherein:

X is an electron withdrawing group; and converting the compound of formula (IIIC) to a compound of formula (IV).

A further aspect of the invention relates to a process for the preparation of a compound of formula (IV), and salts thereof, which process comprises reacting a compound of formula (IIIA) with a compound of formula (II) to form a compound of formula (IIIB):

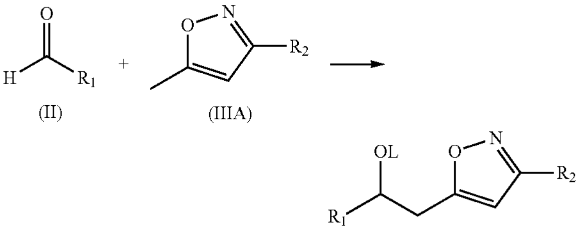

(II) (IIIA)

(IIIB)

wherein:

L is a hydroxyl activating group, $R^1$ is defined above in relation to the compound of formula (I);

and $R^2$ is an alkyl group or aryl group, each of which may be optionally substituted; and converting the compound of formula (IIIB) to a compound of formula (IIIC):

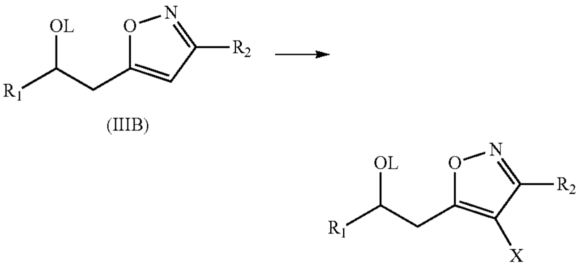

(IIIB)

(IIIC)

wherein:

X is an electron withdrawing group; and converting the compound of formula (IIIC) to a compound of formula (IV).

A further aspect of the present invention relates to a process for the preparation of a compound of formula (I), and pharmaceutically acceptable salts, solvates and prodrugs thereof:

(I)

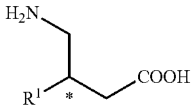

wherein:

$R^1$ is selected from an alkyl group, an alkenyl group, an alkynyl group and a cycloalkyl group, each of which may be optionally substituted; and * denotes a chiral centre;

which process comprises the step of reacting a compound of formula (IIA) with a compound of formula (III) in the presence of a catalyst to provide a compound of formula (V);

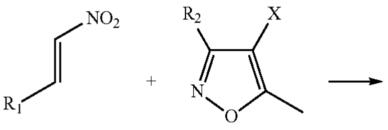

(IIA) (III)

-continued

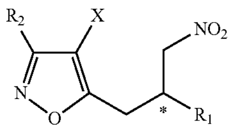

(V)

wherein:

$R^1$ and * are as defined above in relation to the compound of formula (I); $R^2$ is an alkyl group or aryl group, each of which may be optionally substituted; and X is an electron withdrawing group.

A further aspect of the present invention relates to a process for the preparation of a compound of formula (V), and salts thereof, which process comprises reacting a compound of formula (IIA) with a compound of formula (III) in the presence of a catalyst;

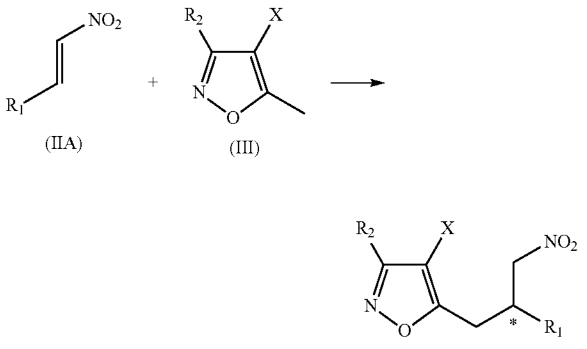

(IIA) (III)

(V)

wherein:

$R^1$ is selected from an alkyl group, an alkenyl group, an alkynyl group and a cycloalkyl group, each of which may be optionally substituted; $R^2$ is an alkyl group or aryl group, each of which may be optionally substituted; and X is an electron withdrawing group.

A further aspect relates to the compounds of formula (IIA), (IIIA), (IIIB) and (IIIC) as defined herein above and their use in the preparation of a compound of formula (I), in particular (S)-pregabalin.

A further aspect of the invention relates to the following compounds and their use as catalysts in chemical processes:

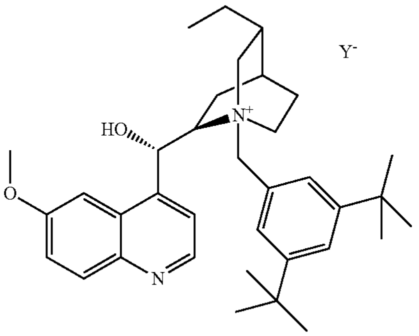

-continued

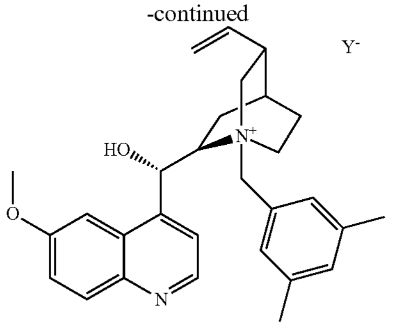

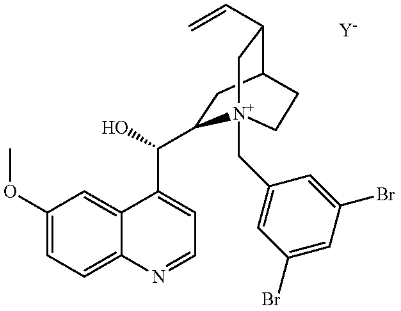

wherein $Y^-$ is a counterion. Examples of suitable counterions include fluoride, chloride, bromide and iodide. Preferably the counterion is bromide.

DETAILED DESCRIPTION

The present invention provides an efficient four step process for the preparation of gamma amino acids beginning from readily available starting materials (Schemes 2 and 3).

Scheme 2

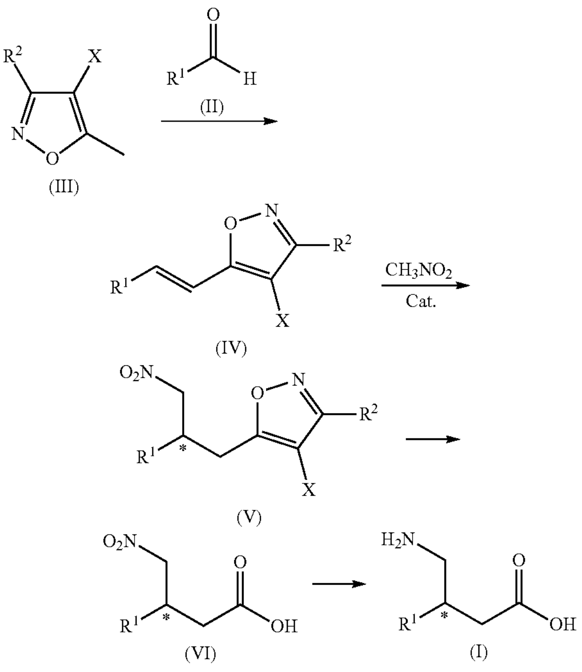

(III) (II) (IV) (V) (VI) (I)

wherein $R^1$, $R^2$ and X are as defined above.

Scheme 3

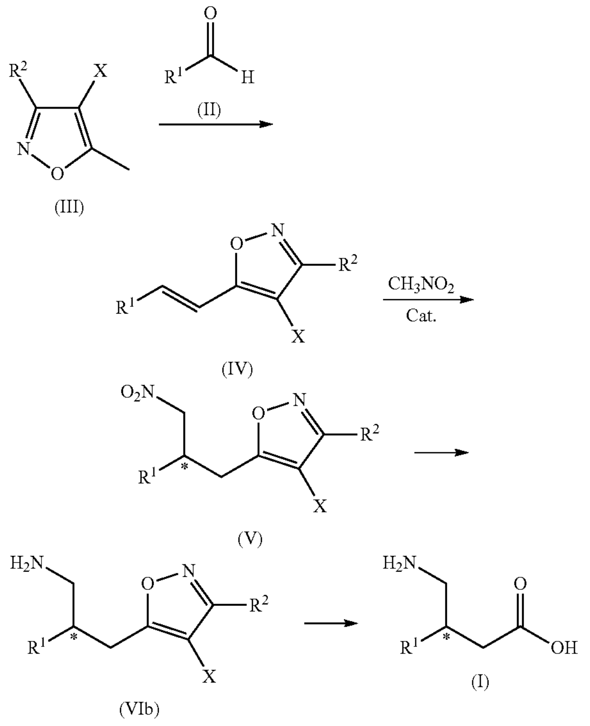

(II) (III) (IV) (V) (VIb) (I)

wherein $R^1$, $R^2$ and X are as defined above; with the proviso that X is not $NO_2$.

Surprisingly, aqueous solvent has been demonstrated to be suitable for the reaction of compounds of formula (II) with compounds of formula (III). The ability to use solvents comprising water as a reaction solvent is preferable on an industrial scale as it is reduces cost and reduces the need to handle harmful solvents. This is advantageous in terms of safety and is beneficial for the environment.

The chiral centre is introduced by addition of nitromethane to compounds of formula (IV) in the presence of a catalyst. This reaction may proceed in high yield and, if a chiral catalyst is used, may proceed with high enantioselectivity. Preferably the reaction does not require stoichiometric quantities of catalyst.

Preferably, the catalysts employed are cheap and commercially available, or can be easily synthesized.

Preferably the process for the preparation of gamma amino acids of the present invention does not require chromatographic purification of the intermediates. This is preferable for a synthesis which may be carried out on an industrial scale.

GENERAL DEFINITIONS

As used herein, the term "alkyl" includes both saturated straight chain and branched alkyl groups which may be substituted (mono- or poly-) or unsubstituted. Preferably, the alkyl group is a $C_{1-20}$ alkylgroup, more preferably a $C_{1-15}$, more preferably still a $C_{1-10}$alkyl group, more preferably still a $C_{1-8}$ alkyl group, more preferably still a $C_{1-6}$ alkyl group. Particularly preferred alkyl groups include, for example, methyl, ethyl, n-propyl, iso-propyl, n-butyl, sec-butyl, iso-butyl, tert-butyl, n-pentyl, n-hexyl, n-heptyl and n-octyl.

As used herein, the term "cycloalkyl" refers to a cyclic alkyl group which may be substituted (mono- or poly-) or unsubstituted.

As used herein, the term "alkenyl" refers to a carbon chain containing one or more carbon-carbon double bonds, which may be branched or unbranched, and substituted (mono- or poly-) or unsubstituted. Preferably the alkenyl group is a $C_{2-20}$ alkenyl group, more preferably a $C_{2-15}$ alkenyl group, more preferably still a $C_{2-10}$ alkenyl group, more preferably still a $C_{2-5}$ alkenyl group, or more preferably still a $C_{2-6}$ alkenyl group.

As used herein, the term "alkynyl" refers to a carbon chain containing one or more carbon-carbon triple bonds, which may be branched or unbranched, and substituted (mono- or poly-) or unsubstituted. Preferably the alkynyl group is a $C_{2-20}$ alkynyl group, more preferably a $C_{2-15}$ alkynyl group, more preferably still a $C_{2-10}$ alkynyl group, more preferably still a $C_{2-8}$ alkynyl group, or more preferably still a $C_{2-6}$ alkynyl group.

As used herein, the term "aryl" refers to a $C_{6-18}$ aromatic group which may be substituted (mono- or poly-) or unsubstituted. Preferably the aryl group is a $C_{6-14}$ aryl group, more preferably a $C_{6-10}$ aryl group. Typical examples include phenyl, naphthyl and anthracenyl.

The term "heteroaryl" refers to an aryl group as defined above which contains one or more heteroatoms. Suitable heteroatoms will be apparent to those skilled in the art and include, for example, sulphur, nitrogen, oxygen, phosphorus and silicon.

The term "alkoxy" refers to an O-alkyl group, wherein alkyl is as defined above. Preferably, the alkoxy group is a $C_{1-20}$ alkoxy group, more preferably a $C_{1-15}$ alkoxy group, more preferably still a $C_{1-10}$ alkoxy group, more preferably still a $C_{1-8}$ alkoxy group, more preferably still a $C_{1-6}$ alkoxy group. Particularly preferred alkoxy groups include, for example, methoxy, ethoxy, iso-propoxy, propoxy, butoxy, iso-butoxy, pentoxy and hexoxy.

The term "electron withdrawing group" refers to any group capable of withdrawing electrons away from a reaction centre. These groups may be electron withdrawing either by the inductive effect or the mesomeric effect. In one embodiment the electron withdrawing group is electron withdrawing via the inductive effect. In another embodiment the electron withdrawing group is electron withdrawing via the mesomeric effect. Examples of suitable electron withdrawing groups include halogens, nitriles, nitro groups, esters and sulfones. Preferably the electron withdrawing group is selected from halogens, $NO_2$, CN, $COOR^3$ and $SO_2R^3$; wherein each $R^3$ group is independently H or an optionally substituted alkyl group. More preferably the electron withdrawing group is selected from $NO_2$, CN, $COOR^3$ and $SO_2R^3$; wherein each $R^3$ group is independently H or an optionally substituted alkyl group. More preferably, X is CN or $NO_2$. More preferably, X is $NO_2$.

As used herein the term "hydroxyl activating group" refers to an alkyl sulfonyl or aryl sulfonyl compound. Suitable hydroxyl activating groups include compounds of formula R"—$SO_2$ where R" is an alkyl group or an aryl group. Suitable alkyl groups include $C_{1-6}$ alkyl optionally substituted with one or more, preferably 1-3, halogen atoms. Preferably the halogen is fluoro. Suitable aryl groups include phenyl optionally substituted with one or more, preferably 1-3, $C_{1-3}$ alkyl groups. Preferred alkyl and aryl sulfonyl compounds include methanesulfonyl, benzene sulfonyl, p-toluenesulfonyl and trifluoromethanesulfonyl.

Where a term defined above is described as substituted, examples of suitable substituents may include one or more of hydroxy, alkyl, aryl, halo, alkoxy, haloalkyl, haloalkoxy, amino, aminoalkyl, nitro and cycloalkyl.

It will be appreciated by those skilled in the art that the compounds of formula (I), (V), (VI) and (VIb) contain a chiral centre (denoted as *) and thus exist in the form a pair of optical isomers (i.e. enantiomers). Thus the compounds of formula (I), (V), (VI) and (VIb) may be either (S)-enantiomers or (R)-enantiomers or mixtures thereof including racemic mixtures.

Salts

The present invention relates to the preparation of all salts of the compounds described herein. The term "compound" is intended to include all such salts unless the context requires otherwise.

Acceptable salts of the compounds prepared herein include suitable acid addition or base salts thereof. A review of suitable pharmaceutical salts may be found in Berge et al., J. Pharm. Sci., 66, 1, 19 (1977). Salts are formed, for example with strong inorganic acids such as mineral acids, e.g. sulphuric acid, phosphoric acid or hydrohalic acids; with strong organic carboxylic acids, such as alkanecarboxylic acids of 1 to 4 carbon atoms which are unsubstituted or substituted (e.g., by halogen), such as acetic acid; with saturated or unsaturated dicarboxylic acids, for example oxalic, malonic, succinic, maleic, fumaric, phthalic or tetraphthalic; with hydroxycarboxylic acids, for example ascorbic, glycolic, lactic, malic, tartaric or citric acid; with aminoacids, for example aspartic or glutamic acid; with benzoic acid; or with organic sulfonic acids, such as ($C_1$-$C_4$)-alkyl- or aryl-sulfonic acids which are unsubstituted or substituted (for example, by a halogen) such as methane- or p-toluene sulfonic acid. Salts which are not pharmaceutically acceptable may still be valuable as intermediates.

Solvates

The present invention also includes the preparation of solvate forms, hydrated forms and anhydrous forms of the compounds of formula (I). The term "compound" is intended to include all such solvates unless the context requires otherwise.

Polymorphs

The invention furthermore encompasses the preparation of the compounds of formula (I) in their various polymorphic forms. It is well established within the pharmaceutical industry that chemical compounds may be isolated in any of such forms by slightly varying the method of purification and/or isolation from the solvents used in the synthetic preparation of such compounds. The term "compound" is intended to include all such polymorphs unless the context requires otherwise.

Prodrugs

The invention further includes the preparation of the compounds of formula (I) in prodrug form. Such prodrugs are generally compounds of formula (I) wherein one or more appropriate groups have been modified such that the modification may be reversed upon administration to a human or mammalian subject. Such reversion is usually performed by an enzyme naturally present in such subject, though it is possible for a second agent to be administered together with such a prodrug in order to perform the reversion in vivo. Examples of such modifications include esterification wherein the reversion may be carried out be an esterase etc. Other such systems will be well known to those skilled in the art. The term "compound" is intended to include all such prodrugs unless the context requires otherwise.

The Compounds of Formulae (I), (II), (IIA), (III), (IIIA), (IIIB), (IIIC), (IV), (V), (VI) and (VIb)

Throughout the specification, definitions of the substituents $R^1$, $R^2$ and X apply to each of compounds formulae (I), (II), (IIA), (III), (IIIA), (IIIB), (IIIC), (IV), (V), (VI) and (VIb) unless the context requires otherwise.

Throughout the specification, where substituents $R^1$, $R^2$ and $R^3$ are defined as optionally substituted, examples of suitable substituents may include one or more of hydroxy, alkyl, aryl, halo, alkoxy, haloalkyl, haloalkoxy, amino, aminoalkyl and cycloalkyl. Preferably, suitable substitutents are selected from one or more of hydroxy, alkyl, alkoxy, halo, haloalkoxy and aryl. More preferably, suitable substitutents are selected from one or more of hydroxy, methyl, ethyl, methoxy, ethoxy, halo, $CF_3$ and phenyl.

In one embodiment X is an electron withdrawing group. In another embodiment X is an electron withdrawing group selected from halogens, nitriles, nitro groups, esters and sulfones. In another embodiment X is an electron withdrawing group selected from halogens, $NO_2$, CN, $COOR^3$ and $SO_2R^3$; wherein each $R^3$ group is independently H or an optionally substituted alkyl.

In another embodiment X is an electron withdrawing group selected from $NO_2$, CN, $COOR^3$ and $SO_2R^3$; wherein each $R^3$ group is independently H or an optionally substituted alkyl. Preferably, X is CN or $NO_2$. More preferably, X is $NO_2$.

In one embodiment $R^1$ is selected from an alkyl group, an alkenyl group, an alkynyl group and a cycloalkyl group, each of which may be optionally substituted.

In one embodiment $R^2$ is selected from an alkyl group and a phenyl group, each of which may be optionally substituted.

Preferably, $R^1$ is an alkyl group, an alkynyl group or a cycloalkyl, each of which may be optionally substituted. More preferably $R^1$ is an optionally substituted alkyl group.

Preferably, $R^1$ and $R^2$ are independently selected $C_{1-20}$ alkyl groups, more preferably a $C_{1-15}$ alkyl groups, more preferably still a $C_{1-10}$ alkyl groups, more preferably still a $C_{1-8}$ alkyl groups, more preferably still a $C_{1-6}$ alkyl groups; which may optionally be substituted.

In one embodiment $R^1$ and $R^2$ are independently selected from methyl, ethyl, n-propyl, iso-propyl, n-butyl, sec-butyl, iso-butyl, tert-butyl, n-pentyl, n-hexyl, n-heptyl and n-octyl.

In one embodiment $R^1$ and $R^2$ are independently selected from methyl, ethyl, n-propyl, iso-propyl, n-butyl, sec-butyl, iso-butyl, tert-butyl.

In one embodiment $R^1$ is selected from methyl, ethyl, n-propyl, iso-propyl, n-butyl, sec-butyl, iso-butyl, tert-butyl, n-pentyl, n-hexyl, n-heptyl and n-octyl; and $R^2$ is methyl.

In one embodiment $R^1$ is selected from methyl, ethyl, n-propyl, n-butyl, iso-butyl, n-heptyl and n-octyl; and $R^2$ is methyl.

In a particularly preferred embodiment $R^1$ is iso-butyl and $R^2$ is methyl.

In a most preferred embodiment is $R^1$ iso-butyl, $R^2$ is methyl and X is $NO_2$.

The Catalyst

In one embodiment, the preparation of the compound of formula (V) is carried out in the presence of a catalyst.

In one embodiment the catalyst is a phase transfer catalyst. Examples of phase transfer catalysts include tetraalkylammonium salts such as tetrabutylammonium bromide and tetraethylammonium bromide; tetraarylammonium halides; arylalkylammonium halides such as triphenylbutylammonium bromide; trialkylarylphoshonium halides such as trimethylphenylphosphomium bromide; tetraalkylphosphonium halides such as tetrabutylphosphonium bromide; guanidinium salts; metal salen complexes; and crown ethers.

In one embodiment the catalyst is an organic amine for example a compound of formula $N(Rz)_3$, where Rz is independently selected from hydrogen and $C_{1-6}$ alkyl. Preferably, one and more preferably two and more preferably three of Rz are $C_{1-6}$ alkyl. Most preferably the amine is triethyl amine.

In one embodiment the catalyst is a chiral catalyst.

In one embodiment the chiral catalyst is a cinchona alkaloid derivative.

In one embodiment the cinchona alkaloid derivatives may include, but are not limited to, compounds of formula (VIIa) or (VIIb):

(VIIa)

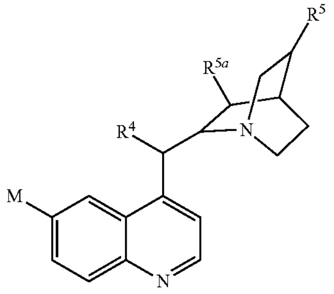

(VIIb)

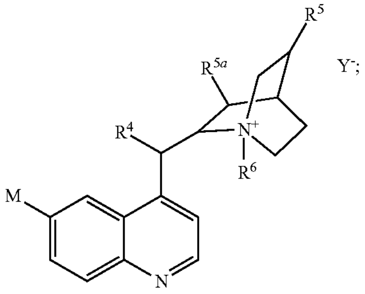

wherein, M is selected from H, hydroxy, alkoxy, O-alkenyl, $O(CH_2)_n$-aryl, $O(CH_2)_n$-heteroaryl, $O(CH_2)_n$-cycloalkyl, amino, $NR^{11}C(=O)R^{12}$, $C(=O)NR^{13}R^{14}$, $C(=O)R^{12}$, $O(C=O)R^{12}$, $C(=O)OR^{12}$, $NR^{11}SO_2R^{12}$, and $R^7$; in which each aryl, heteroaryl and cycloalkyl groups may be optionally substituted.

Preferably M is selected from H, hydroxy, alkoxy, O-alkenyl, $O(CH_2)_n$-aryl, $O(CH_2)_n$-heteroaryl, $O(CH_2)_n$-cycloalkyl and $R^7$, more preferably M is selected from H, hydroxy, alkoxy, O-alkenyl and $R^7$. Most preferably, M is selected from H, hydroxy and methoxy.

$R^4$ is selected from hydroxy, alkoxy, O-alkenyl, $O(CH_2)_n$-aryl, $O(CH_2)_n$-heteroaryl, $O(CH_2)_n$-cycloalkyl, amino, $NR^{11}C(=O)R^{12}$, $C(=O)NR^{13}R^{14}$, $C(=O)R^{12}$, $O(C=O)R^{12}$, $C(=O)OR^{12}$, $NR^{11}SO_2R^{12}$, and $R^7$; in which each aryl, heteroaryl and cycloalkyl groups may be optionally substituted.

Preferably $R^4$ is selected from hydroxy, alkoxy, O-alkenyl, optionally substituted $O(CH_2)_n$-aryl, amino, $NR^{11}SO_2R^{12}$, and $R^7$. More preferably, $R^4$ is selected from hydroxyl, alkoxy, O-alkenyl, $R^7$ and $O(CH_2)_n$-aryl optionally substituted with one or more of halo, $NO_2$, Me, $CF_3$ and OMe. Most preferably, $R^4$ is selected from hydroxy, O-benzyl, O-bis(trifluoromethyl)benzyl, O-2-nitro-4,5-dimethoxybenzyl and $R^7$.

$R^{11}$, $R^{12}$, $R^{13}$ and $R^{14}$ are independently selected from H, an alkyl group, an alkenyl group, an alkynyl group, an aryl group, a heteroaryl group and a cycloalkyl group, each of which may be optionally substituted; or $R^{13}$ and $R^{14}$ may together define an optionally substituted $C_3$-$C_{20}$ cycloalkyl group or $C_5$-$C_{15}$ heteroaryl group.

Preferably $R^{11}$ is selected from H and an alkyl group. More preferably, $R^{11}$ is selected from H, methyl and ethyl.

Preferably $R^{12}$, $R^{13}$ and $R^{14}$ are independently selected from H, and optionally substituted alkyl groups, aryl groups, heteroaryl groups and cycloalkyl groups. More preferably, $R^{12}$, $R^{13}$ and $R^{14}$ are independently selected from H, alkyl, aryl and cycloalkyl.

In one embodiment $R^{13}$ and $R^{14}$ together define a piperidinyl, piperazinyl or a pyridyl group.

$R^5$ and $R^{5a}$ are independently selected from H, alkyl and alkenyl, each of which may be optionally substituted.

Preferably $R^5$ and $R^{5a}$ are independently selected from H, methyl, ethyl, propyl, ethenyl, propenyl. Most preferably $R^5$ and $R^{5a}$ are independently selected from H, ethyl and ethenyl.

$R^6$ is selected from an alkyl group, an alkenyl group, an alkynyl group, an aryl group, a heteroaryl group, a cycloalkyl group, a $(CH_2)_n$-aryl group, a $(CH_2)_n$-heteroaryl group and a $(CH_2)_n$-cycloalkyl group; each of which may be optionally substituted.

Preferably $R^6$ is selected from optionally substituted $(CH_2)_n$-aryl groups, $(CH_2)_n$-heteroaryl groups and $(CH_2)_n$-cycloalkyl groups. More preferably $R^6$ is an optionally substituted $(CH_2)_n$-aryl group. More preferably, $R^6$ is a $(CH_2)_n$-aryl group optionally substituted with one or more of halo, alkyl, $NO_2$, Me, $CF_3$ and OMe. More preferably, $R^6$ is a $(CH_2)_n$-aryl group optionally substituted with one or more of bromo, tert-butyl, Me and $CF_3$. More preferably, $R^6$ is a $(CH_2)_n$-aryl group optionally substituted with one or more of halo, $NO_2$, Me, $CF_3$ and OMe. More preferably, $R^6$ is a $(CH_2)_n$-aryl group optionally substituted with one or more of $NO_2$ and OMe. More preferably $R^6$ is selected from 3,5-bis(trifluoromethyl)benzyl, benzyl, 2-nitro-4,5-dimethoxybenzyl, 3,5-di-tert-butyl-benzyl, 3,5-di-bromo-benzyl, 3,5-di-methyl-benzyl and 9-methylanthracene. More preferably $R^6$ is selected from 3,5-bis(trifluoromethyl)benzyl, 3,5-di-tert-butyl-benzyl, 3,5-di-bromo-benzyl and 3,5-di-methyl-benzyl. Most preferably $R^6$ is selected from 3,5-bis(trifluoromethyl)benzyl, benzyl, 2-nitro-4,5-dimethoxybenzyl and 9-methylanthracene.

n=0 to 6. Preferably n=0 to 3, more preferably n=1.

$R^7$ is

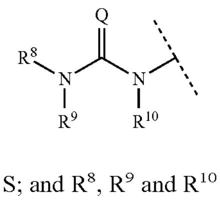

wherein Q is O or S; and $R^8$, $R^9$ and $R^{10}$ are independently selected from H, an alkyl group, an alkenyl group, an alkynyl group, an aryl group, a heteroaryl group and a cycloalkyl group, each of which may be optionally substituted, or $R^8$ and $R^9$ may together define an optionally substituted $C_3$-$C_{20}$ cycloalkyl group or an optionally substituted $C_5$-$C_{15}$ heteroaryl group.

Preferably $R^8$ is selected from an alkyl group, an aryl group, a heteroaryl group and a cycloalkyl group each of which may be optionally substituted. More preferably, $R^8$ is selected from alkyl group, an aryl group and a cycloalkyl group; each of which may be optionally substituted. Most preferably, $R^8$ is selected from 3,5-bis(trifluoromethyl)phenyl, 2-nitro-4,5-dimethoxyphenyl, phenyl and cyclohexane.

Preferably $R^9$ and $R^{10}$ are independently selected from H and an alkyl group. More preferably, $R^9$ and $R^{10}$ are independently selected from H, methyl and ethyl.

In one embodiment $R^8$ and $R^9$ define an optionally substituted $C_3$-$C_{20}$ cycloalkyl group or $C_5$-$C_{15}$ heteroaryl group.

Preferably $R^8$ and $R^9$ define an optionally substituted, piperidinyl, piperazinyl or pyridyl group.

$Y^-$ is a counterion. Examples of suitable counterions may include fluoride, chloride, bromide and iodide.

In one embodiment the cinchona alkaloid derivatives are dimeric species of formula (VIIc) or (VIId) in which $R^{15}$ represents a linking group between two compounds of formula VIIIa or VIIb respectively:

(VIIc)

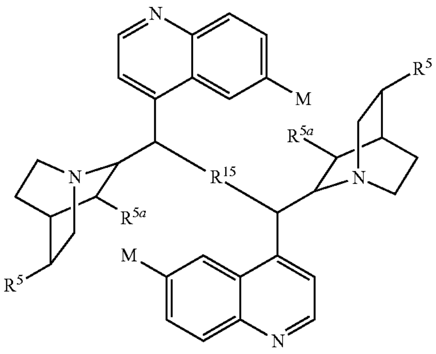

(VIId)

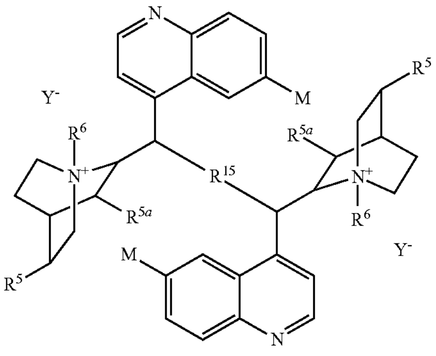

wherein M, $R^5$, $R^{5a}$ are as defined above and $R^{15}$ is selected from $O(CH_2)_n$-aryl-$(CH_2)_nO$, $O(CH_2)_n$-heteroaryl-$(CH_2)_nO$; each of which may be optionally substituted. Preferably $R^{15}$ is selected from the following:

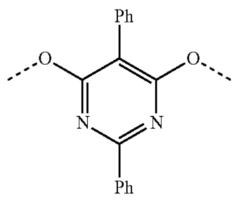

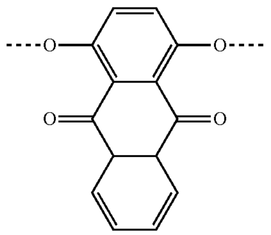

-continued

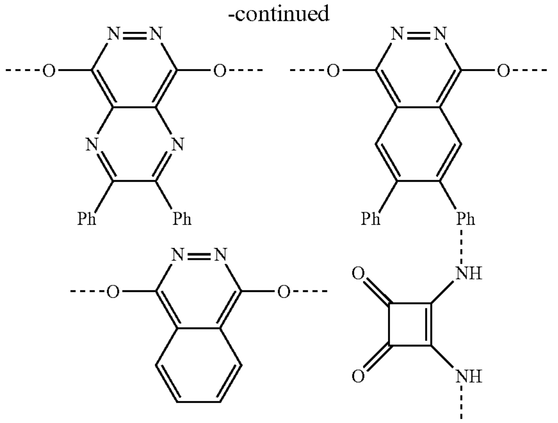

In one preferred embodiment, the catalyst is a compound of formula (VIIa) wherein M is selected from H, hydroxy, alkoxy, $O(CH_2)_n$-aryl, $O(CH_2)_n$-heteroaryl, $O(CH_2)_n$-cycloalkyl and $R^7$;

$R^4$ is selected from hydroxy, alkoxy, O-alkenyl, $O(CH_2)_n$-aryl, C(═O)$OR^{12}$, amino, $NR^{11}SO_2R^{12}$, and $R^7$;

Q is S;

$R^5$ and $R^{5a}$ are independently selected from H, methyl, ethyl, propyl, ethenyl, propenyl;

$R^8$ is selected from an alkyl group, an aryl group and a cycloalkyl group each of which may be optionally substituted by one or more of halo, $CF_3$, Me and OMe;

$R^9$, $R^{10}$, $R^{11}$ are independently selected from H and alkyl; and $R^{12}$ is selected from H and alkyl, aryl, cycloalkyl; each of which may be optionally substituted by one or more of halo, $CF_3$, Me and OMe.

In another preferred embodiment the catalyst is a compound of formula (VIIa) wherein M is selected from H, hydroxy, methoxy and $R^7$;

$R^4$ is selected from hydroxy, alkoxy, O-alkenyl, $O(CH_2)_n$-aryl, C(═O)$OR^{12}$, amino, $NR^{11}SO_2R^{12}$ and $R^7$;

Q is S;

$R^5$ and $R^{5a}$ are independently selected from H, methyl, ethyl, ethenyl;

$R^9$ and $R^{10}$ are H; and $R^8$ is selected from an alkyl group, an aryl group and a cycloalkyl group;

In another preferred embodiment the catalyst is a compound of formula (VIIa) wherein M is selected from H, hydroxy, methoxy and $R^7$;

$R^4$ is selected from hydroxy, alkoxy, O-alkenyl, $O(CH_2)_n$-aryl, C(═O)$OR^{12}$, amino, $NR^{11}SO_2R^{12}$, and $R^7$;

Q is S;

$R^5$ and $R^{5a}$ are independently selected from H, methyl, ethyl, ethenyl;

$R^9$ and $R^{10}$ are H; and $R^8$ is selected from an alkyl and aryl group optionally substituted by one or more of halo, $CF_3$, Me and OMe;

In another preferred embodiment, the catalyst is a compound of formula (VIIb) wherein M is selected from H, hydroxy, alkoxy, $O(CH_2)_n$-aryl, $O(CH_2)_n$-heteroaryl, $O(CH_2)_n$-cycloalkyl and $R^7$.

$R^4$ is selected from hydroxy, alkoxy, O-alkenyl, $O(CH_2)_n$-aryl, C(═O)$OR^{12}$, amino, $NR^{11}SO_2R^{12}$, and $R^7$;

Q is S;

$R^5$ and $R^{5a}$ are independently selected from H, methyl, ethyl, propyl, ethenyl, propenyl;

$R^6$ is selected from $(CH_2)_n$-aryl groups, $(CH_2)_n$-heteroaryl groups and $(CH_2)_n$-cycloalkyl groups, each of which may optionally be substituted with one or more halo, $NO_2$, $CF_3$, Me and OMe groups;

$R^8$ is selected from an alkyl group, an aryl group and a cycloalkyl group each of which may be optionally substituted by one or more of halo, $CF_3$, Me and OMe;

$R^9$, $R^{10}$, $R^{11}$ are independently selected from H and alkyl; and $R^{12}$ is selected from H, alkyl, aryl and cycloalkyl; each of which may be optionally substituted by one or more of halo, $CF_3$, Me and OMe.

In another preferred embodiment, the catalyst is a compound of formula (VIIb) wherein M is selected from H, hydroxy, alkoxy, $O(CH_2)_n$-aryl, $O(CH_2)_n$-heteroaryl, $O(CH_2)_n$-cycloalkyl and $R^7$;

$R^4$ is selected from hydroxy, alkoxy, O-alkenyl, $O(CH_2)_n$-aryl, C(═O)O$R^{12}$, amino, $NR^{11}SO_2R^{12}$, and $R^7$;

Q is S;

$R^5$ and $R^{5a}$ are independently selected from H, methyl, ethyl, propyl, ethenyl, propenyl;

$R^6$ is selected from $(CH_2)_n$-aryl groups, $(CH_2)_n$-heteroaryl groups and $(CH_2)_n$-cycloalkyl groups, each of which may optionally be substituted with one or more halo, alkyl, $NO_2$, haloalkyl and methoxy groups;

$R^8$ is selected from an alkyl group, an aryl group and a cycloalkyl group each of which may be optionally substituted by one or more of halo, $CF_3$, Me and OMe;

$R^9$, $R^{10}$, $R^{11}$ are independently selected from H and alkyl; and $R^{12}$ is selected from H, alkyl, aryl and cycloalkyl; each of which may be optionally substituted by one or more of halo, $CF_3$, Me and OMe.

In another preferred embodiment the catalyst is a compound of formula (VIIb) wherein M is selected from H, hydroxy, methoxy and $R^7$;

$R^4$ is selected from hydroxy, alkoxy, O-alkenyl, $O(CH_2)_n$-aryl, C(═O)O$R^{12}$, amino, $NR^{11}SO_2R^{12}$, and $R^7$;

Q is S;

$R^5$ and $R^{5a}$ are independently selected from H, methyl, ethyl, ethenyl;

$R^6$ is selected from a benzyl group which may be optionally substituted with one or more of halo, alkyl, $NO_2$, haloalkyl and alkoxy;

$R^9$ and $R^{10}$ are H; and $R^8$ is selected from an alkyl and aryl group optionally substituted by one or more of halo, $CF_3$, Me and OMe;

In another preferred embodiment the catalyst is a compound of formula (VIIb) wherein M is selected from H, hydroxy, methoxy and $R^7$;

$R^4$ is selected from hydroxy, alkoxy, O-alkenyl, $O(CH_2)_n$-aryl, C(═O)O$R^{12}$, amino, $NR^{11}SO_2R^{12}$, and $R^7$;

Q is S;

$R^5$ and $R^{5a}$ are independently selected from H, methyl, ethyl, ethenyl;

$R^6$ is selected from a benzyl group which may be optionally substituted with one or more of halo, $NO_2$, $CF_3$, Me, tert-butyl and OMe;

$R^9$ and $R^{10}$ are H; and $R^8$ is selected from an alkyl and aryl group optionally substituted by one or more of halo, $CF_3$, Me and OMe;

In another preferred embodiment the catalyst is a compound of formula (VIIb) wherein M is selected from H, hydroxy, methoxy and $R^7$;

$R^4$ is selected from hydroxy, alkoxy, O-alkenyl, $O(CH_2)_n$-aryl, C(═O)O$R^{12}$, amino, $NR^{11}SO_2R^{12}$, and $R^7$;

Q is S;

$R^5$ and $R^{5a}$ are independently selected from H, methyl, ethyl, ethenyl;

$R^6$ is selected from a benzyl group which may be optionally substituted with one or more of halo, $NO_2$, $CF_3$, Me and OMe;

$R^9$ and $R^{10}$ are H; and $R^8$ is selected from an alkyl and aryl group optionally substituted by one or more of halo, $CF_3$, Me and OMe;

In another preferred embodiment the catalyst is a compound of formula (VIIb) wherein M is selected from H, hydroxy, methoxy and $R^7$;

$R^4$ is selected from hydroxy, alkoxy, O-alkenyl, $O(CH_2)_n$-aryl, C(═O)O$R^{12}$, amino, $NR^{11}SO_2R^{12}$, and $R^7$;

Q is S;

$R^5$ and $R^{5a}$ are independently selected from H, methyl, ethyl, ethenyl;

$R^6$ is selected from 3,5-di-tert-butyl-benzyl, 3,5-di-bromo-benzyl, 3,5-di-methyl-benzyl, 3,5-bis(trifluoromethyl)benzyl, 2-nitro-4,5-dimethoxybenzyl and benzyl;

$R^9$ and $R^{10}$ are H; and $R^8$ is selected from an alkyl and aryl group optionally substituted by one or more of halo, $CF_3$, Me and OMe;

In another preferred embodiment the catalyst is a compound of formula (VIIb) wherein M is selected from H, hydroxy, methoxy and $R^7$;

$R^4$ is selected from hydroxy, alkoxy, O-alkenyl, $O(CH_2)_n$-aryl, C(═O)O$R^{12}$, amino, $NR^{11}SO_2R^{12}$, and $R^7$;

Q is S;

$R^5$ and $R^{5a}$ are independently selected from H, methyl, ethyl, ethenyl;

$R^6$ is selected from 3,5-bis(trifluoromethyl)benzyl, 2-nitro-4,5-dimethoxybenzyl and benzyl;

$R^9$ and $R^{10}$ are H; and $R^8$ is selected from an alkyl and aryl group optionally substituted by one or more of halo, $CF_3$, Me and OMe;

In another preferred embodiment the catalyst is selected from the following:

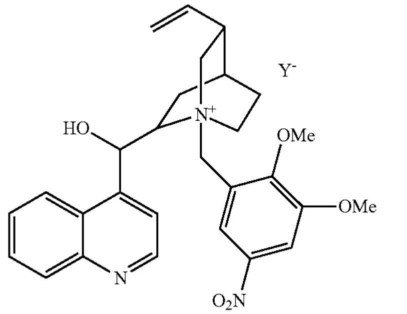

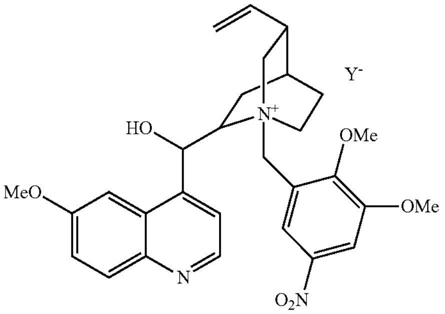

-continued
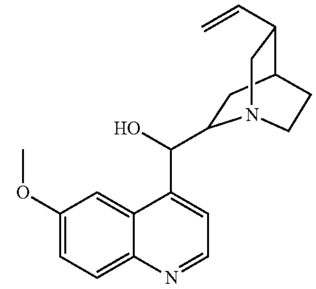
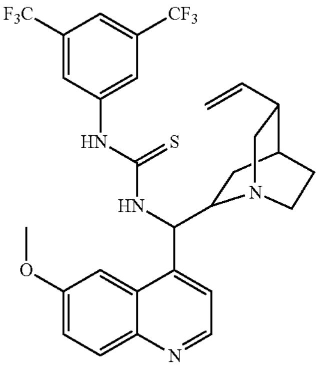
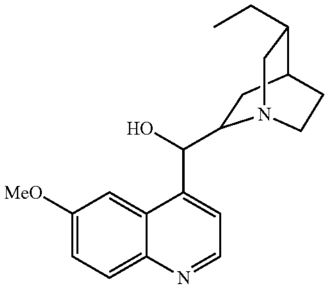
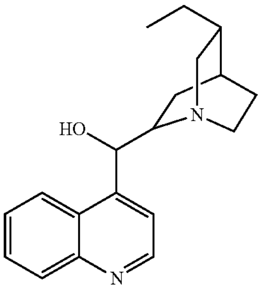
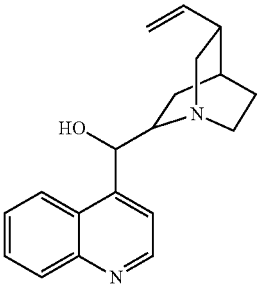
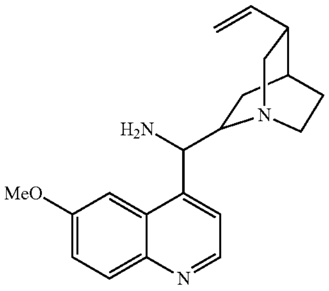
-continued
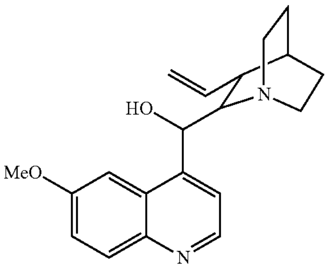
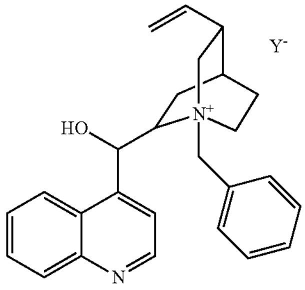
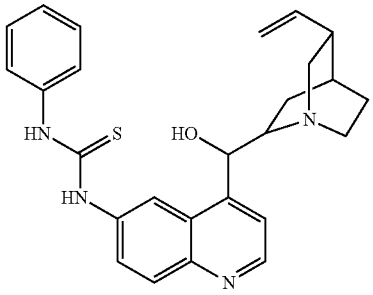
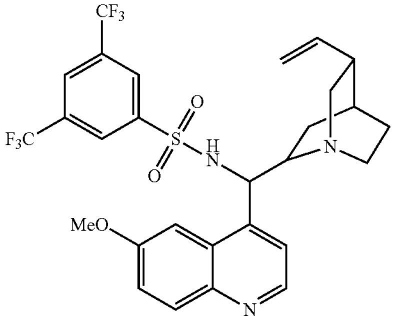
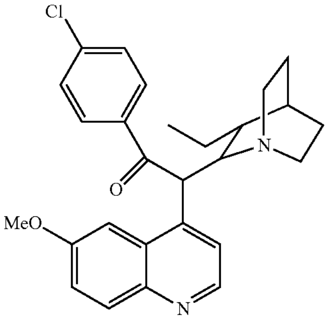

-continued
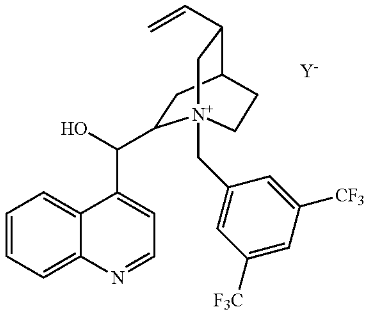
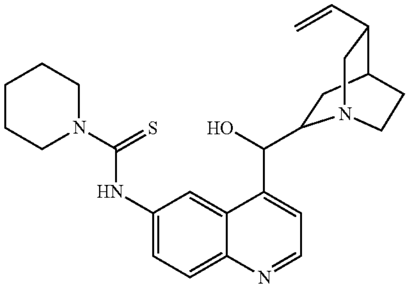
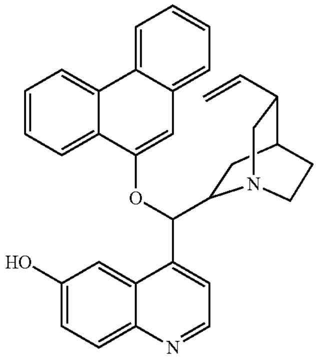
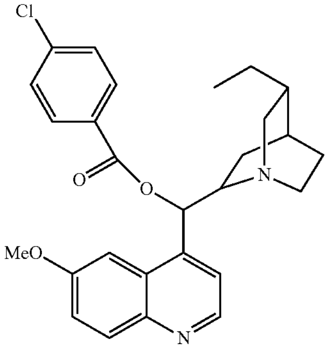
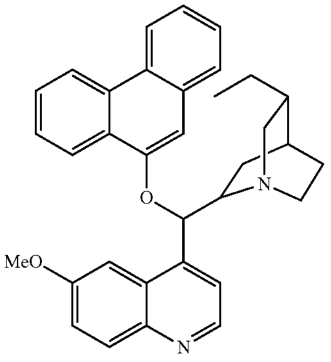
-continued
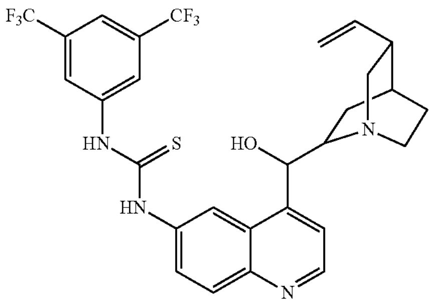
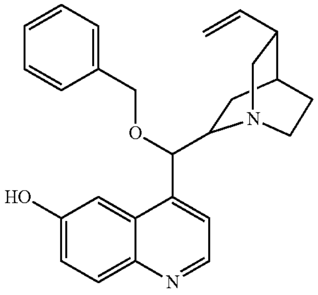
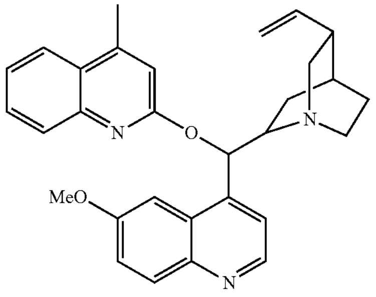
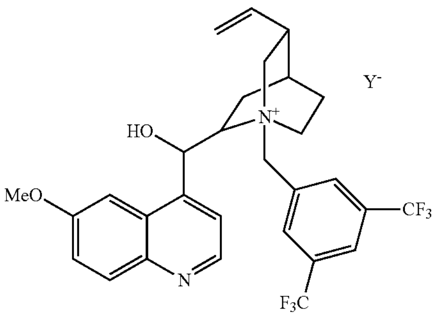
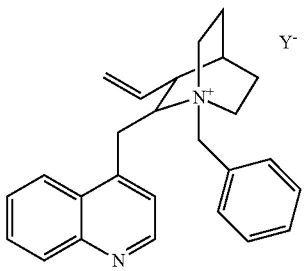

-continued
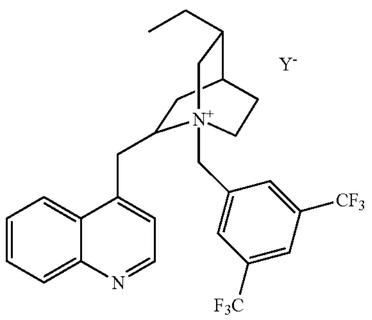
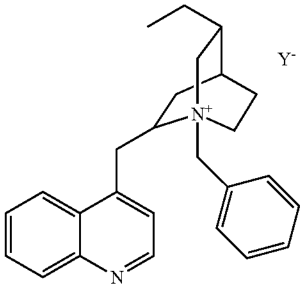
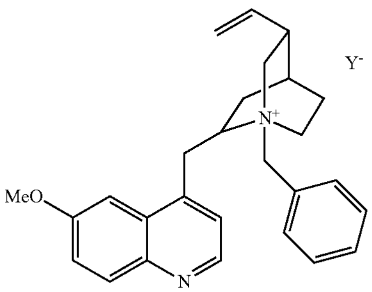
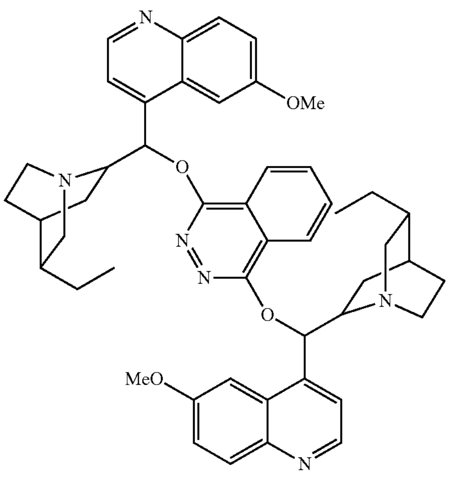
-continued
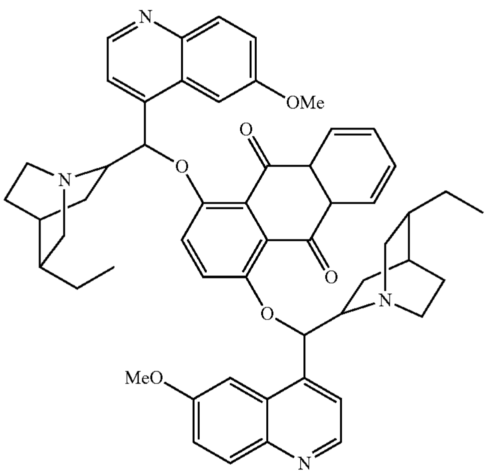
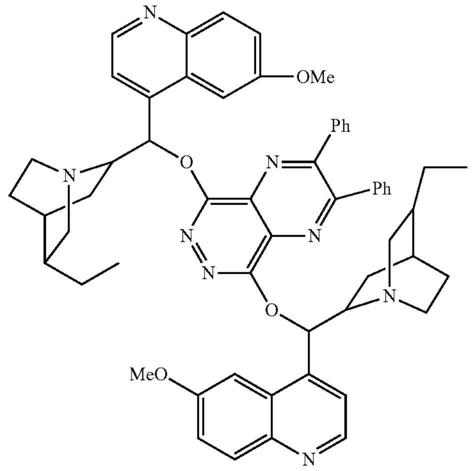
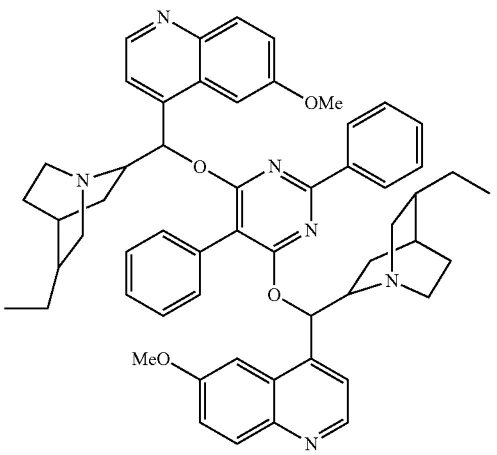

-continued

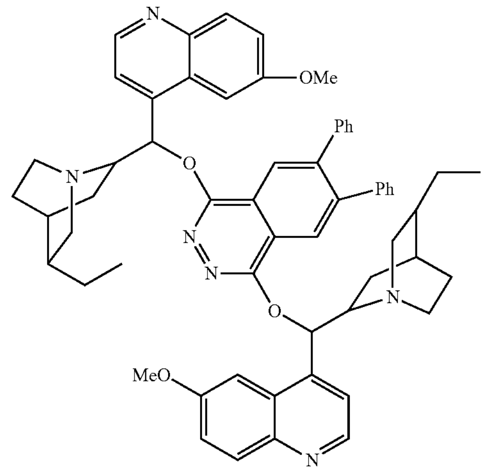

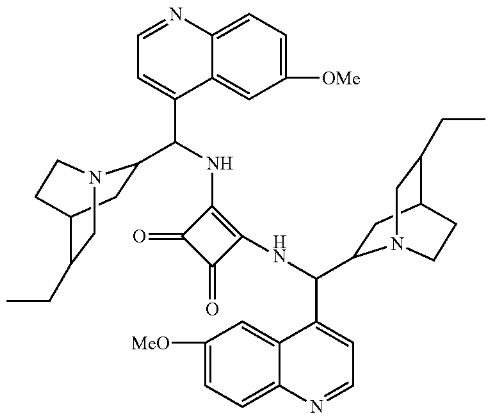

wherein $Y^-$ is a counterion. Examples of suitable counterions include fluoride, chloride, bromide and iodide. Preferably the counterion is bromide.

In another preferred embodiment the catalyst is selected from those catalysts in the preceding paragraph as well as the following:

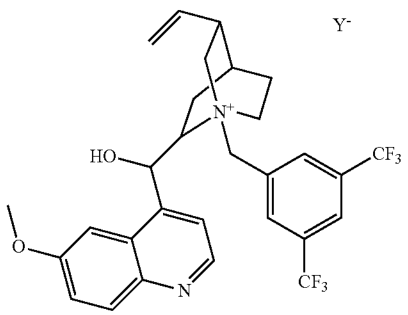

-continued

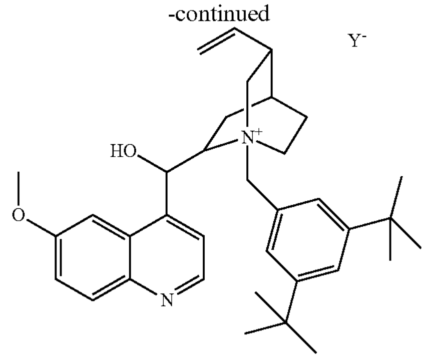

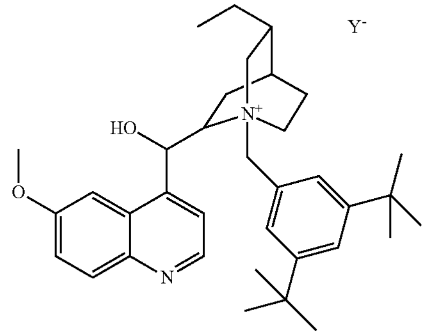

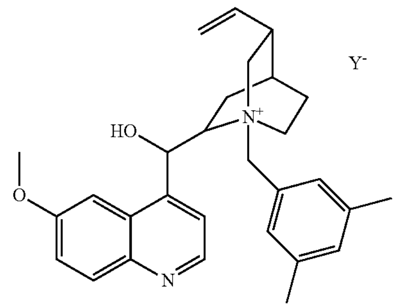

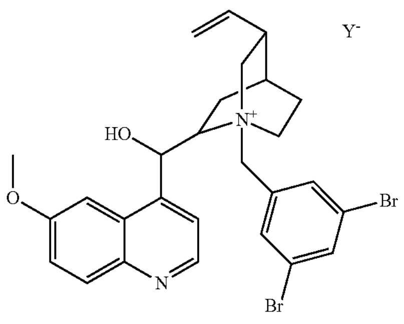

wherein $Y^-$ is a counterion. Examples of suitable counterions include fluoride, chloride, bromide and iodide. Preferably the counterion is bromide.

In another embodiment the catalyst is selected from those of the preceding paragraph only.

In another embodiment the catalyst is selected from the following:

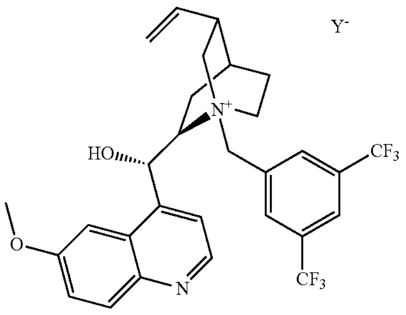

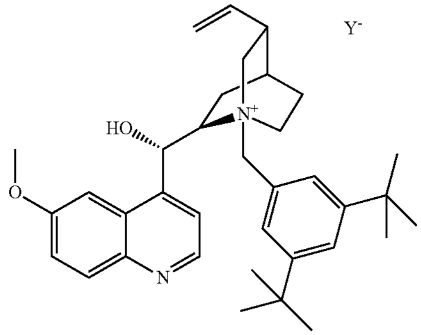

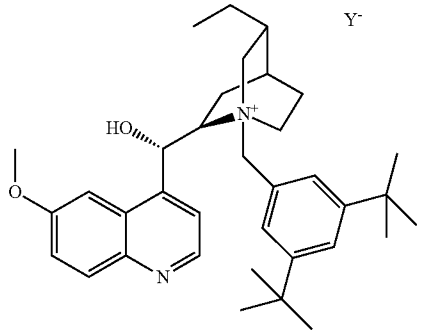

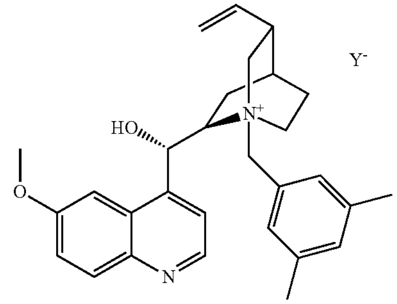

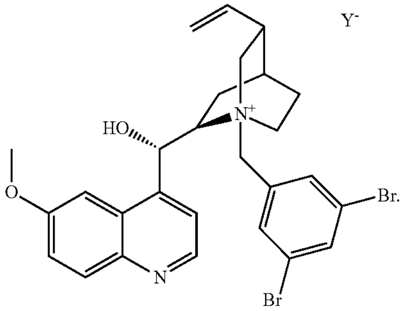

In another preferred embodiment the catalyst is selected from:

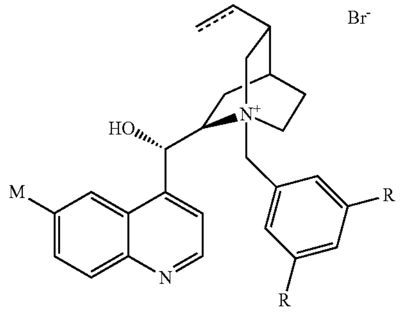

wherein R is independently selected from tert-butyl, $CF_3$, Me and Br, and M is selected from H and OMe; and wherein indicates either a double bond or single bond.

In another preferred embodiment the catalyst is selected from:

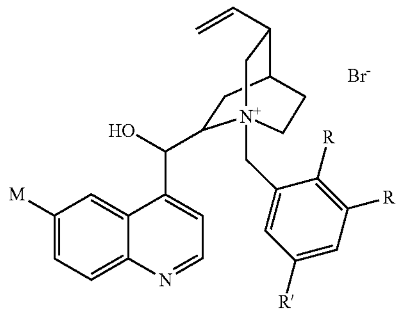

wherein R is selected from H and $CF_3$, R' is selected from H and $NO_2$ and M is selected from H and OMe.

In another preferred embodiment the catalyst is selected from:

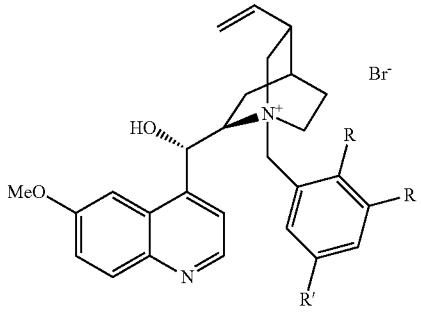

wherein R and R' are independently selected from $NO_2$ and OMe, preferably R' is $NO_2$ or H and R is OMe or H.

In another preferred embodiment the catalyst is selected from N-(3,5-ditrifluoromethylbenzyl)quinidinium bromide, N-(3,5-ditertbutylbenzyl)quinidinium bromide, N-(3,5-ditertbutylbenzyl)dihydroquinidinium bromide, N-(3,5-dimethylbenzyl)quinidinium bromide, N-(3,5-dibromobenzyl) quinidinium bromide, N-benzylcinchonidinium bromide, N-(4,5-dimethoxy-2-nitrobenzyl)cinchonidinium bromide and N-(3,5-bis(trifluoromethyl)benzyl)cinchonidinium bromide, N-benzylquinidinium bromide, N-(2-nitro-4,5-dimethoxybenzyl)quinidinium bromide.

In another preferred embodiment the catalyst is selected from N-benzylcinchonidinium bromide, N-(4,5-dimethoxy- 2-nitrobenzyl)cinchonidinium bromide and N-(3,5-bis(trifluoromethyl)benzyl)cinchonidinium bromide, N-benzylquinidinium bromide, N-(2-nitro-4,5-dimethoxybenzyl) quinidinium bromide. In another embodiment the catalyst is selected from N-(3,5-ditrifluoromethylbenzyl)quinidinium bromide, N-(3,5-ditertbutylbenzyl)quinidinium bromide, N-(3,5-ditertbutylbenzyl)dihydroquinidinium bromide, N-(3,5-dimethylbenzyl)quinidinium bromide, N-(3,5-dibromobenzyl)quinidinium bromide. Preferably the catalyst is selected from N-benzylquinidinium bromide, N-(4,5-dimethoxy-2-nitrobenzyl)quinidinium bromide.

In another embodiment the catalyst is selected from N-(3,5-ditrifluoromethylbenzyl)quinidinium bromide, N-(3,5-ditertbutylbenzyl)quinidinium bromide, N-(3,5-ditertbutylbenzyl)dihydroquinidinium bromide, N-(3,5-dimethylbenzyl)quinidinium bromide, N-(3,5-dibromobenzyl) quinidinium bromide, N-benzylcinchonidinium bromide, N-(4,5-dimethoxy-2-nitrobenzyl)cinchonidinium bromide and N-(3,5-bis(trifluoromethyl)benzyl)cinchonidinium bromide, N-benzylquinidinium bromide, N-(2-nitro-4,5-dimethoxybenzyl)quinidinium bromide and tetrabutylammonium bromide, tetraethylammonium bromide, triphenylbutylammonium bromide, trimethylphenylphosphonium bromide and tetrabutylphosphonium bromide.

Throughout the specification, where substituents M, $R^4$, $R^5$, $R^{5a}$, $R^6$, $R^8$ to $R^{14}$ are defined as optionally substituted, examples of suitable substituents may include one or more of hydroxy, alkyl, aryl, halo, alkoxy, haloalkyl, haloalkoxy, amino, aminoalkyl, nitro and cycloalkyl. Preferably, suitable substitutents are selected from one or more of hydroxy, alkyl, alkoxy, halo, haloalkoxy, nitro and aryl. More preferably, suitable substitutents are selected from one or more hydroxy, methyl, ethyl, methoxy, ethoxy, halo, $NO_2$, $CF_3$ and phenyl groups.

It will be appreciated by a person skilled in the art that the some of the above catalysts possess at least two chiral centres and thus give rise to diastereoisomers. Where stereochemistry is not specifically indicated it will be understood that all diastereoisomers are encompassed by the structures shown.

Preferably the catalysts are those of formulae VIIa-d which provide compounds of formula (V) with the S-configuration at the chiral centre denoted by *.

In one embodiment the catalyst loading with respect to the compound of formula (IV) is less than or equal to about 1:1. In another embodiment the catalyst loading with respect to the compound of formula (IV) is less than or equal to about 0.5:1. In another embodiment the catalyst loading with respect to the compound of formula (IV) is less than or equal to about 0.2:1. Preferably, the catalyst loading with respect to the compound of formula (IV) is about 0.05:1.

The Processes

In one aspect, the present invention provides a process for the preparation of a compound of formula (I), and pharmaceutically acceptable salts, solvates and prodrugs thereof:

(I)

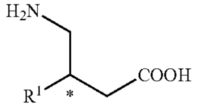

which process comprises the step of preparing a compound of formula (IV) by reacting a compound of formula (III) with a compound of formula (II):

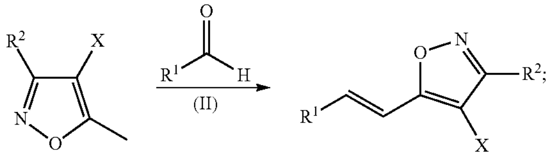

(III) (IV)

wherein $R^1$, $R^2$, and X are as defined herein above.

In one embodiment the reaction comprises a base. Preferably the base provides a source of hydroxide. Examples of suitable bases may include sodium hydroxide, lithium hydroxide and potassium hydroxide. Preferably, the base is sodium hydroxide.

Preferably, the reaction is conducted in the presence of an aqueous solvent, such as water, or a mixture of solvents comprising water. Preferably the solvent comprises water and a $C_{1-6}$ alcohol, such as methanol or ethanol.

In another embodiment, the reaction comprises a further organic solvent. The further organic solvent may be selected from tetrahydrofuran, 1,4-dioxan, diethyl ether. Preferably, the further organic solvent is tetrahydrofuran.

In one embodiment the ratio of water to $C_{1-6}$ alcohol is between 0.1:1 and 100:1. In another embodiment the ratio of water to $C_{1-6}$ alcohol is between 0.1:1 and 50:1. In another embodiment the ratio of water to $C_{1-6}$ alcohol is between 0.1:1 and 20:1. In another embodiment the ratio of water to $C_{1-6}$ alcohol is between 1:1 and 20:1.

Preferably, the solvent is 9:1 water to $C_{1-6}$ alcohol. Preferably the $C_{1-6}$ alcohol is ethanol or methanol.

In another embodiment, the solvent is 7:3 water to $C_{1-6}$ alcohol. Preferably the $C_{1-6}$ alcohol is methanol.

Optionally, the coupling of a compound of formula (III) and a compound of formula (II) and subsequent dehydration to yield a compound of formula (IV) can be carried out in two stages with isolation of the intermediate compound of formula (IIIa) (Scheme 4).

Scheme 4

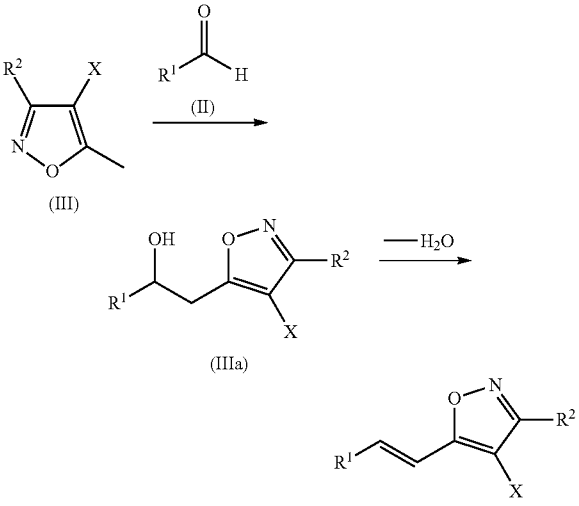

(III)

(IIIa)

(IV)

The dehydration stage may be carried out by first activating the hydroxyl group of a compound of formula (IIIa) using any method commonly known in the art. In one embodiment, the hydroxyl group is mesylated with mesyl chloride in the presence of triethylamine. Elimination of methanesulfonic acid yields a compound of formula (IV).

Preferably the dehydration is carried out in the presence of a solvent. In one embodiment the solvent is selected from dichloromethane, tetrahydrofuran, 1,4-dioxan, diethylether, toluene, acetone, ethyl acetate. Preferably the solvent is dichloromethane.

In an alternative aspect the present invention provides a process for the preparation of a compound of formula (I), and pharmaceutically acceptable salts, solvates and prodrugs thereof:

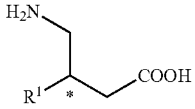

(I)

wherein:

$R^1$ is selected from an alkyl group, an alkenyl group, an alkynyl group and a cycloalkyl group, each of which may be optionally substituted; and * denotes a chiral centre;

which process comprises preparing a compound of formula (IV) by reacting a compound of formula (IIIA) with a compound of formula (II) to form a compound of formula (IIIB):

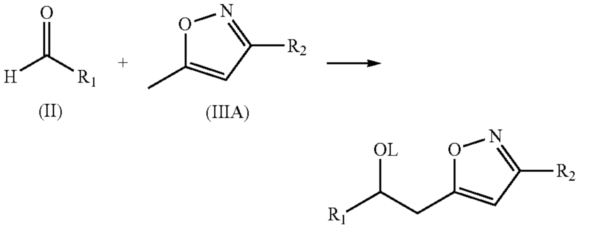

(II) (IIIA)

(IIIB)

wherein:

L is a hydroxyl activating group, $R^1$ is defined above in relation to the compound of formula (I); and $R^2$ is an alkyl group or aryl group, each of which may be optionally substituted; and converting the compound of formula (IIIB) to a compound of formula (IIIC):

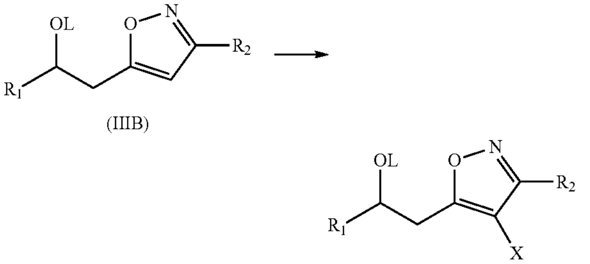

(IIIB)

(IIIC)

wherein:

X is an electron withdrawing group; and converting the compound of formula (IIIC) to a compound of formula (IV).

In one embodiment the reaction of (II) and (IIIA) is carried out in the presence of a base, such as LDA. In one embodiment the reaction of (II) and (IIIA) is carried out in the presence of a base and then the hydroxyl activating group is added with or without isolation of the intermediate hydroxyl compound.

In a preferred embodiment X in the compounds of formula (IIIB) and (IIIC) is nitro. In such an embodiment, suitable reagents for generation of NO2+ will be apparent to the skilled person. Exemplary conditions include $HNO_3$/$H_2SO_4$ and tetramethyl ammonium nitrate and trifluoroacetyc anhydride.

The conversion of the compound of formula (IIIC) to the compound of formula (IV) may be carried out by any method known in the art. Preferably the reaction is carried out in the presence of an organic base, preferably the reaction is carried out in the presence of an amine such as triethylamine.

In one embodiment the process further comprises the step of reacting a compound of formula (IV) with nitromethane in the presence of a catalyst to provide a compound of formula (V):

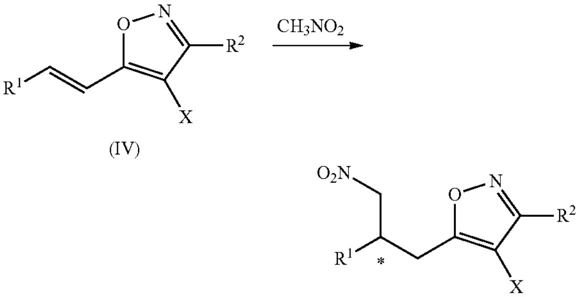

(IV)

(V)

wherein $R^1$, $R^2$ and X are as defined hereinabove.

In one embodiment the reaction of the compound of formula (IV) with nitromethane is carried out in the presence of a base. Preferably the base is a source of carbonate. Examples of suitable bases include, but are not limited to, potassium carbonate, sodium carbonate and cesium carbonate. Preferably the base is potassium carbonate.

In one embodiment the reaction of the compound of formula (IV) with nitromethane is carried out in a solvent. Examples of suitable solvents include tetrahydrofuran, 1,4-dioxan, toluene and xylene. Preferably, the solvent is toluene. In one embodiment the solvent is toluene recycled from previous reactions comprising reacting a compound of formula (IV) with nitromethane in the presence of a catalyst to provide a compound of formula (V).

In one embodiment the reaction of the compound of formula (IV) with nitromethane is conducted at a temperature of between −70° C. to 30° C. In another embodiment the reaction is conducted at a temperature of between −70° C. to 0° C. In another embodiment the reaction is conducted at a temperature of between −50° C. to −20° C. Preferably the reaction is conducted at a temperature of about −37° C.

In one embodiment the reaction of the compound of formula (IV) with nitromethane is conducted at a temperature of between −70° C. to 50° C. In another embodiment the reaction is conducted at a temperature of between 0° C. to 30° C. In another embodiment the reaction is conducted at a temperature of between 20° C. to 30° C. Preferably the reaction is conducted at room temperature.

In one embodiment the reaction of the compound of formula (IV) with nitromethane provides a compound of formula (V) with an enantiomeric excess of greater than about 60%. In another embodiment the enantiomeric excess is greater than about 70%. In another embodiment the enantiomeric excess is greater than about 80%. Preferably the enantiomeric excess is greater than about 90%.

In one embodiment compound of formula (V) is enantiomerically enriched by re-crystallization. In one embodiment re-crystallization is in isopropanol or mixtures of isopropanol and hexane.

In one embodiment the enantiomerically enriched compound of formula (V) has an enantiomeric excess of greater than about 90%, more preferably greater than about 95%, more preferably greater then about 99%.

In one embodiment the process further comprises the step of hydrolysing the compound of formula (V) to provide a compound of formula (VI)

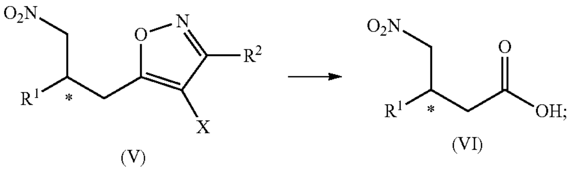

(V) (VI)

wherein $R^1$, $R^2$ and X are as defined hereinabove.

In one embodiment the process further comprises the step of hydrolysing the compound of formula (VIb) to provide a compound of formula (I)

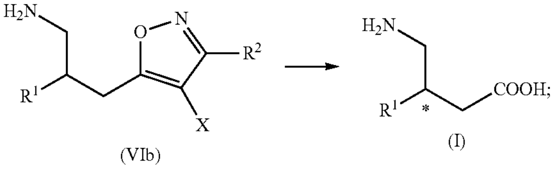

(VIb) (I)

wherein $R^1$, $R^2$ and X are as defined hereinabove; with the proviso that X is not $NO_2$.

The hydrolysis may be carried out by any method commonly known in the art.

In one embodiment the hydrolysis of compound (V) or (VIb) is carried out in the presence of a base. Preferably the base is a source of hydroxide. Examples of suitable bases include, but are not limited to, sodium hydroxide, potassium hydroxide and lithium hydroxide. Preferably the base is sodium hydroxide, more preferably aqueous sodium hydroxide.

The hydrolysis may be performed in the presence of an organic solvent. Examples of suitable organic solvent include, but are not limited to, tetrahydrofuran, 1,4-dioxan and diethyl ether. Preferably the solvent is tetrahydrofuran.

In one embodiment the solvent is a mixture of organic solvent and water. Preferably, the solvent is a mixture of water and tetrahydrofuran.

In one embodiment the process further comprises the step of reducing the compound of formula (VI) to provide a compound of formula (I)

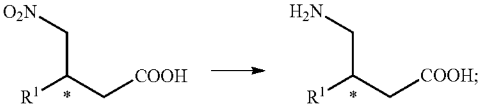

(VI) (I)

wherein $R^1$, $R^2$ and X are as defined hereinabove.

In one embodiment the process further comprises the step of reducing the compound of formula (V) to provide a compound of formula (VIb)

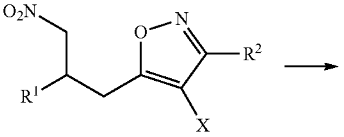

(V)

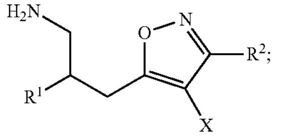

(VIb)

wherein $R^1$, $R^2$ and X are as defined hereinabove; with the proviso that X is not $NO_2$.

The reduction may be accomplished by any commonly known method in the art. Examples of suitable reduction reactions include, but are limited to, hydrogenation, transfer hydrogenation or transition metal and acid reduction.

Preferably the reduction of a compound of formula (VI) or (V) is accomplished by catalytic hydrogenation. Optionally, the hydrogenation is conducted in the presence of an acid. Preferably the acid is hydrochloric acid.

Preferred hydrogenation catalysts include palladium on carbon and Raney nickel.

In one embodiment the reduction is conducted in a solvent. Suitable solvents include, but are not limited to ethanol, methanol and ethyl acetate. Preferably the solvent is ethanol.

In one embodiment the reduction may be performed accordingly to the procedure described in F. Felluga, G. Pitacco, E. Valentin, C. D. Venneri *Tetrahedron: Asymm,* 2008, 945.

In another aspect of the invention there is provided a process for the preparation of a compound of formula (IV), and salts thereof, which process comprises reacting a compound of formula (III) with a compound of formula (II):

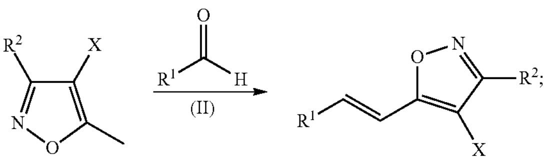

(III) (IV)

as described hereinabove, wherein $R^1$, $R^2$ and X are as defined above.

In another aspect of the invention, there is provided the use of a compound of formula (IV)

(IV)

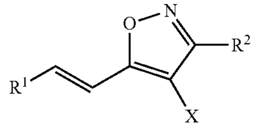

wherein $R^1$, $R^2$ and X are as defined above in the preparation of a compound of formula (I).

Another aspect of the invention relates to a process for the preparation of a compound of formula (I), and pharmaceutically acceptable salts, solvates and prodrugs thereof:

(I)

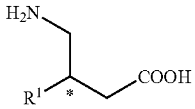

wherein:

$R^1$ is selected from an alkyl group, an alkenyl group, an alkynyl group and a cycloalkyl group, each of which may be optionally substituted; and * denotes a chiral centre;

which process comprises the step of reacting a compound of formula (IV) with nitromethane in the presence of a catalyst to provide a compound of formula (V);

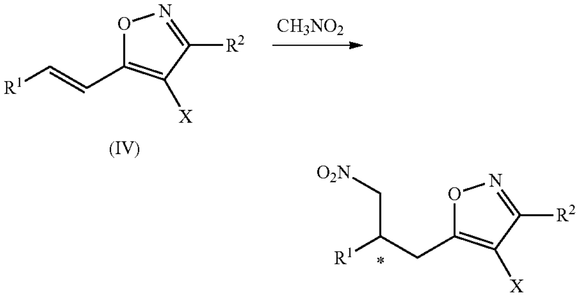

(IV)

(V)

wherein:

$R^1$ and * are as defined above in relation to the compound of formula (I); $R^2$ is an alkyl group or aryl group, each of which may be optionally substituted; and X is an electron withdrawing group.

In one embodiment the reaction is carried out in the presence of a base. Preferably the base is a source of carbonate. Examples of suitable bases include, but are not limited to, potassium carbonate, sodium carbonate and cesium carbonate. Preferably the base is potassium carbonate.

In one embodiment the reaction is carried out in a solvent. Examples of suitable solvents include tetrahydrofuran, 1,4-dioxan, toluene and xylene. Preferably, the solvent is toluene. In one embodiment the solvent is toluene recycled from previous reactions comprising reacting a compound of formula (IV) with nitromethane in the presence of a catalyst to provide a compound of formula (V).

In one embodiment the reaction is conducted at a temperature of between −70° C. to 30° C. In another embodiment the reaction is conducted at a temperature of between −70° C. to 0° C. In another embodiment the reaction is conducted at a temperature of between −50° C. to −20° C. Preferably the reaction is conducted at a temperature of about −37° C.

In one embodiment the reaction is conducted at a temperature of between −70° C. to 50° C. In another embodiment the reaction is conducted at a temperature of between 0° C. to 30° C. In another embodiment the reaction is conducted at a temperature of between 20° C. to 30° C. Preferably the reaction is conducted at room temperature.

In an alternative aspect the present invention provides a process for the preparation of a compound of formula (I), and pharmaceutically acceptable salts, solvates and prodrugs thereof:

(I)

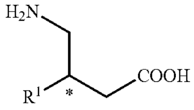

which process comprises the step of reacting a compound of formula (IIA) with a compound of formula (III) in the presence of a catalyst to provide a compound of formula (V);

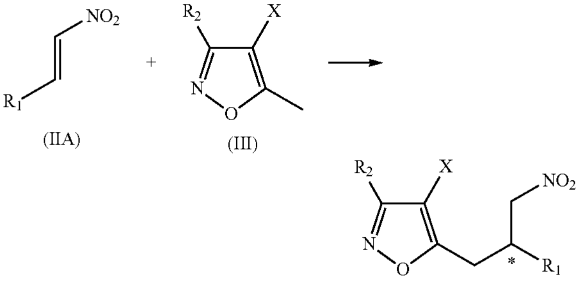

(IIA)

(III)

(V)

wherein $R^1$, $R^2$ and X are as defined hereinabove.

In one embodiment the reaction of the compound of formula (IIA) with a compound of formula (III) is carried out in the presence of a base. Preferably the base is a source of carbonate. Examples of suitable bases include, but are not limited to, potassium carbonate, sodium carbonate and cesium carbonate. Preferably the base is potassium carbonate.

In one embodiment the reaction provides a compound of formula (V) with an enantiomeric excess of greater than about 60%. In another embodiment the enantiomeric excess is greater than about 70%. In another embodiment the enantiomeric excess is greater than about 80%. Preferably the enantiomeric excess is greater than about 90%.

In one embodiment compound of formula (V) is enantiomerically enriched by re-crystallization. In one embodiment re-crystallization is in isopropanol or mixtures of isopropanol and hexane.

In one embodiment the enantiomerically enriched compound of formula (V) has an enantiomeric excess of greater than about 90%, more preferably greater than about 95%, more preferably greater then about 99%

In one embodiment the compound of formula (IV) may be prepared by reacting a compound of formula (III) with a compound of formula (II):

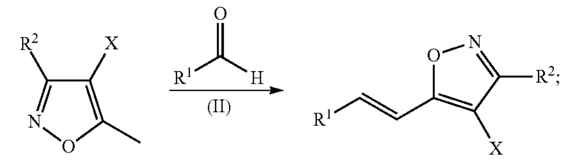

(III) (II) (IV)

as described hereinabove.

In alternative embodiment the compound of formula (IV) may be prepared by reacting a compound of formula (IIIA) with a compound of formula (II) to form a compound of formula (IIIB):

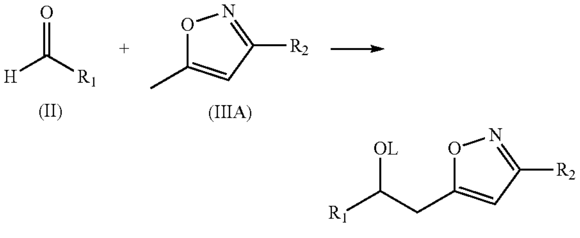

(II) (IIIA) (IIIB)

and converting the compound of formula (IIIB) to a compound of formula (IIIC):

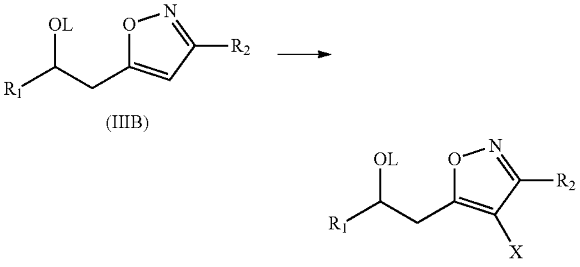

(IIIB) (IIIC)

and converting the compound of formula (IIIC) to a compound of formula (IV), as described hereinabove.

In one embodiment the compound of formula (V) may be prepared by reacting a compound of formula (IIA) with a compound of formula (III) in the presence of a catalyst;

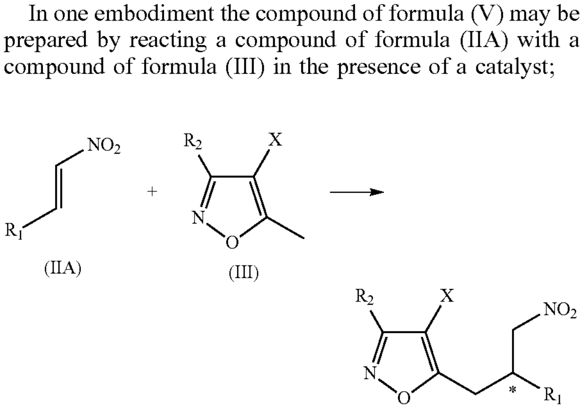

(IIA) (III) (V)

as described hereinabove.

In one embodiment the process further comprises the step of hydrolysing the compound of formula (V) to provide a compound of formula (VI)

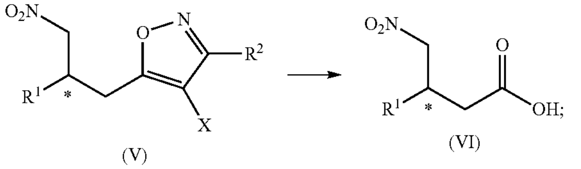

(V) (VI)

as described hereinabove.

In one embodiment the process further comprises the step of hydrolysing the compound of formula (VIb) to provide a compound of formula (I);

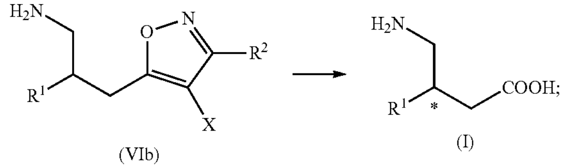

(VIb) (I)

wherein $R^1$, $R^2$ and X are as defined hereinabove; with the proviso that X is not $NO_2$, as described hereinabove.

In one embodiment the process further comprises the step of reducing the compound of formula (VI) to provide a compound of formula (I)

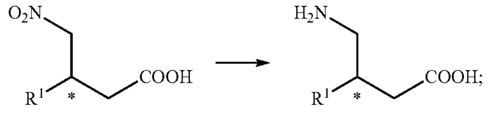

(VI) (I)

as described herein above.

In one embodiment the process further comprises the step of reducing the compound of formula (V) to provide a compound of formula (VIb);

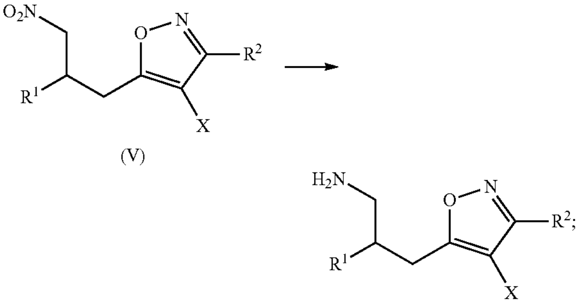

(V) (VIb)

wherein $R^1$, $R^2$ and X are as defined hereinabove; with the proviso that X is not $NO_2$, as described hereinabove.

In another aspect of the invention there is provided a process for the preparation of a compound of formula (V), and salts thereof, which process comprises reacting a compound of formula (IV), with nitromethane in the presence of a catalyst:

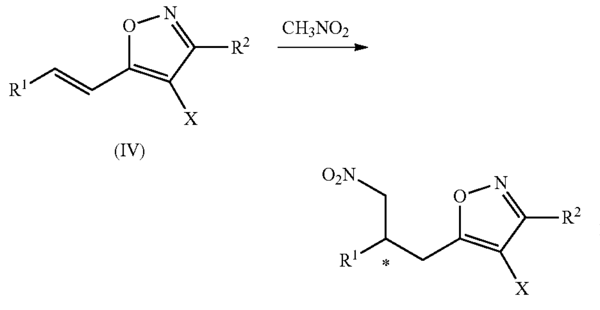

(IV)

(V)

as described hereinabove, wherein $R^1$, $R^2$ and X are as defined above.

In another aspect of the invention, there is provided the use of a compound of formula (V)

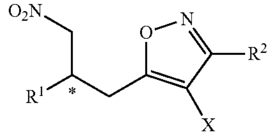

(V)

wherein $R^1$, $R^2$ and X are as defined above, in the preparation of a compound of formula (I).

In the processes of the present invention the compound of formula (I) preferably has an enantiomeric excess of greater than about 60%. In another embodiment the enantiomeric excess is greater than about 70%. In another embodiment the enantiomeric excess is greater than about 80%. In another embodiment the enantiomeric excess is greater than about 90%. In another embodiment the enantiomeric excess is greater than about 95%. In another embodiment the enantiomeric excess is greater than about 99%.

In one embodiment compound of formula (I) is enantiomerically enriched by resolution. Any suitable resolving agent may be used, for example tartaric acid based resolving agents, mandelic acid based resolving agents and enzymes.

In one embodiment the enantiomerically enriched compound of formula (I) has an enantiomeric excess of greater than about 90%, more preferably greater than about 95%, more preferably greater then about 99%

EXAMPLES

The following examples are intended to illustrate particular embodiments of the invention, and are not intended to limit the specification, including the claims in any manner.

It will be apparent to those skilled in the art that many modifications, both to the materials and the methods, may be made without departing from the spirit or scope of the invention.

Experimental

Scheme 5

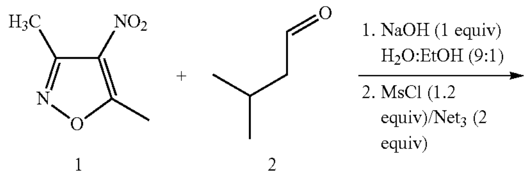

1

2
1.1 equiv.

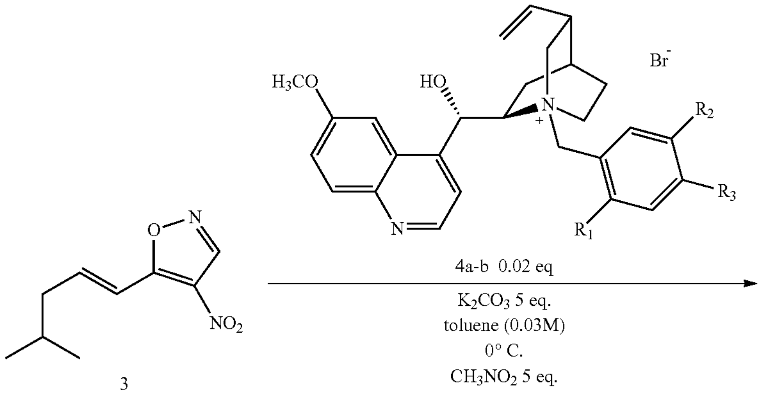

3
90% yield

-continued

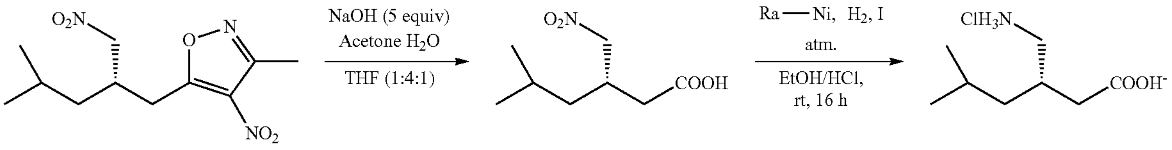

5
96% yield, 76% ee 6
90% yield

7
Quantitative $R_1$ = H, $R_2$ = H, $R_3$ = H 4a
$R_1$ = $NO_2$, $R_2$ = $OCH_3$, $R_3$ = $OCH_3$ 4b Scheme 6

(A)

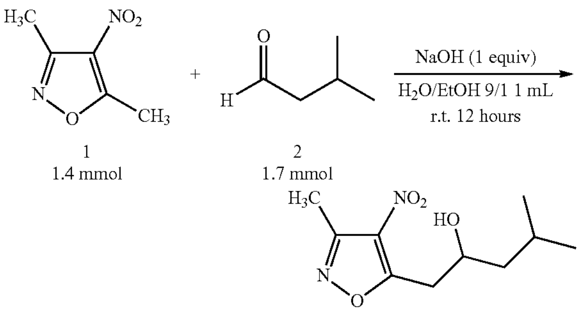

1
1.4 mmol 2
1.7 mmol 8
70% yield (B)

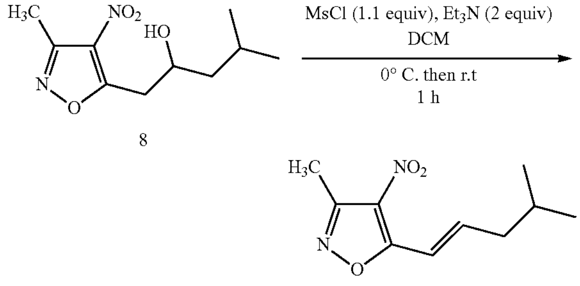

8

3
99% yield

Part A—Preparation of 3-methyl-5-(4-methyl-pent-1-enyl)-4-nitro-isoxazole (8)

In a round bottomed flask fitted with a magnetic stirrer were dissolved 1.4 mmol of 3,5-dimethyl-4-nitroisoxazole 1 (200 mg) in water ethanol mixture (9:1, 0.8 mL). To the clear solution was added NaOH powder (40 mg, 1.4 mmol, 1 equiv). The solution turned deep yellow and was stirred at room temperature for 30 minutes before aldehyde 2 (146 mg, 1.7 mmol) was added in one portion. The reaction mixture was then stirred at room temperature for seven days, then quenched with saturated ammonium chloride and compound 8 extracted with dichloromethane (5 mL). The organic layer was washed with water (3×10 mL) and carried through the next step without further purification (290 mg, 1.26 mmol, 90% yield). Colorless liquid; $R_f$=0.2 (Petroleum Ether/Ethyl Acetate, 90:10); $\delta_H$ (400 MHz, $CDCl_3$) 4.23-4.20 (1H, m), 3.36 (1H, dd, J=15 J=4), 3.29 (1H, dd, J=15 J=7), 2.55 (3H, s), 1.87-1.76 (1H, m), 1.58-1.53 (1H, m), 1.40-1.34 (1H, m), 0.95 (3H, d, J=7), 0.93 (3H, d, J=7); $\delta_c$ (100.6 MHz, $CDCl_3$) 172.9, 155.8, 130.9, 68.0, 46.8, 36.1, 24.8, 23.3, 22.0, 11.8. HRMS: m/z found $[M+H]^+$229.1154, $C_{10}H_{17}N_2O_3$ requires 229.1188.

Part (A) preparation of 4-methyl-1-(3-methyl-4-nitro-isoxazol-5-yl)-pentan-2-ol (8)

In a 1000 mL conical flask fitted with a magnetic follower were put 3,5-dimethyl-4-nitroisoxazole 1 (100 g, Mw=142, 704.2 mmol) and 150 mL of THF and the resulting solution stirred at 0° C. To this solution, were then added 200 mL of MeOH:$H_2O$ (7:3). A freshly made solution of NaOH (5 g, Mw=40, 125 mmol) in 50 mL of $H_2O$ was then charged in a dropping funnel and added drop wise over 10 minutes. Upon this addition, the solution becomes yellow to dark brown. It was noted the formation of a precipitate of sodium 3,5-dimethyl-4-nitroisoxazolate that will dissolve during the course of the reaction. At this point, a solution of isovaleraldehyde 2 (151 g, Mw=86, 1755 mmol, 2.5 equiv.) in 100 mL of THF was added drop wise at 0° C. over the period of 50 min. After this period the ice bath was removed and the reaction allowed reaching room temperature under vigorous stirring. Conversion was monitored after 2 h (60%), 3 h (83%), 3 h30 min (92%) since end of addition of aldehyde. A sample of the reaction mixture was kept under stirring for further two hours and conversion measured again (92%) indicating the reaction mixture had reached the equilibrium. The reaction was quenched with distilled $H_2O$ (500 mL), stirred for 10 minutes, then extracted twice with DCM (300 mL+200 mL). The organic layers were combined, washed with $H_2O$ (300 mL at least to avoid formation of emulsion), then with sat $NaHSO_3$ (200 mL) then again with $H_2O$ (300 mL). The organic layer was evaporated at the rotavapor (49° C., 44 mb) to give 161 g of material which contains the title compound alongside 7% of alkene 3, 8% of 3,5-dimethyl-4-nitroisoxazole and 5% of isovaleraldehyde. Estimated weight in title alcohol was 146 g (91% yield). Colorless liquid; $R_f$=0.2 (Petroleum Ether/Ethyl Acetate, 90:10); $\delta_H$ (400 MHz, $CDCl_3$) 4.23-4.20 (1H, m), 3.36 (1H, dd, J=15 J=4), 3.29 (1H, dd, J=15 J=7), 2.55 (3H, s), 1.87-1.76 (1H, m), 1.58-1.53 (1H, m), 1.40-1.34 (1H, m), 0.95 (3H, d, J=7), 0.93 (3H, d, J=7); $\delta_c$ (100.6 MHz, $CDCl_3$) 172.9, 155.8, 130.9, 68.0, 46.8, 36.1, 24.8, 23.3, 22.0, 11.8. HRMS: m/z found $[M+H]^+$229.1154, $C_{10}H_{17}N_2O_3$ requires 229.1188.

Part (B) preparation of 3-methyl-5-(4-methyl-pent-1-enyl)-4-nitro-isoxazole (3)

To a solution of alcohol 8 (39 mg, 0.17 mmol) in dichloromethane (1 mL) kept at 0° C. by an ice-water bath was added methanesulfonyl chloride (30 mg, 0.20 mmol, 1.2 equiv) and then triethylamine (34.4 mg, 0.34 mmol, 2 equiv). The reaction was allowed to reach room temperature and then stirred for 1 hour. Then the reaction mixture was quenched with water (2 mL), the organic layer was extracted with dichloromethane (3×3 mL), washed with brine, dried over anhydrous $Na_2SO_4$ filtered and evaporated to give pure compound 3 (35 mg, 99% yield). Colorless liquid; $R_f$=0.8 (Petroleum Ether/Ethyl Acetate, 90:10); $\delta_H$ (400 MHz, $CDCl_3$) 7.12-7.00 (2H, m), 2.56 (3H, s), 2.29-2.26 (2H, m), 1.89-1.82 (1H, m), 0.97 (6H, d, J=6), $\delta_c$ (100.6 MHz, $CDCl_3$) 167.0, 156.0, 130.1, 115.6, 43.0, 28.3, 22.5, 12.0. HRMS: m/z found $[M]^+$196.0815, $C_9H_{14}N_2O_3$ requires 196.0848.

Part (B) preparation of 3-methyl-5-(4-methyl-pent-1-enyl)-4-nitro-isoxazole (3)

In a 3 L round bottomed flask fitted with an overhead stirrer (to overcome difficult stirring caused by formation of solid $HNEt_3Cl$ through the reaction) were loaded 160 g of 4-methyl-1-(3-methyl-4-nitro-isoxazol-5-yl)-pentan-2-ol 8 (about 90% pure, 144 g, 633 mmol, Mw=229) and 1000 mL of DCM. The solution was cooled at −30° C. by adding liquid nitrogen to a methanol bath, then methanesulfonyl chloride (86.62 g, Mw=114, 760 mmol, 1.2 equiv) was added drop wise in 20 min. To the resulting solution was then added $NEt_3$ (127.9 g, 1266 mmol, Mw=101, 2.0 equiv) drop wise over the period of 1 h15 min while maintaining the temperature between 0° C. and −20° C. After the addition was completed the reaction was allowed to reach room temperature and stirred for 2 h (from the end of addition of $NEt_3$). The reaction was quenched with $H_2O$ (300 mL), washed with additional $H_2O$ (2×500 mL), then with 5% NaOH in water, the organic layer dried over $Na_2SO_4$ and then evaporated under reduced pressure (47° C., 0 mb) to give 163 g of crude product which was thinned with 50 mL of petroleum ether (40-60° C.) and passed through a plug of silica gel (flash type) (10 g) eluting with petroleum ether (40:60) (50 mL) to give 132 g of title compound. Estimated purity of alkene is 92%. Pale yellow liquid; $R_f$=0.8 (Petroleum Ether/Ethyl Acetate, 90:10); $\delta_H$ (400 MHz, $CDCl_3$) 7.12-7.00 (2H, m), 2.56 (3H, s), 2.29-2.26 (2H, m), 1.89-1.82 (1H, m), 0.97 (6H, d, J=6), $\delta_c$ (100.6 MHz, $CDCl_3$) 167.0, 156.0, 130.1, 115.6, 43.0, 28.3, 22.5, 12.0. HRMS: m/z found $[M]^+$196.0815, $C_9H_{14}N_2O_3$ requires 196.0848.

Note 1:

Product 3 was obtained over 99.9% pure via distillation, collecting the fraction boiling over 120° C. at 0.2 mb. The yield was ca 65-70% of pure alkene.

Note 2:

Purification via DMF wash: the alkene 3 may be obtained over 99.9% pure by dissolving it in a DMF:$H_2O$ (20:80) and then extracting with petroleum ether. Typically, 12 g of crude material were dissolved in 10 mL of DMF, then 40 mL of water were added and the resulting yellow solution was extracted with petroleum ether (40:60), (2×50 mL). Optionally, the alkene (20 g) was dissolved in petroleum ether (40:60), (50 mL), then treated with 3 mL of DMF, stirred for 20 minutes, then washed with water (2×50 mL).

Alternative Synthesis of Alkenes 3'

Scheme 7: alternative route to styrylisoxazoles 3'a-d.

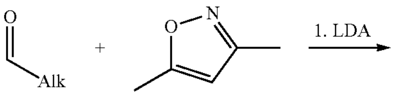

2' 1'

-continued

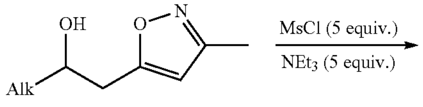

8'

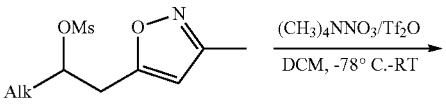

104

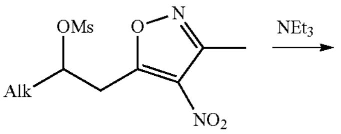

105

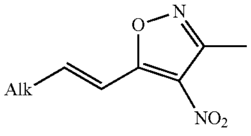

3'

An alternative route to styrylisoxazoles 3'a-d involves reaction of 3,5-dimethylisoxazole 1 with LDA followed by addition of suitable aldehydes 2'a-d. The resulting alcohols 8'a-d were mesylated using MsCl and triethylamine to give compounds 104a-d which in turn was nitrated to 105a-d. Treatment of 105a-d with triethilamine gave desired 3'a-d.

TABLE 1

Isolated yields of hydroxyl isoxazoles 8'a-d

| Entry | Aldehyde | Reactant Alk group | Product | Isolated yield (%) |
|---|---|---|---|---|
| 1 | 2'a | Cyclohexane | 8'a | 74 |
| 2 | 2'b | $CH(CH_2CH_3)CH_2CH_2CH_2CH_3$ | 8'b | 55 |
| 3 | 2'c | $CH_2CH(CH_3)_2$ | 8'c | 70 |
| 4 | 2'd | $CH_2CH_2CH_2CH_2CH_2CH_3$ | 8'd | 64 |

TABLE 2

Isolated yields of mesylated isoxazoles 104a-d

| Entry | Starter | Reactant Alk group | Product | Isolated yield (%) |
|---|---|---|---|---|
| 1 | 8'a | Cyclohexane | 104a | 82 |
| 2 | 8'b | $CH(CH_2CH_3)CH_2CH_2CH_2CH_3$ | 104b | 88 |
| 3 | 8'c | $CH_2CH(CH_3)_2$ | 104c | 85 |
| 4 | 8'd | $CH_2CH_2CH_2CH_2CH_2CH_3$ | 104d | 90 |

TABLE 3

Isolated yields of nitro isoxazoles 105a-d

| | Starter | Reactant Alk | Product | Isolated yield (%) |
|---|---|---|---|---|
| 1 | 104a | Cyclohexane | 105a | 79 |
| 2 | 104b | $CH(CH_2CH_3)CH_2CH_2CH_2CH_3$ | 105b | 75 |
| 3 | 104c | $CH_2CH(CH_3)_2$ | 105c | 70 |
| 4 | 104d | $CH_2CH_2CH_2CH_2CH_2CH_3$ | 105d | 80 |

TABLE 4

| | Starter | Reactant Alk | Product | Isolated yield (%) |
|---|---|---|---|---|
| | | Isolated yields of aliphatic nitro isoxazoles 3'a-d | | |
| 1 | 105a | Cyclohexane | 3'a | 82 |
| 2 | 105b | $CH(CH_2CH_3)CH_2CH_2CH_2CH_3$ | 3'b | 88 |
| 3 | 105c | $CH_2CH(CH_3)_2$ | 3'c | 92 |
| 4 | 105d | $CH_2CH_2CH_2CH_2CH_2CH_3$ | 3'd | 89 |

Typical Procedure for Preparation of Hydroxy Isoxazoles (Compounds 8'a-d)

Under an inert atmosphere, lithium diisopropyl amide (5 ml, 10 mmol) was added dropwise to a stirred solution of isoxazole (1 g, 10 mmol) in anhydrous tetrahydrofuran (10 mL) at −78° C. using a liquid nitrogen/acetone bath. The resulting solution was stirred at the same temperature for 60 minutes. To this solution was then added the aliphatic aldehyde (1 eq, 10 mmol)-78° C. over 60 minutes. The resulting reaction mixture was allowed to warm to room temperature over a period of 2 h, with stirring magnetically. At the end of this time the solvent was evaporated off and the residue re-dissolved in DCM, quenched with saturated aqueous ammonium chloride solution (10 mL) and extracted with DCM (2×20 mL). Combined organic extracts were washed with water followed by brine and dried over anhydrous sodium sulphate before evaporation under reduced pressure. The crude product was purified by column chromatography with 10% ethyl acetate in petroleum spirits as an eluent followed by 20% ethyl acetate in petroleum ether to afford the pure title product.

1-Cyclohexyl-2-(3-methyl-isoxazol-5-yl)-ethanol 8'a

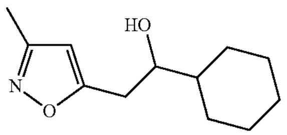

1.5 g, 74% yield, yellow oil, $R_f$=0.4 (30%, EtOAc in Petroleum spirits); $^1$H NMR (400 MHz, $CDCl_3$): $\delta_H$=5.91 (1H, s, C═C—H), 3.61-3.69 (1H, m, $CH_2CH$), 2.84 (1H, dd, J=15, J=4, $CH_2CH$), 2.74 (1H, dd, J=15, J=9, $CH_2CH$), 2.18 (3H, s, $CH_3C$═N), 1.82-1.59 (5H, m, H Aliphatic), 1.35-1.27 (1H, m, H Aliphatic), 1.23-0.93 (5H, m, H Aliphatic); $^{13}$C NMR (100.6 MHz) $\delta_c$=168.1 (C═C—H), 160.0 (N═C—$CH_3$), 103.3, (C═C—H), 73.9 (C—OH), 38.3 (CH-cyclohexane), 34.9 ($CH_2$-aliphatic), 29.1 ($CH_2$-cyclohexane), 27.8 ($CH_2$-cyclohexane), 26.2 ($CH_2$-cyclohexane), 14.0 ($CH_3$-aliphatic), 14.0 ($CH_3$-aliphatic), 11.4 (N═C—$CH_3$), HRMS found: [M−$H^+$] 209.152, $C_{12}H_{18}NO_2$ requires 209.146; m/z: 209 (100%, M−$H^+$).

3-Ethyl-1-(3-methyl-isoxazol-5-yl)-heptan-2-ol 8'b

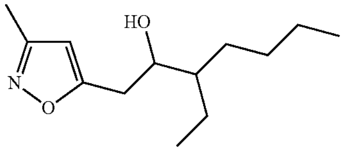 [SMILES: CCCCC(CC)C(O)Cc1cc(C)no1]

1.24 g, 55% yield, yellow oil, $R_f$=0.39 (30%, EtOAc in Petroleum spirits); $^1$H NMR (400 MHz, $CDCl_3$): $\delta_H$=5.91 (1H, s, C═C—H), 3.61-3.69 (1H, m, $CH_2CH$), 2.84 (1H, dd, J=15, J=4, $CH_2CH$), 7.74 (1H, dd, J=15, J=9, $CH_2CH$), 2.18 (3H, s, $CH_3C$═N), 1.82-1.59 (5H, m, H Aliphatic), 1.35-1.27 (1H, m, H Aliphatic), 1.23-0.93 (5H, m, H Aliphatic), 0.92-0.82 (6H, m, $(CH_3)_2$); $^{13}$C NMR (100.6 MHz) $\delta_c$=170.94 (C═C—H), 159.9 (N═C—$CH_3$), 103.0, (C═C—H), 71.4 (C—OH), 46.97 (CH-aliphatic), 44.9 ($CH_2$-aliphatic), 30.6 ($CH_2$-aliphatic), 28.2 ($CH_2$-aliphatic), 23.4 ($CH_2$-aliphatic), 21.3 ($CH_2$-aliphatic), 14.0 ($CH_3$-aliphatic), 14.0 ($CH_3$-aliphatic), 11.7 (N═C—$CH_3$); HRMS found: [M−$H^+$] 225.1733, $C_{13}H_{23}NO_2$ requires 225.1729; m/z: 225 (100%, M−$H^+$).

4-Methyl-1-(3-methyl-isoxazol-5-yl)-pentan-2-ol 8'c

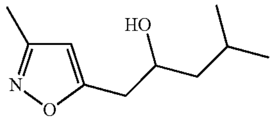

1.28 g, 70% yield, yellow oil, $R_f$=0.4 (30%, EtOAc in petroleum spirits); $^1$H NMR (400 MHz, $CDCl_3$): $\delta_H$=5.92 (1H, s, H isoxazole), 4.06-4.00 (1H, m $CH_2$—CH), 2.87 (1H, dd, J=15, J=4, $CH_2CH$), 2.79 (1H, dd, J=15, J=8, $CH_2CH$), 2.25 (3H, s, N═C—$CH_3$), 1.84-1.74 (1H, m, CH aliphatic), 1.49-1.42 (1H, m, CH aliphatic), 1.30-1.23 (1H, m, CH aliphatic), 0.91 (6H, t, J=7, $CH(CH_3)_2$, 13C NMR (100.6 MHz) $\delta_c$=170.2 (C═C—H), 159.9 (N═C—$CH_3$), 103.2, (C═C—H), 67.95 (C—OH), 46.05 ($CH_2$-aliphatic), 35.4 ($CH_2$-aliphatic), 23.3 ($CH_3$-aliphatic), 21.9 (CH-aliphatic), 11.4 ($CH_3$-aliphatic), 11.4 (N═C—$CH_3$), HRMS found: [M−$H^+$] 183.1262, $C_{10}H_{17}NO_2$ requires 183.1259; m/z: 183 (100%, M−$H^+$).

1-(3-Methyl-isoxazol-5-yl)-octan-2-ol; compound with methane 8'd

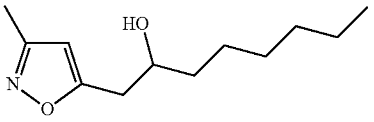

1.35 g, 64% yield, yellow oil, $R_f$=0.42 (30%, EtOAc in petroleum spirits); $^1$H NMR (400 MHz, $CDCl_3$): $\delta_H$=5.87 (1H, s, C═C—H), 3.91-3.85 (1H, m, $CH_2CH$), 2.82 (1H, dd, J=15, J=5, $CH_2CH$), 2.75 (1H, dd, J=15, J=8, $CH_2CH$), 2.18 (3H, s, $CH_3C$═N), 1.46-1.34 (5H, m, H Aliphatic), 1.34-1.21 (5H, m, H Aliphatic), 0.91-0.87 (3H, t, J=6, ($CH_3$); $^{13}$C NMR (100.6 MHz) $\delta_c$=170.94 (C═C—H), 159.9 (N═C—$CH_3$), 104.1, (C═C—H), 80.6 (C—OH), 38.35 ($CH_2$-aliphatic), 34.48 ($CH_2$-aliphatic), 31.7 ($CH_2$-aliphatic), 28.2 ($CH_2$-aliphatic), 25.2 ($CH_2$-aliphatic), 21.3 ( $CH_2$-aliphatic), 14.0 ($CH_3$-aliphatic), 11.4 (N═C—$CH_3$); HRMS found: [M−$H^+$] 211.1564, $C_{12}H_{21}NO_2$ requires 211.1572; m/z: 211 (100%, M−$H^+$).

Typical Procedure for Preparation of Mesylated Isoxazoles (Compounds 104a-d)

Methane sulfonyl chloride (25 mmol, 5 eq) and $Et_3N$ (25 mmol, 5 eq) were sequentially added to a solution of starting alcohol (5 mmol, 1 eq) in DCM (10 ml) at 0° C. The reaction was then brought to room temperature and stirred for a further hour. The mixture was then diluted with water and the organic layer extracted, washed with brine and dried over $MgSO_4$ before evaporation under reduced pressure. The crude product was purified by column chromatography with 2% methanol in DCM as an eluent to afford the pure title product.

Methanesulfonic acid 1-cyclohexyl-2-(3-methyl-isoxazol-5-yl)-ethyl ester 104a

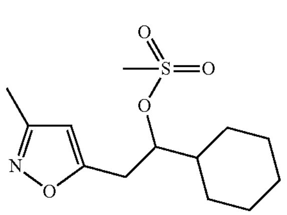 [SMILES: Cc1cc(CC(OS(C)(=O)=O)C2CCCCC2)on1]

1.180 g, 82% yield, yellow oil, $R_f$=0.5 (30%, EtOAc in Petroleum spirits); $^1$H NMR (400 MHz, $CDCl_3$): $\delta_H$=6.00 (1H, s, C═C—H), 4.74 (1H, q, J=5.6, $CH_2CH$), 3.13 (2H, d, J=6, $CH_2CH$), 2.83 (3H, s, SO2CH3), 2.27 (3H, s, $CH_3C$═N), 1.86-1.61 (6H, m, H Aliphatic), 1.29-1.15 (5H, m, H Aliphatic); $^{13}$C NMR (100.6 MHz) $\delta_c$=168.1 (C═C—H), 160.0 (N═C—$CH_3$), 104.4, (C═C—H), 84.50 (C—$OSO_2CH_3$), 41.13 (C—$OSO_2CH_3$), 38.3 (CH-cyclohexane), 37.7 ($CH_2$-aliphatic), 29.3 ($CH_2$-cyclohexane), 28.3 ($CH_2$-cyclohexane), 25.8 ($CH_2$-cyclohexane), 11.4 (N═C—$CH_3$); HRMS found: [M−H$^+$] 287.1195, $C_{13}H_{21}NO_4S$ requires 287.1191; m/z: 287 (100%, M−H$^+$).

Methanesulfonic acid 2-ethyl-1-(3-methyl-isoxazol-5-ylmethyl)-hexyl ester 104b

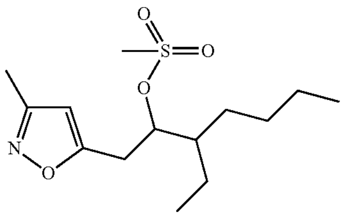 [SMILES: CCCCC(CC)C(Cc1cc(C)no1)OS(C)(=O)=O]

1.33 g, 88% yield, yellow oil, $R_f$=0.52 (30%, EtOAc in petroleum spirits); $^1$H NMR (400 MHz, $CDCl_3$): $\delta_H$=5.97 (1H, s, C═C—H), 4.95-4.90 (1H, m, $CH_2CH$), 3.04 (2H, d, J=6, $CH_2CH$), 2.75 (3H, s, $SO_2CH_3$), 2.21 (3H, s, C═C—$CH_3$), 1.65-1.58 (1H, m, CH aliphatic), 1.58-1.24 (8H, m, $(CH_2)_4$ aliphatic), 0.92-0.82 (6H, m, $(CH_3)_2$), $^{13}$C NMR (100.6 MHz) $\delta_c$=170.94 (C═C—H), 159.9 (N═C—$CH_3$), 103.0, (C═C—H), 82.6 (C—$OSO_2CH_3$), 46.76 (CH-aliphatic), 43.3 ($CH_2$-aliphatic), 38.3 ($SO_2CH_3$), 31.5 ($CH_2$-aliphatic), 28.2 ($CH_2$-aliphatic), 25.2 ($CH_2$-aliphatic), 21.3 ($CH_2$-aliphatic), 14.0 ($CH_3$-aliphatic), 14.0 ($CH_3$-aliphatic), 11.7 (N═C—$CH_3$) HRMS found: [M−H$^+$] 303.1512, $C_{14}H_{25}NO_4S$ requires 303.1504; m/z: 303 (100%, M−H$^+$).

Methanesulfonic acid 3-methyl-1-(3-methyl-isoxazol-5-ylmethyl)-butyl ester 104c

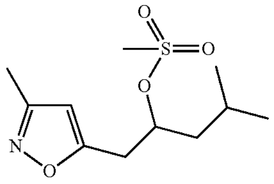 [SMILES: Cc1cc(CC(CC(C)C)OS(C)(=O)=O)on1]

1.11 g, 85% yield, yellow oil, $R_f$=0.48 (30%, EtOAc in petroleum spirits); $^1$H NMR (400 MHz, $CDCl_3$): $\delta_H$=5.95 (1H, s, H isoxazole), 4.97-4.92 (1H, m), 3.12 (1H, dd, J=16, J=5, $CH_2CH$), 3.03 (1H, dd, J=16, J=6, $CH_2CH$), 2.81 (3H, s, $SO_2CH_3$), 2.21 (3H, s, N═C—$CH_3$), 1.73-1.61 (2H, m, $CH_2$ aliphatic), 1.42-1.38 (1H, m CH aliphatic), 0.89 (6H, t, J=7, $CH(CH_3)_2$), 13C NMR (100.6 MHz) $\delta_c$=170.1 (C═C—H), 158.2 (N═C—$CH_3$), 103.2, (C═C—H), 68.0 (C—$OSO_2CH_3$), 46.1 ($CH_2$-aliphatic), 34.6 ($CH_2$-aliphatic), 34.2 ($SO_2CH_3$), 24.4 ($CH_3$-aliphatic), 23.9 ($CH_3$-aliphatic), 22.3 (CH-aliphatic), 12.5 (N═C—$CH_3$), HRMS found: [M−H$^+$] 261.1039, $C_{11}H_{19}NO_4S$ requires 261.1035; m/z: 261 (100%, M−H$^+$).

Methanesulfonic acid 1-(3-methyl-isoxazol-5-ylmethyl)-heptyl ester 104d

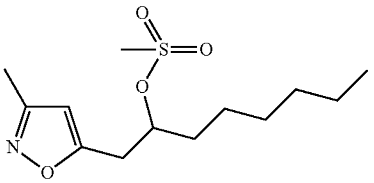 [SMILES: CCCCCCC(Cc1cc(C)no1)OS(C)(=O)=O]

1.3 g, 90% yield, yellow oil, $R_f$=0.5 (30%, EtOAc in petroleum spirits); $^1$H NMR (400 MHz, $CDCl_3$): $\delta_H$=6.02 (1H, s, C═C—H), 4.97-4.91 (1H, m, $CH_2CH$), 3.15 (2H, dd, J=5, J=3, $CH_2CH$), 2.89 (3H, s, $SO_2CH_3$), 2.29 (3H, s, C═C—$CH_3$), 1.82-1.66 (2H, m, $CH_2$ aliphatic), 1.48-1.24 (8H, m, $(CH_2)_4$ aliphatic), 0.91-0.87 (3H, t, J=6, ($CH_3$), $^{13}$C NMR (100.6 MHz) $\delta_c$=170.94 (C═C—H), 159.9 (N═C—$CH_3$), 104.1, (C═C—H), 80.6 (C—$OSO_2CH_3$), 38.35 ($SO_2CH_3$), 34.48 ($CH_2$-aliphatic), 31.7 ($CH_2$-aliphatic), 28.2 ($CH_2$-aliphatic), 25.2 ($CH_2$-aliphatic), 24.2 ($CH_2$-aliphatic), 21.3 ($CH_2$-aliphatic), 14.0 ($CH_3$-aliphatic), 11.4 (N═C—$CH_3$); HRMS found: [M−H$^+$] 289.1350, $C_{13}H_{23}NO_4S$ requires 289.1348; m/z: 289 (100%, M−H$^+$).

Typical Procedure for Preparation of Nitro Isoxazoles (Compounds 105a-d)

Under a $N_2$ gas blanket at room temperature, triflic anhydride (2 mmol, 2 eq) was added dropwise to a stirred suspension of tetra methyl ammonium nitrate (2 mmol, 2 eq) in 2 ml of anhydrous DCM, a slight temperature rise was observed. After stirring for at least 1.5 hours at room temperature, the stirred suspension was cooled to −78° C. using an acetone/liquid nitrogen bath. The aliphatic isoxazole (1 mmol, 1 eq) was dissolved in 3 ml of anhydrous DCM and subsequently added to the stirred nitronium triflate suspension keeping the temperature at −65° C. or lower. The reaction suspension was kept under $N_2$, the cooling bath removed and the reaction was stirred at room temperature for 24 hours.

The reaction was quenched using $NaHCO_3$ to give an aqueous layer of PH 8, the lower DCM layer was then separated and washed with 5×20 ml of water. The combined water washes were back extracted with 2×20 ml of DCM. The combined DCM portions were then dried over $MgSO_4$. DCM removal by rotary evaporation gave the crude product. The crude product was purified by column chromatography starting with 10% EtOAc in petroleum spirits as the eluent followed by 20% EtOAc in petroleum spirits to give the pure product.

Methanesulfonic acid 1-cyclohexyl-2-(3-methyl-4-nitro-isoxazol-5-yl)-ethyl ester 105a

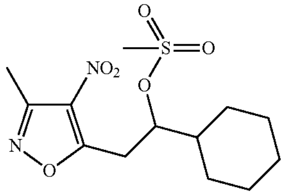 [SMILES: Cc1noc(CC(OS(C)(=O)=O)C2CCCCC2)c1[N+](=O)[O-]]

0.26 g, 79% yield, yellow oil; $R_f$=0.65 (30%, EtOAc in Petroleum spirits); $^1$H NMR (400 MHz, $CDCl_3$): $\delta_H$=4.97 (1H, m, $CH_2C\underline{H}$), 3.60 (1H, dd, J=15, J=4, $C\underline{H}_2CH$), 3.47 (1H, dd, J=15, J=9, $C\underline{H}_2CH$), 2.91 (3H, s, $SO_2C\underline{H}_3$), 2.57 (3H, s, $C\underline{H}_3C{=}N$), 1.90-1.70 (6H, m, $\underline{H}$ Aliphatic), 1.30-1.18 (5H, m, $\underline{H}$ Aliphatic); $^{13}$C NMR (100.6 MHz) $\delta_c$=170.9 ($\underline{C}{=}C{-}NO_2$), 155.9 ($N{=}\underline{C}{-}CH_3$), 110.9, ($C{=}\underline{C}{-}NO_2$), 81.90 ($\underline{C}{-}OSO_2CH_3$), 42.3 ($C{-}OSO_2\underline{C}H_3$), 38.5 ($\underline{C}$H-cyclohexane), 31.54 ($\underline{C}H_2$-aliphatic), 30.7 ($\underline{C}H_2$-cyclohexane), 28.1 ($\underline{C}H_2$-cyclohexane), 25.8 ($\underline{C}H_2$-cyclohexane), 11.6 ($N{=}C{-}\underline{C}H_3$); HRMS found: [M−$H^+$] 332.1035, $C_{13}H_{20}N_2O_6S$ requires 332.1042; m/z: 332 (100%, M−$H^+$).

Methanesulfonic acid 2-ethyl-1-(3-methyl-4-nitro-isoxazol-5-ylmethyl)-hexyl ester 105b

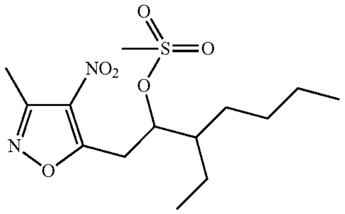 [SMILES: CCCCC(CC)C(Cc1onc(C)c1[N+](=O)[O-])OS(C)(=O)=O]

0.26 g, 75% yield, yellow oil, $R_f$=0.62 (30%, EtOAc in petroleum spirits); $^1$H NMR (400 MHz, $CDCl_3$): $\delta_H$=5.20-5.16 (1H, m, $CH_2C\underline{H}$), 3.48 (2H, d, J=6, $C\underline{H}_2CH$), 2.88 (3H, s, $SO_2C\underline{H}_3$), 2.55 (3H, s, $C{=}C{-}C\underline{H}_3$), 1.65-1.58 (1H, m, C$\underline{H}$ aliphatic), 1.58-1.24 (8H, m, $(C\underline{H}_2)_4$ aliphatic), 0.92-0.82 (6H, m, $(C\underline{H}_3)_2$), $^{13}$C NMR (100.6 MHz) $\delta_c$=171.05 ($\underline{C}{=}C{-}H$), 155.9 ($N{=}\underline{C}{-}CH_3$), 103.0, ($C{=}\underline{C}{-}NO_2$), 79.9 ($\underline{C}{-}OSO_2CH_3$), 44.5 ($\underline{C}$H-aliphatic), 38.3 ($SO_2CH_3$), 31.54 ($\underline{C}H_2$-aliphatic), 29.9 ($\underline{C}H_2$-aliphatic), 29.4 ($\underline{C}H_2$-aliphatic), 28.57 ($\underline{C}H_2$-aliphatic), 22.8 ( $\underline{C}H_2$-aliphatic), 14.0 ($\underline{C}H_3$-aliphatic), 14.0 ($\underline{C}H_3$-aliphatic), 11.8 ($N{=}C{-}\underline{C}H_3$) HRMS found: [M−$H^+$] 348.1360, $C_{14}H_{24}N_2O_6S$ requires 348.1355; m/z: 348 (100%, M−$H^+$).

Methanesulfonic acid 3-methyl-1-(3-methyl-4-nitro-isoxazol-5-ylmethyl)-butyl ester 105c

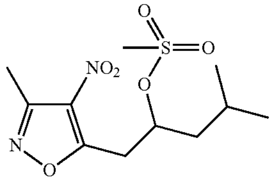 [SMILES: Cc1noc(CC(CC(C)C)OS(C)(=O)=O)c1[N+](=O)[O-]]

0.21 g, 70% yield, yellow oil, $R_f$=0.67 (30%, EtOAc in petroleum spirits); $^1$H NMR (400 MHz, $CDCl_3$): $\delta_H$=5.23-5.17 (1H, m), 3.62 (1H, dd, J=15, J=4, $C\underline{H}_2CH$), 3.50 (1H, dd, J=15, J=8, $C\underline{H}_2CH$), 2.95 (3H, s, $SO_2C\underline{H}_3$), 2.58 (3H, s, $N{=}C{-}CH_3$), 1.84-1.75 (2H, m, $CH_2$ aliphatic), 1.57-1.49 (1H, m CH aliphatic), 0.99 (6H, t, J=7, $CH(C\underline{H}_3)_2$), 13C NMR (100.6 MHz) $\delta_c$=170.1 ($\underline{C}{=}C{-}H$), 158.2 ($N{=}\underline{C}{-}CH_3$), 103.2, ($C{=}\underline{C}{-}NO_2$), 68.0 ($\underline{C}{-}OSO_2CH_3$), 46.1 ($\underline{C}H_2$-aliphatic), 34.2 ($SO_2C\underline{H}_3$), 26.0 ($\underline{C}H_2$-aliphatic), 24.4 ($\underline{C}H_3$-aliphatic), 23.9 ($\underline{C}H_3$-aliphatic), 22.3 ($C\underline{H}$-aliphatic), 12.5 ($N{=}C{-}\underline{C}H_3$), HRMS found: [M−$H^+$] 306.0387, $C_{11}H_{18}N_2O_6S$ requires 306.0386; m/z: 306 (100%, M−$H^+$).

Methanesulfonic acid 1-(3-methyl-4-nitro-isoxazol-5-ylmethyl)-heptyl ester 105d

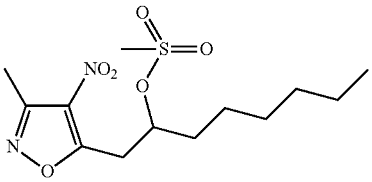 [SMILES: CCCCCCC(Cc1onc(C)c1[N+](=O)[O-])OS(C)(=O)=O]

0.27 g, 80% yield, yellow oil, $R_f$=0.6 (30%, EtOAc in petroleum spirits); $^1$H NMR (400 MHz, $CDCl_3$): $\delta_H$=5.06-5.01 (1H, m, $CH_2C\underline{H}$), 3.54 (1H, dd, J=15, J=4, $C\underline{H}_2CH$), 3.50 (1H, dd, J=15, J=8, $C\underline{H}_2CH$), 2.89 (3H, s, $SO_2C\underline{H}_3$), 2.51 (3H, s, $C{=}C{-}C\underline{H}_3$), 1.82-1.66 (2H, m, $C\underline{H}_2$ aliphatic), 1.48-1.24 (8H, m, $(C\underline{H}_2)_4$ aliphatic), 0.89 (3H, t, J=6, $(C\underline{H}_3)$, $^{13}$C NMR (100.6 MHz) $\delta_c$=170.19 ($\underline{C}{=}C{-}H$), 155.82 ($N{=}\underline{C}{-}CH_3$), 102.21, ($C{=}\underline{C}{-}NO_2$), 78.05 ($\underline{C}{-}OSO_2CH_3$), 38.35 ($SO_2CH_3$), 34.48 ($\underline{C}H_2$-aliphatic), 31.7 ($\underline{C}H_2$-aliphatic), 29.6 ($\underline{C}H_2$-aliphatic), 28.2 ($\underline{C}H_2$-aliphatic), 25.2 ($\underline{C}H_2$-aliphatic), 22.50 ($\underline{C}H_2$-aliphatic), 14.0 ($\underline{C}H_3$-aliphatic), 11.81 ($N{=}C{-}\underline{C}H_3$); HRMS found: [M−$H^+$] 334.1203, $C_{13}H_{22}N_2O_6S$ requires 334.1199; m/z: 334 (100%, M−$H^+$).

Typical Procedure for Preparation of Aliphatic Styrlisoxazoles (Compounds 3'a-d)

$Et_3N$ (2.5 mmol, 2.5 eq) was added to nitro styryl isoxazole (1 mmol, 1.0 eq) in DCM (15 ml) and stirred at room temperature for approximately 1 hour. The reaction mixture was then quenched with $NH_4Cl$ and diluted with water (10 mL). The organic layer was separated and dried over $Na_2SO_4$, filtered and evaporated to yield the crude compound. The crude product was purified by column chromatography using 100% DCM as the eluent.

5-(2-Cyclohexyl-vinyl)-3-methyl-4-nitro-isoxazole 3'a

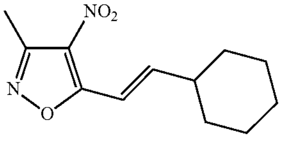 [SMILES: Cc1noc(/C=C/C2CCCCC2)c1[N+](=O)[O-]]

0.19 g, 82% yield, yellow oil; $R_f$=0.75 (20%, EtOAc in Petroleum spirits); $^1$H NMR (400 MHz, $CDCl_3$): $\delta_H$=6.97 (1H, dd, J=16, J=6, CH═CH), 6.91 (1H, d, J=16, CH═CH), 2.49 (3H, s, $CH_3C$═N), 2.26-2.23 (1H, m, CH Aliphatic), 1.80-1.62 (5H, m, H Aliphatic), 1.34-1.11 (5H, m, H Aliphatic); $^{13}$C NMR (100.6 MHz) $\delta_c$=170.8 (C═C—$NO_2$), 156.0 (N═C—$CH_3$), 111.1, (C═C—$NO_2$), 138.2 (C═C), 129.5 (C═C), 35.0 (CH-cyclohexane), 31.5 ($CH_2$-cyclohexane), 27.5 ($CH_2$-cyclohexane), 25.0 ($CH_2$-cyclohexane), 11.4 (N═C—$CH_3$); HRMS found: [M−$H^+$] 236.1161, $C_{12}H_{16}N_2O_3$ requires 236.1161; m/z: 236 (100%, M−$H^+$).

5-(3-Ethyl-hept-1-enyl)-3-methyl-4-nitro-isoxazole 3'b

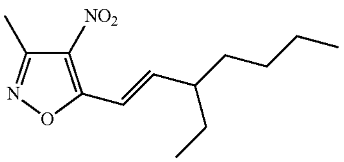 [SMILES: CCCCC(/C=C/c1onc(C)c1[N+](=O)[O-])CC]

0.22 g, 88% yield, yellow oil, $R_f$=0.77 (20%, EtOAc in petroleum spirits); $^1$H NMR (400 MHz, $CDCl_3$): $\delta_H$=6.94 (1H, d, J=16, CH═CH), 6.80 (1H, dd, J=16, J=9, CH═CH), 2.49 (3H, s, N═C—$CH_3$) 1.65-1.58 (1H, m, CH aliphatic), 1.58-1.24 (8H, m, $(CH_2)_4$ aliphatic), 0.92-0.82 (6H, m, $(CH_3)_2$), $^{13}$C NMR (100.6 MHz) $\delta_c$=171.05 (C═C—H), 155.9 (N═C—$CH_3$), 103.0, (C═C—$NO_2$), 135.6 (CH═CH), 136.9 (CH═CH), 40.3 (CH aliphatic), 31.54 ($CH_2$-aliphatic), 29.4 ($CH_2$-aliphatic), 28.57 ($CH_2$-aliphatic), 22.8 ($CH_2$-aliphatic), 14.0 ($CH_3$-aliphatic), 14.0 ($CH_3$-aliphatic), 11.8 (N═C—$CH_3$) HRMS found: [M−$H^+$] 252.1462, $C_{13}H_{20}N_2O_3$ requires 252.1474; m/z: 252 (100%, M−$H^+$).

3-Methyl-5-(4-methyl-pent-1-enyl)-4-nitro-isoxazole 3'c

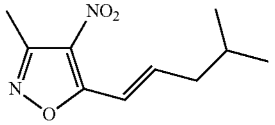

0.19 g, 92% yield, yellow oil, $R_f$=0.71 (20%, EtOAc in petroleum spirits); $^1$H NMR (400 MHz, $CDCl_3$): $\delta_H$=7.08 (1H, dd, J=16, J=6, CH═CH), 7.03 (1H, dd, J=21, J=16, CH═CH), 2.53 (3H, s, N═C—$CH_3$), 2.26 (2H, t, J=6, $CH_2$ aliphatic), 1.89-1.79 (1H, m CH aliphatic), 0.95 (6H, d, J=7, $CH(CH_3)_2$), $^{13}$C NMR (100.6 MHz) $\delta_c$=170.1 (C═C—H), 158.2 (N═C—$CH_3$), 133.0 (CH═CH), 127.0 (CH═CH), 103.2, (C═C—$NO_2$), 42.1 ($CH_2$-aliphatic), 24.4 ($CH_3$-aliphatic), 23.9 ($CH_3$-aliphatic), 22.3 (CH-aliphatic), 12.5 (N═C—$CH_3$), HRMS found: [M−$H^+$] 210.1008, $C_{10}H_{14}N_2O_3$ requires 210.1004; m/z: 210 (100%, M−$H^+$)

3-Methyl-4-nitro-5-oct-1-enyl-isoxazole 3'd

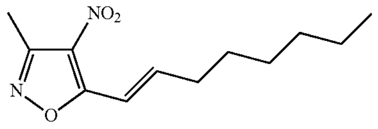 [SMILES: CCCCCC/C=C/c1onc(C)c1[N+](=O)[O-]]

0.21 g, 89% yield, yellow oil, $R_f$=0.75 (20%, EtOAc in petroleum spirits); $^1$H NMR (400 MHz, $CDCl_3$): $\delta_H$=7.10 (1H, dd, J=16, J=6, CH═CH), 7.06 (1H, dd, J=26, J=16, CH═CH), 2.54 (3H, s, C═C—$CH_3$), 2.38 (2H, q, J=6, $CH_2$ aliphatic), 1.57-1.50 (2H, m, $CH_2$ aliphatic), 1.37-1.28 (6H, m, $(CH_2)_3$), 0.89 (3H, t, J=6, $(CH_3)$, $^{13}$C NMR (100.6 MHz) $\delta_c$=170.19 (C═C—H), 155.82 (N═C—$CH_3$), 135.6 (CH═CH), 126.9 (CH═CH), 102.21, (C═C—$NO_2$), 34.48 ($CH_2$-aliphatic), 31.7 ($CH_2$-aliphatic), 28.2 ($CH_2$-aliphatic), 25.2 ($CH_2$-aliphatic), 22.50 ($CH_2$-aliphatic), 14.0 ($CH_3$-aliphatic), 11.81 (N═C—$CH_3$); HRMS found: [M−$H^+$] 238.1302, $C_{12}H_{18}N_2O_3$ requires 238.1317; m/z: 238 (100%, M−$H^+$).

Procedure for the preparation of 3-methyl-5-(4-methyl-2-nitromethyl-pentyl)-4-nitro-isoxazole (5)

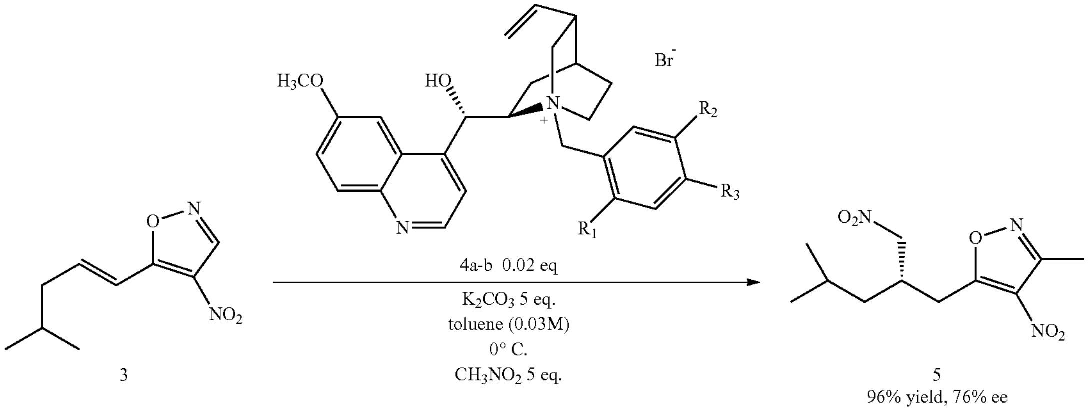

3

5

96% yield, 76% ee $R_1$ = H, $R_2$ = H, $R_3$ = H 4a $R_1$ = $NO_2$, $R_2$ = $OCH_3$, $R_3$ = $OCH_3$ 4b Procedure A:

In a round bottomed flask, fitted with a magnetic stirrer were sequentially added compound 3 (196 mg, 1 mmol) toluene (33 mL), N-benzyl-quinidinium bromide 4a(R═H) (23 mg, 0.05 equiv, 5 mol %), and nitromethane (300 mg, 5 mmol, 5 equiv). Finally, $K_2CO_3$ (690 mg, 5 mmol, 1 equiv) was added in one portion. The reaction was stirred at 0° C. for 60 hours, then quenched with sat $NH_4Cl$ (10 mL), extracted with toluene (2×10 mL), dried over $MgSO_4$, filtered over celite and evaporated to give pure compound 5 in 96% yield and 65% ee.

Procedure B

In a round bottomed flask, fitted with a magnetic stirrer were sequentially added compound 3 (196 mg, 1 mmol) toluene (33 mL), N-(4,5-dimethoxybenzyl-2-nitrobenzyl) quinidinium bromide 4b ($R═R_1═NO_2$, $R_2═OCH_3$, $R_3═OCH_3$) (12 mg, 0.02 equiv, 2 mol %), and nitromethane (300 mg, 5 mmol, 5 equiv). Finally, $K_2CO_3$ (690 mg, 5 mmol, 1 equiv) was added in one portion. The reaction was stirred at 0° C. for 24 hours, then quenched with sat $NH_4Cl$ (10 mL), extracted with toluene (2×10 mL), dried over $MgSO_4$, filtered over celite and evaporated to give pure compound 5 in 96% yield and 76% ee.

Compound 5: Colorless liquid; $R_f$=0.2 (Petroleum Ether/Ethyl Acetate, 90:10); $\delta_H$ (400 MHz, $CDCl_3$) 4.38 (2H, d, J=6), 3.35 (1H, dd, J=15, J=6), 3.28 (1H, dd, J=15, J=7), 2.87 (1H, sept, J=7), 2.56 (3H, s), 1.68 (1H, sept, J=7), 1.36-1.23 (2H, m), 0.92 (3H, d, J=4), 0.90 (3H, d, J=4), $\delta_c$ (100.6 MHz, $CDCl_3$) 172.1, 122.9, 78.5, 40.9, 33.9, 30.0, 25.1, 22.4, 22.3, 11.7. HRMS: m/z found $[M+H]^+$272.1212, $C_{11}H_{18}N_3O_5$ requires 272.1212.

Recrystallisation of compound 5 from 68-86% ee to enantiopure +99ee:

Purified compound 5 (4 g) was dissolved in minimum amounts of hot isopropanol or hot mixtures of isopropanol hexane (1:1), which were typically 3-10 mL. The resulting solution was cooled at −20° C. to give compound 5 as needles, which were filtered, dried weighted 2.5-3.2 g.

Procedure C:

In a round bottomed flask, fitted with a magnetic stirrer were sequentially added alkene 3 (20 mg, 0.096 mmol) toluene (9.6 mL), catalyst A-E (see below) (0.1 equiv, 10 mol %), and nitromethane (30 mg, 0.48 mmol, 5 equiv). The temperature was made 0° C. using an ice water bath, then $K_2CO_3$ (66 mg, 0.48 mmol, 5 equiv) was added in one portion. The reaction was stirred at 0-3° C. for 32 hours, then quenched with sat $NH_4Cl$ (10 mL), extracted with toluene (2×10 mL), dried over $MgSO_4$, filtered over celite and evaporated to give pure compound in yield and ee listed in table 1.

TABLE 1 catalyst screening

| entry | Catalyst | Conv % of 3 | Yield % of 5 | ee % of 5 |
|---|---|---|---|---|
| 1 | A | 100 | 95 | 72 |
| 2 | B | 100 | 97 | 86 |
| 3 | C | 100 | 96 | 85 |
| 4 | D | 100 | 97 | 64 |
| 5 | E | 100 | 91 | 62 |

Procedure D:

In a round bottomed flask, fitted with a magnetic stirrer were sequentially added alkene 3 and toluene as indicated in table 2, catalyst B (0.05 equiv, 5 mol %) and nitromethane (3-5 equiv). The temperature was made 0° C. using an ice water bath, then $K_2CO_3$ (3-5 equiv) was added in one portion. The reaction was stirred at 0-3° C. for time indicated in table 2, then quenched with sat $NH_4Cl$, extracted with toluene, dried over $MgSO_4$, filtered over celite and evaporated to give pure compound in yield and ee as listed in table 2.

TABLE 2

| Entry | $CH_3NO_2$ | $K_2CO_3$ | Alkene 3 (mmol) | Alkene 3(mg) | Conc. (M) | Toluene (mL) | Conv. % of 3 | Ee % of 5 |
|---|---|---|---|---|---|---|---|---|
| 1 | 5 | 5 | 0.096 | 20 | 0.01M | 9.6 | 89% (96 h) | 86% |
| 2 | 1.5 | 5 | 10 | 2100 | 0.08M | 125 | 30% (96 h) | 81% |
| 3 | 1.5 | 5 | 10 | 2100 | 0.16M | 62.5 | 41% (96 h) | 79% |
| 4 | 1.5 | 5 | 2.4 | 500 | 0.04M | 60 | 20% (24 h) | 81% |
| 5 | 5 | 5 | 2.4 (p)[a] | 500 | 0.04M | 60 | 75% (40 h) | 85% |
| 6 | 5 | 5 | 2.4 (p)[a] | 500 | 0.08M | 30 | 80% (20 h) | 83% |
| 7 | 5 | 5 | 2.4 (p)[a] | 500 | 0.16M | 15 | 83% (20 h) | 80% |
| 8 | 5 | 5 | 2.4 (p)[a] | 500 | 0.32M | 7.5 | 92% (19 h) | 74% |
| 9 | 3 | 3 | 2.4 (p)[a] | 500 | 0.16M | 15 | 57% (17 h) | 80% |
| 10 | 3 | 3 | 1.7 (p)[a] | 500 | 0.32M | 5.3 | 75% (17 h) | 74% |

[a](p) refers to alkene 3 over 98% pure.

Procedure E:

In a round bottomed flask, fitted with a magnetic stirrer were sequentially added alkene 3 (25 g, 119 mmol) and toluene (750 ml), then catalyst B (3.6 g, 0.05 equiv, 5 mol %) and nitromethane (36.3 g, 595 mmol, 5 equiv). The temperature was made 0° C. using an ice water bath, then $K_2CO_3$ (82 g, 595 mmol, 5 equiv) was added in one portion. The reaction was stirred at 0-3° C. for 30 hours, then quenched water (250 mL), the organic layer separated and the aqueous treated with diluted HCl to pH ~3; the aqueous layer was extracted with toluene (2×50 mL); the organic layer were combined, evaporated and the residue passed through a plug of silica eluting with DCM. The product was obtained in 93% yield (30 g) as a sticky liquid and in 80% ee. Compound 5: Colorless solid, mp=43° C. (isopropanol Hexane 1:1); $R_f$=0.2 (Petroleum Ether/Ethyl Acetate, 90:10); $□_H$ (400 MHz, $CDCl_3$) 4.38 (2H, d, J=6), 3.35 (1H, dd, J=15, J=6), 3.28 (1H, dd, J=15, J=7), 2.87 (1H, sept, J=7), 2.56 (3H, s), 1.68 (1H, sept, J=7), 1.36-1.23 (2H, m), 0.92 (3H, d, J=4), 0.90 (3H, d, J=4), $□_c$ (100.6 MHz, $CDCl_3$) 172.1, 122.9, 78.5, 40.9, 33.9, 30.0, 25.1, 22.4, 22.3, 11.7. HRMS: m/z found $[M+H]^+$272.1212, $C_{11}H_{18}N_3O_5$ requires 272.1246.

Procedure F:

In a round bottomed flask, fitted with an overhead stirrer were charged toluene (330 mL) and $K_2CO_3$ (75.9 g, 550 mmol, 2.5 equiv). A solution of alkene 3 (46.2 g, 220 mmol), nitromethane (26.8 g, 440 mmol, 2 equiv) and catalyst B (5.33 g, 0.04 equiv, 4 mol %) in toluene (110 mL) was charged in a dropping funnel and added drop wise over a 2 h period. The reaction was stirred at room temperature (21° C.) for 28 h, then quenched with water (500 mL) and the organic layer separated. The aqueous layer was treated with HCl conc to pH ~3; the aqueous layer was extracted with toluene (2×100 mL); the organic layer were combined, evaporated and the residue passed through a plug of silica eluting with DCM. The product was obtained in 92% yield (54.8 g) as a sticky liquid and in 68% ee.

NOTE 1: the reaction may have a induction period depending on purity of alkene 3.

NOTE 2: the reaction carried out by adding the solution of alkene/nitromethane/catalyst over a period of 16 hours gave only 16% conversion in the same time.

Procedure G (Preparation of Racemic Compound 5):

In a round bottomed flask, fitted with an overhead stirrer were charged toluene (330 mL) and $K_2CO_3$ (75.9 g, 550 mmol, 2.5 equiv). A solution of alkene 3 (46.2 g, 220 mmol), nitromethane (26.8 g, 440 mmol, 2 equiv) and N-tetrabutyl ammonium bromide (2.82 g, 0.04 equiv, 4 mol %) in toluene (110 mL) was charged in a dropping funnel and added drop wise over a 2 h period. The reaction was stirred at room temperature (21° C.) for 28 h, then quenched with water (500 mL) and the organic layer separated. The aqueous layer was treated with HCl conc to pH ~3; the aqueous layer was extracted with toluene (2×100 mL); the organic layer were combined, evaporated and the residue passed through a plug of silica eluting with DCM. The product was obtained in 94% yield (56 g) as a sticky liquid.

-continued

I

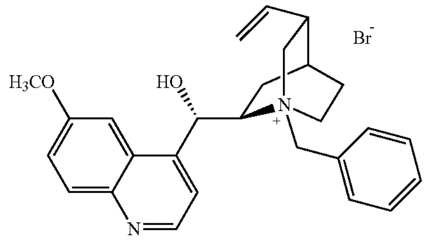

N-benzylquinidinium bromide

II

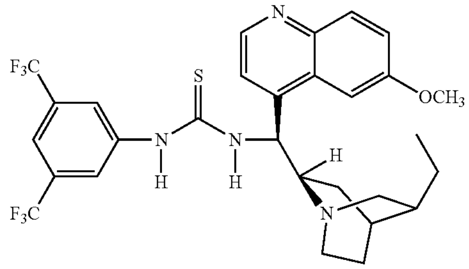

1-(3,5-Bis-trifluoromethyl-phenyl)-3-[(5-ethyl-1-aza-bicyclo[2.2.2]oct-2-yl)-(6-methoxy-quinolin-4-yl)-methyl]-thiourea

TABLE 11

| entry | B (equiv) | Solvent | Base | Catalyst | Conv. A | Yield % C |
|---|---|---|---|---|---|---|
| 1 | 1.5 | 2.25 mL | $K_2CO_3$ | $NEt_3$ (1 equiv) | 100 | 80 |
| 2 | 5 | 2.25 mL | $K_2CO_3$ (5 equiv) | I (0.1 equiv) | 100 | 70 (5% e.e.) |
| 3 | 5 | 2.25 mL | $K_2CO_3$ (5 equiv) | II (0.1 equiv) | 100 | 20 (7% e.e.) |

Alternative preparation of 3-methyl-5-(4-methyl-2-nitromethyl-pentyl)-4-nitro-isoxazole (5)

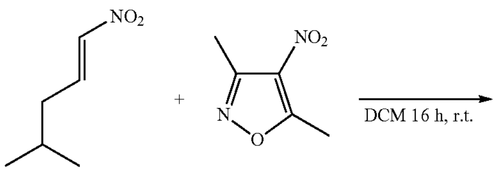

A B

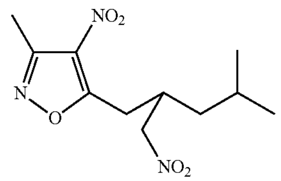

5

4-Methyl-1-nitro-pent-1-ene (Alkene A) was prepared via condensation of isovaleraldehyde and nitromethane in presence of base according to a literature procedure [Liu, J-m; Wang, X.; Ge, Z-m; Sun, Q.; Cheng, T-m, Li, R-t Tetrahedron, 2011, 67, 636].

Procedure:

To a solution of 4-methyl-1-nitro-pent-1-ene A (0.5 mmol) in dichloromethane (2.25 mL) were sequentially added 3,5-dimethyl-4-nitroisoxazole (5 equiv), catalyst and base as indicated in table 11. The resulting mixture was then stirred at room temperature for 16 h, then quenched with sat ammonium chloride (3 mL). The organic layer was separated, the solvent evaporated and the crude material purified via flash chromatography to give desired 3-methyl-5-(4-methyl-2-nitromethyl-pentyl)-4-nitro-isoxazole 5.

Preparation of the Catalysts

N-benzyl-quinidinium bromide (4a):

To a suspension of quinidine (650 mg, 2.0 mmol, 1.0 eq.) in THF (12.0 mL) benzyl bromide (0.31 mL, 2.6 mmol, 1.3 eq.) was added. The resulting mixture was heated at 60° C. for 16 h. The reaction was diluted with $CH_2Cl_2$ (10 mL) and washed with $H_2O$ (3×15 mL). The organic phase was dried over $Na_2SO_4$ and the solvent evaporated under reduced pressure. The crude material was purified by column chromatography (chloroform/methanol 95:5) affording the title compound as a purple solid (512 mg, 52% yield). $\delta_H$ (400 MHz, $CDCl_3$): 8.60 (d, J=4.4, 1H), 7.95 (d, J=9.2, 1H), 7.81 (d, J=4.4, 1H), 7.72-7.70 (m, 2H), 7.36 (d, J=2.8, 1H), 7.35-7.18 (m, 4H), 6.73-6.71 (m, 1H), 6.57-6.56 (m, 1H), 6.02-5.89 (m, 2H), 5.25-5.19 (m, 3H), 4.67-4.55 (m, 1H), 3.95-3.90 (m, 2H), 3.85 (s, 3H), 3.44-3.41 (m, 1H), 2.98-

2.95 (m, 1H), 2.45-2.35 (m, 2H), 1.90-1.80 (m, 3H), 1.09-1.01 (m, 1H); m.p.: 198-202° C.

N-(4,5-dimethoxybenzyl-2-nitrobenzyl)quinidinium bromide (4b)

To a suspension of quinidine (650 mg, 2.0 mmol, 1.0 eq.) in THF (12.0 mL) 1-bromomethyl-4,5-dimethoxy-2-nitrobenzene (0.31 mL, 2.6 mmol, 1.3 eq.) was added. The resulting mixture was heated at 60° C. for 16 h. The reaction was diluted with $CH_2Cl_2$ (10 mL) and washed with $H_2O$ (3×15 mL). The organic phase was dried over $Na_2SO_4$ and the solvent evaporated under reduced pressure. The crude material was purified by column chromatography (chloroform/methanol 95:5) affording the title compound as a purple solid (650 mg, 90% yield). $\delta_H$ (400 MHz, $CDCl_3$): 8.80 (m, 1H), 8.30 (m, 1H), 8.10 (d, J=9.2, 1H), 7.90 (d, J=4.4, 1H), 7.72-7.70 (m, 2H), 7.10 (m 1H), 6.93-6.71 (m, 3H), 6.57-6.56 (m, 1H), 6.80-5.73 (m, 1H), 5.25-5.19 (m, 2H), 4.95-4.90 (m, 1H), 3.95 (s, 3H), 3.90 (s, 3H), 3.85 (s, 3H), 3.44-3.41 (m, 1H), 2.98-2.95 (m, 1H), 2.45-2.35 (m, 2H), 1.90-1.80 (m, 3H), 1.09-1.01 (m, 1H); m.p.: 202-205° C.

N-benzyl-cinchonidinium Bromide:

To a flame-dried flask equipped with a magnetic stirring bar and a reflux condenser was added cinchonine (1.00 g, 3.4 mmol), THF (50 mL), and desired benzyl bromide derivative (3.4 mmol). The mixture was heated to reflux until judged to be complete by TLC-analysis ($CH_2Cl_2$/MeOH 9:1) and then cooled to room temperature and poured onto $Et_2O$ (150 mL) with stirring. The resulting suspension was stirred for 1 h and the precipitated solids were isolated by filtration, which was recrystallized from MeOH/$Et_2O$ as follows: to the crude product was added 5-10 mL MeOH until the solid just dissolves at reflux and then the mixture was placed at room temperature. To the warmed solution was quickly added $Et_2O$ until crystal formation was initiated and then the solution was allowed to cool slowly to room temperature over night. Removal of the mother liquid and washing with $Et_2O$ afforded the product as crystal. Prepared according to the general procedure, cinchonine (1.00 g, 3.4 mmol) and benzyl bromide (0.58 g, 3.4 mmol) gave the product as colourless crystals 1.37 g (reaction time 4.5 h). Isolated yield 86.9% after recrystallisation. mp 259-261° C. (dec.); $^1H$ NMR (400 MHz, $CDCl_3$) δ 8.84 (1H, d, J=5), 8.34 (1H, d, J=8), 7.93 (1H, d, J=4), 7.64 (1H, d, J=8), 7.58 (2H, d, J=7.0), 7.22-6.98 (5H, m), 6.83-6.70 (1H, m), 6.50 (1H, bs), 6.18-6.03 (1H, m), 5.89-5.76 (1H, m), 5.41-5.26 (1H, m), 5.26-5.11 (2H, m), 4.49-4.38 (1H, m), 4.20-4.02 (2H, m), 3.29 (1H, t, J=12 Hz), 2.74 (1H, dd, J=21, J=10), 2.27 (1H, dd, J=17, J=9 Hz), 2.13-2.01 (1H, m), 1.82-1.63 (3H, m), 0.77-0.63 (1H, m); $^{13}C$ NMR (100 MHz, $CDCl_3$) δ 149.1, 146.6, 144.9, 135.2, 134.0, 129.9, 129.2, 128.6, 128.25, 127.3, 126.9, 123.5, 123.3, 119.7, 118.1, 66.7, 65.7 61.4, 56.3, 53.6, 53.4, 38.0, 27.2, 23.8, 21.8.

N-(3,5-bis(trifluoromethyl)benzyl) cinchonidinium bromide:

To a stirred suspension of cinchonidine (294.4 mg, 1.0 mmol) in toluene (4.0 mL), 3,5-bis(trifluoromethyl)benzyl bromide (220 μL, 1.2 mmol) was added. The resulting mixture was then heated at 80° C., and stirred for 24 h at the same temperature. After cooling to r.t., the precipitate was collected by Bückner filtration and washed several times with $Et_2O$, affording the title compound as a white solid in 75% yield. [α]D20=−126 (c=0.81 in $CH_3OH$); 1H NMR ($CD_3OD$, 400 MHz) δ 8.94 (d, J=4.6 Hz, 1H), 8.46 (s, 2H), 8.36-8.32 (m, 1H), 8.23 (s, 1H), 8.14-8.10 (m, 1H), 7.95 (d, J=4.5 Hz, 1H), 7.88-7.89 (m, 2H), 6.66 (d, J=1.6 Hz, 1H), 5.68 (ddd, J=17.3, 10.5, 6.8 Hz, 1H), 5.41 (d, J=12.7 Hz, 1H), 5.31 (d, J=12.7 Hz, 1H), 5.17 (dt, Jd=17.2 Hz, Jt=1.0 Hz, 1H), 4.99 (dt, Jd=10.5 Hz, Jt=1.1 Hz, 1H), 4.58 (tddd, Jt=11.3 Hz, Jt=8.3, 5.1, 3.0 Hz, 1H), 4.05 (dd, J=9.7, 8.8 Hz, 1H), 3.80 (dddd, J=12.4, 7.9, 4.7, 3.3 Hz, 1H), 3.46 (dd, J=12.3, 10.6 Hz 1H), 3.38 (dt, Jt=11.4 Hz, Jd=4.8 Hz, 1H), 2.73 (bs, 1H), 2.37-2.19 (m, 1H), 2.08 (bs, 1H), 1.96-1.84 (m, 1H), 1.48-1.37 (m, 1H), 0.83-0.73 (m, 1H); 13C NMR ($CD_3OD$, 100 MHz) δ 149.9, 147.6, 146.1, 137.3, 134.3 (q, J=4 Hz), 132.5 (q, J=36 Hz), 130.9, 130.0, 129.2, 128.7, 128.1, 128.0, 125.1, 124.9, 123.3 (q, J=275 Hz), 123.0, 120.1, 116.5, 69.1, 65.1, 62.2, 60.7, 51.8, 37.9, 26.7, 24.7, 21.3; 19F NMR ($CD_3OD$, 156 MHz) δ−64.6; ESI-MS: 521 [M+].

General Procedure for the Preparation of Catalysts A-E

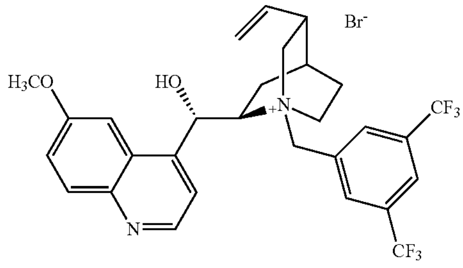

Catalyst A

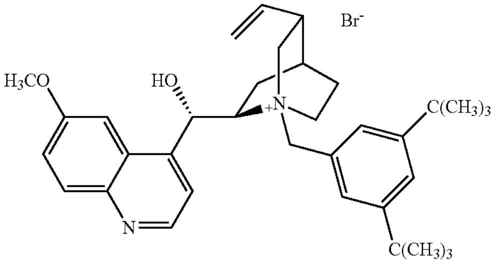

Catalyst B

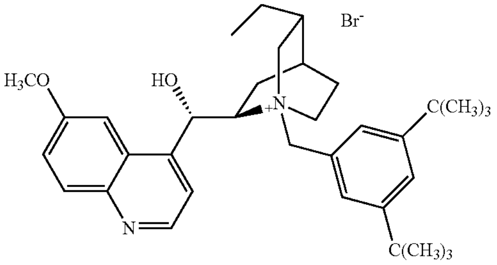

Catalyst C

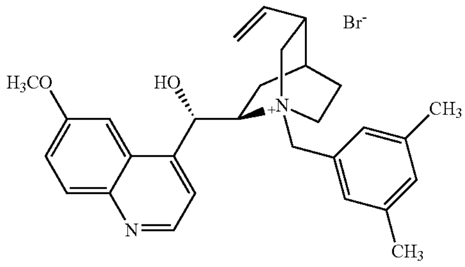

Catalyst D

-continued

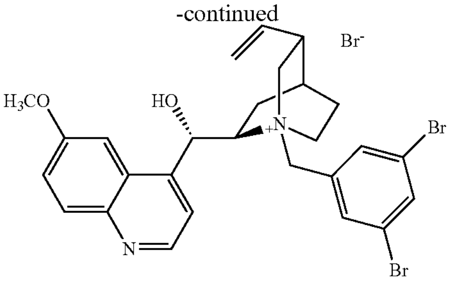

Catalyst E

In a round bottomed flask fitted with a magnetic stirrer and a reflux condenser were put sequentially quinidine (1.0 equiv), the appropriate benzyl bromide (1.05 equiv) and acetone to make a 0.18-0.20M solution. It was noted that at 50-55° C. the reaction became clear. The resulting solution was heated at 60-65° C. for 2 h. The reaction mixture was then allowed to reach room temperature, the solvent evaporated to give a solid which was suspended in petroleum ether, stirred for 30 minutes, then filtered and dried to give pure quinidinium bromides A-E. Optionally compounds A-B may be dissolved in the minimum quantity of DCM and then precipitated by addition of $Et_2O$.

NOTE 1: Commercial sources of quinidine always contain variable amounts of dihydroquinidine. This implies that Catalysts A-B and D-E may contain variable amounts of the corresponding dihydroquinidinium salt.

NOTE 2: In the synthesis of compounds C-E, it was noted the formation of a precipitate from hot acetone, minutes from refluxing at 60-65° C.

NOTE 3: Compounds A-B may form sticky viscous oils when wet (Acetone, DCM); Drying under reduce pressure (rotavapor) gave compounds A-E as a fine powder.

Catalyst A: N-(3,5-ditrifluoromethylbenzyl)quinidinium bromide:

light yellow powder; $\delta_H$ (400 MHz, $CDCl_3$) 8.39-8.36 (1H, m), 8.25-8.24 (2H, m), 7.74 (1H, s), 7.67 (1H, d, J=8 Hz), 7.61 (1H, d, J=4 Hz), 7.49 (1H, d, J=4 Hz), 6.95-6.92 (1H, m), 6.48-6.47 (1H, m), 6.12-6.09 (1H, m), 6.10 (1H, d, J=8 Hz), 5.82 (1H, d, J=8 Hz), 5.80-5.74 (1H, m), 5.16-5.10 (2H, m), 4.56-4.50 (1H, m), 4.34-4.29 (1H, m), 4.15-4.10 (1H, m), 3.68 (3H, s), 3.08-3.02 (1H, m), 2.64-2.59 (1H, m), 2.39-2.19 (2H, m), 1.77-1.73 91H, m), 0.85-0.82 (1H, m); $\delta_c$ (100.6 MHz, $CDCl_3$) 157.9, 147.0, 144.0, 142.0, 134.9, 133.9, 132.6, 132.3, 131.6, 130.4, 126.0, 123.9, 121.2, 120.4, 120.0, 118.5, 103.2, 68.1, 67.1, 60.4, 60.2, 56.5, 56.3, 54.5, 37.9, 27.0, 23.8, 21.9.

Catalyst B: N-(3,5-ditertbutylbenzyl)quinidinium bromide:

colourless powder; $\delta_H$ (400 MHz, $CDCl_3$) 8.61-8.59 (1H, m), 7.97-7.94 (1H, m), 7.68-7.67 (1H, m), 7.60-7.59 (1H, m), 7.53-7.51 (1H, m), 7.3-7.26 (2H, m), 6.79-6.77 (1H, m), 6.58-6.55 (1H, m), 6.00-5.92 (1H, m), 5.83-5.80 (1H, m), 5.19-5.15 (2H, m), 4.85-4.76 (1H, m), 4.62-4.57 (1H, m), 4.10-4.04 (1H, m), 3.93 (3H, s), 3.88-3.83 (1H, m), 3.50-3.44 (1H, m), 3.07-3.02 (1H, m), 1.89-1.85 (1H, m), 1.80-1.75 (1H, m), 1.08-1.01 (1H, m); $\delta_c$ (100.6 MHz, $CDCl_3$) 157.9, 152.0, 147.4, 144.2, 143.0, 135.8, 131.8, 128.3, 126.2, 126.1, 124.4, 121.0, 120.5, 118.1, 102.2, 68.4, 65.3, 64.3, 56.8, 56.0, 54.2, 38.3, 35.0, 31.4, 30.9, 27.8, 24.2, 21.5.

Catalyst C: N-(3,5-ditertbutylbenzyl)dihydroquinidinium bromide:

colourless powder; $\delta_H$ (400 MHz, $CDCl_3$) 8.69-8.68 (1H, m), 8.03-8.00 (1H, m), 7.75-7.74 (1H, m), 7.59-7.58 (2H, m), 7.54-7.53 (1H, m), 7.63-7.29 (2H, m), 6.82-6.80 (1H, m), 6.66-6.62 (1H, m), 4.76-4.73 (1H, m), 4.42-4.36 (1H, m), 3.94 (3H, s), 3.74-3.65 (2H, m) 3.55-3.46 (1H, m), 3.14-3.06 (1H, m), 2.54-2.48 (1H, m), 1.94-1.88 (1H, m), 1.81-1.77 (1H, m), 1.69-1.55 (3H, m), 0.88-0.84 (1H, m); $\delta_c$ (100.6 MHz, $CDCl_3$) 158.0, 152.1, 147.7, 144.3, 143.1, 132.2, 128.3, 126.2, 126.0, 124.5, 120.6, 120.5, 102.3, 68.9, 64.9, 64.6, 57.1, 56.0, 55.9, 36.2, 35.0, 31.4, 31.3, 24.9, 24.6, 24.3, 21.3, 11.4.

Catalyst D: N-(3,5-dimethylbenzyl)quinidinium bromide: colourless powder; $\delta_H$ (400 MHz, $CDCl_3$) 8.45-8.43 (1H, m), 7.89-7.86 (1H, m), 7.71-7.70 (1H, m), 7.20-7.19 (1H, m), 7.20-7.17 (2H, m), 6.89-6.88 (1H, m), 6.69-6.67 (1H, m), 6.47-6.45 (1H, m), 5.89-5.81 (1H, m), 5.73-5.69 (1H, m), 5.17-5.12 (2H, m), 4.53-4.48 (1H, m), 3.91-3.86 (1H, m), 3.80 (3H, s), 3.43-3.38 (1H, m), 2.93-2.90 (1H, m), 2.39-2.34 92H, m), 2.30 (6H, s), 1.80-1.65 (4H, m), 0.93-0.80 (1H, m); □$_c$ (1 δ 0.6 MHz, $CDCl_3$) 157.8, 147.3, 144.3, 142.6, 138.7, 135.6, 131.9, 131.7, 131.4, 126.8, 126.4, 120.7, 120.6, 118.0, 102.8, 68.0, 66.9, 62.9, 56.6, 56.0, 54.0, 38.2, 27.2, 24.0, 21.7, 21.3.

Catalyst E: N-(3,5-dibromobenzyl)quinidinium bromide: colourless powder; $\delta_H$ (400 MHz, $CDCl_3$) 8.36-8.35 (1H, m), 7.82-7.74 (4H, m), 7.66-7.65 (1H, m), 7.04-7.01 (1H, m), 6.58-6.56 (1H, m), 6.44-6.40 (1H, m), 6.17-6.15 (1H, m), 5.86-5.79 (1H, m), 5.64-5.59 (1H, m), 5.28-5.22 (2H, m), 4.55-4.52 (1H, m), 4.27-4.25 (2H, m), 3.70 (3H, s), 3.23-3.20 (1H, m), 2.79-2.76 (1H, m), 2.40-2.38 (1H, m), 2.25-2.21 (1H, m), 1.85-1.77 (3H, m), 0.93-0.85 (1H, m); $\delta_c$ (100.6 MHz, $CDCl_3$) 157.7, 147.0, 144.1, 142.0, 136.2, 135.1, 135.0, 131.6, 131.1, 126.3, 123.5, 120.5, 119.5, 118.2, 103.8, 67.7, 59.8, 56.3, 56.0, 54.2, 37.9, 27.0, 23.8, 22.0, 15.3.

Preparation of 5-Methyl-3-nitromethyl-hexanoic acid (6) (Procedure A):

A solution of adduct 5, (0.25 mmol) in THF (0.5 mL) was charged in a round bottomed flask and treated with an aqueous solution of NaOH (1N, 1.35 mL, 5.5 equiv.). The resulting deep yellow solution was refluxed (T of the oil bath=100° C.) for 1 h, then allowed to reach room temperature, the THF evaporated in vacuo and the aqueous solution so obtained was made acidic (pH=2) by addition of 6N aqueous HCl. The aqueous solution obtained was evaporated in vacuo to give a solid which was then washed with DCM (2×10 mL). Compound 6 was obtained as solid in 70% yield upon evaporation of the DCM solution. $^1$H NMR (400 MHz, $CDCl_3$) $\delta_H$ 4.50 (1H, dd, J=12, J=7), 4.44 1H, dd, J=12, J=6) 2.67 (1H, sep J=6 Hz), 2.49 (2H, d, J=6), 1.66 (1H, sept, J=7), 1.28 (2H, m), 0.93 (3H, d, J=7), 0.91 (3H, d, J=7). $^{13}$C NMR $\delta_c$(100.1 MHz, $CDCl_3$) 177.6, 78.4, 40.3, 35.6, 31.7, 24.9, 22.3, 22.0.

Preparation of 5-Methyl-3-nitromethyl-hexanoic acid (6) (Procedure B):

To a solution of adduct 5, (0.25 mmol) in THF (0.5 mL) was added dropwise a solution of $KMnO_4$ (3 equiv) in $H_2O$:Acetone (4:1) 4.5 mL. The reaction mixture was stirred for 1 hour at room temperature and then a $Na_2SO_3$ saturated solution (5 mL) was added to destroy the excess of $KMnO_4$: the formation of a brown precipitate was observed ($MnO_2$). The mixture was then acidified with HCl 6 M until pH=3. At this point it was noted that the solution became clear. The mixture was then extracted with DCM (3×1 mL) and the combined organic phases were evaporated. Compound 6 was obtained as solid in 90% yield upon evaporation of the DCM solution.

Preparation of 5-Methyl-3-nitromethyl-hexanoic acid (6) (Procedure C):

A solution of adduct 5, (39.2 g 144 mmol) in THF (100 mL) was charged in a round bottomed flask and treated with a freshly made aqueous solution (1N, 720 mL, 5 equiv.) of NaOH (28.8 g, 720 mmol). The resulting dark solution was refluxed (T=60-65° C.) for 16 h, then allowed to reach room temperature, the THF evaporated in vacuo and the aqueous solution so obtained was extracted with toluene (300 mL), the aqueous layer was made cold (0° C.) by an ice water bath, then HCl conc was added drop wise with stirring until pH ~2-3. This addition must be done carefully to avoid formation of side products. The aqueous solution was then extracted with toluene (3×200 mL), the organic layer washed with water (2×150 mL) and concentrated in vacuo to give acid 6 as a yellow brown viscous oil (25.2, 93% yield). $^{1}H$ NMR (400 MHz, $CDCl_3$) $\delta_H$ 4.50 (1H, dd, J=12, J=7), 4.44 1H, dd, J=12, J=6) 2.67 (1H, sep J=6 Hz), 2.49 (2H, d, J=6), 1.66 (1H, sept, J=7), 1.28 (2H, m), 0.93 (3H, d, J=7), 0.91 (3H, d, J=7). $^{13}C$ NMR $\delta_c$(100.1 MHz, $CDCl_3$) 177.6, 78.4, 40.3, 35.6, 31.7, 24.9, 22.3, 22.0.

NOTE 1: starting from adduct 5 68% ee enantioenriched, compound 6 was obtained in 68% ee; starting from adduct 5 85% ee enantioenriched, compound 6 was obtained in 85% ee.

Preparation of (S)-Pregabalin (7):

Compound 6 was reduced to 7 using a literature procedure described in F. Felluga, G. Pitacco, E. Valentin, C. D. Venneri *Tetrahedron: Asymm.* 2008, 945 which is incorporated herein by reference.

Preparation of (S)-Pregabalin (7)-Reduction of Compound 6 using Pd/C:

In a round bottomed flask were charged compound 6 (50 g, 264 mmol, Mw=189, 80% ee), methanol (260 mL) and Pd/C (10%, 15 g). The suspension obtained was stirred at room temperature for 24 h under an atmosphere of $H_2$ (1 atm) then filtered through a pad of celite and the solution evaporated to give a white solid which was washed with hexane (20 mL) to give (S)-pregabalin (40.3 g, 96% yield).

NOTE 1: the reduction could be carried out under pressure at room temperature (18° C.).

Preparation of (S)-Pregabalin (7)-Reduction of Compound 6 Using Ni/Ra:

In a round bottomed flask were charged compound 6 (50 g, 264 mmol, Mw=189, 80% ee), methanol (250 mL) and Ni Raney (10%, 5 g). The suspension obtained was stirred at room temperature under an atmosphere of $H_2$ (10 atm) for 16 h, then filtered through a pad of celite and the solution evaporated to give (S)-pregabalin (39.4 g, 94% yield) as a colourless solid.

Preparation of (S)-Pregabalin (7)-Crystallisation of enantiopure (S)-Pregabalin:

Enantioenriched (S)-pregabalin (30 g, 68-86% ee) was dissolved in hot isopropanol (100 mL), then water (35 mL) added and the mixture allowed to reach room temperature (18° C.) and then cooled at 0° C., to give a precipitate of (S)-pregabalin (60% to 80% yield).

Preparation of (S)-Pregabalin (7)-Partial resolution of (S)-Pregabalin:

To a solution of enantioenriched (S)-pregabalin (30 g, 68-86% ee) in hot isopropanol (120 mL) water (25 mL) was added (R)-(−)-mandelic acid (0.2-0.1 equiv) and the solution refluxed for 30 minutes, then allowed to reach room temperature (18° C.) and finally cooled at 0° C., to give a precipitate of (R)-pregabalin/(R)-(−)-mandelic acid. The filtrate was concentrated to give enantiopure (S)-pregabalin in 84-92% yield.

Analogues of compound 8 were prepared using a similar method to that above and are exemplified below.

1-(3-Methyl-4-nitro-isoxazol-5-yl)-propan-2-ol (9)

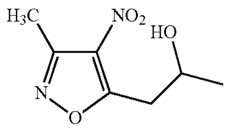

9

Colorless liquid; $R_f$=0.2 (Petroleum Ether/Ethyl Acetate, 90:10); $\delta_H$ (400 MHz, $CDCl_3$) 4.38-4.33 (1H, m), 3.37 (1H, dd, J=15 J=7), 3.35 (1H, dd, J=15 J=4), 2.56 (3H, s), 1.35 (3H, d, J=6); $\delta_c$ (100.6 MHz, $CDCl_3$) 172.6, 155.8, 66.1, 37.1, 23.8, 11.8. HRMS: m/z found $[M+H]^+$187.0742, $C_7H_{11}N_2O_4$ requires 187.0719.

1-(3-Methyl-4-nitro-isoxazol-5-yl)-butan-2-ol (10)

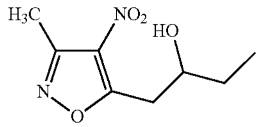

10

Colorless liquid; $R_f$=0.2 (Petroleum Ether/Ethyl Acetate, 90:10); $\delta_H$ (400 MHz, $CDCl_3$) 4.09-4.06 (1H, m), 3.36 (1H, dd, J=15 J=4), 3.35 (1H, dd, J=15 J=6), 2.56 (3H, s), 1.66-1.59 (2H, m), 1.03 (3H, t, J=7); $\delta_c$ (100.6 MHz, $CDCl_3$) 172.9, 155.8, 130.8, 71.1, 35.2, 30.6, 11.8, 9.8. HRMS: m/z found $[M+H]^+$201.0851, $C_8H_{13}N_2O_4$ requires 201.0875.

1-(3-Methyl-4-nitro-isoxazol-5-yl)-pentan-2-ol (11)

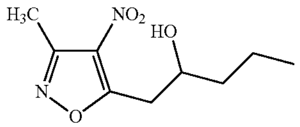

11

Colorless liquid; $R_f$=0.2 (Petroleum Ether/Ethyl Acetate, 90:10); $\delta_H$ (400 MHz, $CDCl_3$) 4.17-4.11 (1H, m), 3.36 (1H, dd, J=15 J=4), 3.32 (1H, dd, J=15 J=6), 2.55 (3H, s), 1.60-1.38 (4H, m), 0.94 (3H, t, J=7); $\delta_c$ (100.6 MHz, $CDCl_3$) 172.9, 155.8, 130.8, 69.5, 39.8, 35.7, 18.8, 13.9, 11.8. HRMS: m/z found $[M+H]^+$215.1011, $C_9H_{15}N_2O_4$ requires 215.1032.

1-(3-Methyl-4-nitro-isoxazol-5-yl)-hexan-2-ol (12)

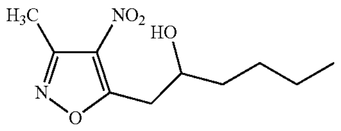

12

Colorless liquid; $R_f$=0.2 (Petroleum Ether/Ethyl Acetate, 90:10); $\delta_H$ (400 MHz, $CDCl_3$) 4.16-4.10 (1H, m), 3.38 (1H, dd, J=15 J=4), 3.33 (1H, dd, J=15 J=6), 2.58 (3H, s), 1.62-1.21 (6H, m), 0.86 (3H, t, J=7); $\delta_c$ (100.6 MHz, $CDCl_3$) 172.9, 155.8, 69.9, 37.5, 35.7, 27.7, 22.6, 21.2, 14.1, 11.8. HRMS: m/z found $[M+H]^+$229.1196, $C_{10}H_{17}N_2O_4$ requires 229.1188.

1-(3-Methyl-4-nitro-isoxazol-5-yl)-nonan-2-ol (13)

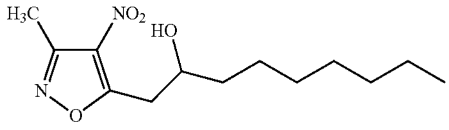

13

Colorless liquid; $R_f$=0.2 (Petroleum Ether/Ethyl Acetate, 90:10); $\delta_H$ (400 MHz, $CDCl_3$) 4.15-4.12 (1H, m), 3.38 (1H, dd, J=15 J=4), 3.33 (1H, dd, J=15 J=6), 2.56 (3H, s), 1.60-1.57 (2H, m), 1.38-1.20 (10H, m), 0.88 (3H, t, J=7); $\delta_c$ (100.6 MHz, $CDCl_3$) 172.9, 155.8, 130.8, 69.9, 37.8, 35.7, 31.9, 29.8, 29.4, 25.5, 22.8, 14.2, 11.8. HRMS: m/z found $[M+H]^+$271.1669, $C_{13}H_{23}N_2O_4$ requires 271.1658.

1-(3-Methyl-4-nitro-isoxazol-5-yl)-decan-2-ol (14)

14

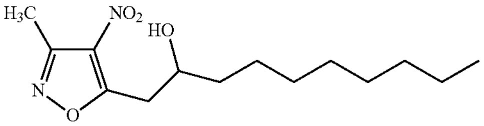

Colorless liquid; $R_f$=0.2 (Petroleum Ether/Ethyl Acetate, 90:10); $\delta_H$ (400 MHz, $CDCl_3$) 4.17-4.12 (1H, m), 3.38 (1H, dd, J=15 J=4), 3.33 (1H, dd, J=15 J=6), 2.56 (3H, s), 1.62-1.56 (2H, m), 1.38-1.20 (12H, m), 0.88 (3H, t, J=7); $\delta_c$ (100.6 MHz, $CDCl_3$) 172.9, 155.8, 130.9, 69.9, 37.8, 35.7, 31.9, 29.6, 29.5, 29.3, 25.5, 22.8, 14.2, 11.8. HRMS: m/z found $[M+H]^+$285.1828, $C_{14}H_{25}N_2O_4$ requires 285.1814.

Analogues of compound 3 were prepared using a similar method to that above and are exemplified below.

3-Methyl-4-nitro-5-propenyl-isoxazole (15)

15

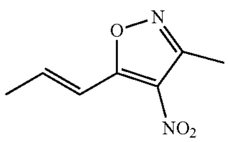

Colorless liquid; $R_f$=0.8 (Petroleum Ether/Ethyl Acetate, 90:10); $\delta_H$ (400 MHz, $CDCl_3$) 7.10-7.06 (2H, m), 2.55 (3H, s), 2.08-2.06 (3H, m); $\delta_c$ (100.6 MHz, $CDCl_3$) 167.1, 156.0, 144.0, 116.1, 19.7, 12.0. HRMS: m/z found $[M]^+$168.0554, $C_7H_8N_2O_3$ requires 168.0535.

5-But-1-enyl-3-methyl-4-nitro-isoxazole (16)

16

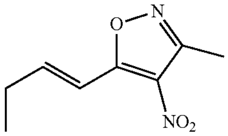

Colorless liquid; $R_f$=0.8 (Petroleum Ether/Ethyl Acetate, 90:10); $\delta_H$ (400 MHz, $CDCl_3$) 7.18-7.01 (2H, m), 2.56 (3H, s), 2.44-2.38 (2H, m), 1.17 (3H, t, J=7), $\delta_c$ (100.6 MHz, $CDCl_3$) 167.3, 156.0, 150.2, 113.8, 29.8, 26.9, 11.9. HRMS: m/z found $[M]^+$182.0648, $C_8H_{10}N_2O_3$ requires 182.0691.

3-Methyl-4-nitro-5-pent-1-enyl-isoxazole (17)

17

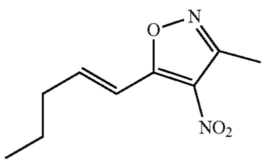

Colorless liquid; $R_f$=0.8 (Petroleum Ether/Ethyl Acetate, 90:10); $\delta_H$ (400 MHz, $CDCl_3$) 7.11-7.00 (2H, m), 2.54 (3H, s), 2.38-2.33 (2H, m), 1.62-1.53 (2H, m), 0.98 (3H, t, J=7); $\delta_c$ (100.6 MHz, $CDCl_3$) 167.1, 156.0, 148.8, 114.7, 35.8, 21.6, 13.8, 11.9. HRMS: m/z found $[M]^+$196.0856, $C_9H_{12}N_2O_3$ requires 196.0848.

5-Hex-1-enyl-3-methyl-4-nitro-isoxazole (18)

18

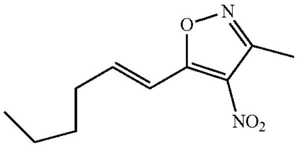

Colorless liquid; $R_f$=0.8 (Petroleum Ether/Ethyl Acetate, 90:10); $\delta_H$ (400 MHz, $CDCl_3$) 7.12-7.00 (2H, m), 2.55 (3H, s), 2.41-2.35 (2H, m), 1.56-1.48 (2H, m), 1.43-1.38 (2H, m), 0.94 (3H, t, J=7); $\delta_c$ (100.6 MHz, $CDCl_3$) 167.2, 156.0, 149.0, 114.6, 33.5, 30.4, 22.4, 16.9, 11.9. HRMS: m/z found $[M]^+$210.1016, $C_{10}H_{14}N_2O_3$ requires 210.1004.

3-Methyl-4-nitro-5-non-1-enyl-isoxazole (19)

19

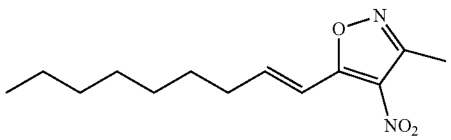

Colorless liquid; $R_f$=0.8 (Petroleum Ether/Ethyl Acetate, 90:10); $\delta_H$ (400 MHz, $CDCl_3$) 7.13-6.95 (2H, m), 2.56 (3H, s), 2.40-2.35 (2H, m), 1.56-1.50 (2H, m), 1.37-1.25 (8H, m), 0.87 (3H, t, J=7); $\delta_c$ (100.6 MHz, $CDCl_3$) 167.2, 156.0, 149.2, 114.6, 33.9, 31.9, 29.8, 29.3, 29.2, 28.3, 22.8, 14.2, 12.0. HRMS: m/z found $[M]^+$252.1448, $C_{13}H_{20}N_2O_3$ requires 252.1474.

5-Dec-1-enyl-3-methyl-4-nitro-isoxazole (20)

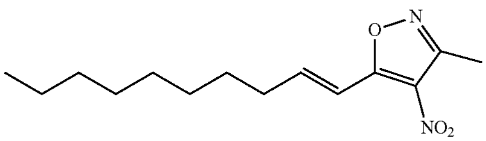

20

Colorless liquid; $R_f$=0.8 (Petroleum Ether/Ethyl Acetate, 90:10); $\delta_H$ (400 MHz, $CDCl_3$) 7.13-6.95 (2H, m), 2.57 (3H, s), 2.45-2.38 (2H, m), 1.65-1.20 (12H, m), 0.89 (3H, t, J=7), $\delta_c$ (100.6 MHz, $CDCl_3$) 167.2, 156.0, 149.2, 114.6, 33.9, 31.9, 29.5, 29.3, 28.3, 22.8, 14.2, 11.9. HRMS: m/z found $[M]^+$266.1630, $C_{14}H_{22}N_2O_3$ requires 266.1630.

Analogues of compound 5 were prepared using a similar method to that above and are exemplified below.

3-Methyl-5-(2-methyl-3-nitro-propyl)-4-nitro-isoxazole (21)

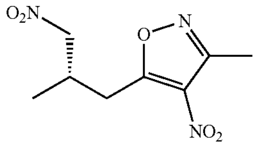

21

Compound 21: Procedure B, 91% yield, 93% ee Colorless liquid; $R_f$=0.2 (Petroleum Ether/Ethyl Acetate, 90:10); $\delta_H$ (400 MHz, $CDCl_3$) 4.44 (1H, dd, J=12, J=6), 4.37 (1H, dd, J=12, J=6), 3.35 (1H, dd, J=15, J=7), 3.26 (1H, dd, J=15, J=7), 2.96 (1H, sept, J=6), 2.59 (3H, s), 1.15 (3H, d, J=7); $\delta_c$ (100.6 MHz, $CDCl_3$) 172.2, 156.0, 78.1, 37.4, 29.8, 11.8, 10.8. HRMS: m/z found $[M+H]^+$230.0714, $C_8H_{12}N_2O_5$ requires 230.0777.

3-Methyl-4-nitro-5-(2-nitromethyl-butyl)-isoxazole (22)

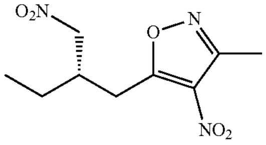

22

Compound 22: Procedure B, 91% yield, 93% ee Colorless liquid; $R_f$=0.2 (Petroleum Ether/Ethyl Acetate, 90:10); $\delta_H$ (400 MHz, $CDCl_3$) 4.47 (1H, dd, J=13, J=6), 4.42 (1H, dd, J=13, J=6), 3.38 (1H, dd, J=15, J=7), 3.28 (1H, dd, J=15, J=7), 2.76 (1H, sept, J=6), 2.58 (3H, s), 1.32-1.27 (2H, m), 1.03 (3H, t, J=7); $\delta_c$ (100.6 MHz, $CDCl_3$) 172.2, 156.0, 78.1, 37.4, 29.8, 24.7, 11.8, 10.8. HRMS: m/z found $[M+H]^+$ 244.0968, $C_9H_{14}N_2O_5$ requires 244.0933.

3-3-Methyl-4-nitro-5-(2-nitromethyl-pentyl)-isoxazole (23)

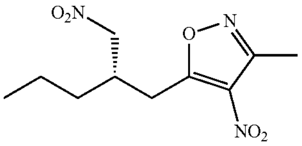

23

Compound 23: Procedure A 92% yield, 84% ee; Procedure B, 91% yield, 92% ee Colorless liquid; $R_f$=0.2 (Petroleum Ether/Ethyl Acetate, 90:10); $\delta_H$ (400 MHz, $CDCl_3$) 4.45 (1H, dd, J=12, J=6), 4.40 (1H, dd, J=12, J=6), 3.37 (1H, dd, J=15, J=7), 3.30 (1H, dd, J=15, J=7), 2.82 (1H, sept, J=6), 2.58 (3H, s), 1.46-1.40 (4H, m), 0.94 (3H, t, J=7); $\delta_c$ (100.6 MHz, $CDCl_3$) 172.2, 156.0, 78.4, 35.8, 29.8, 19.7, 13.7, 11.8. HRMS: m/z found $[M+H]^+$258.1054, $C_{10}H_{16}N_2O_5$ requires 258.1090.

3-3-Methyl-4-nitro-5-(2-nitromethyl-pentyl)-isoxazole (24)

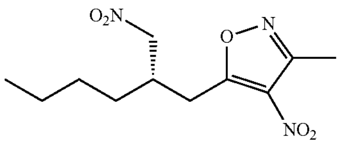

24

Compound 24: Procedure A 92% yield, 84% ee; Procedure B, 91% yield, 93% ee Colorless liquid; $R_f$=0.2 (Petroleum Ether/Ethyl Acetate, 90:10); $\delta_H$ (400 MHz, $CDCl_3$) 4.43 (1H, dd, J=12, J=6), 4.40 (1H, dd, J=12, J=6), 3.37 (1H, dd, J=15, J=7), 3.30 (1H, dd, J=15, J=7), 2.81 (1H, sept, J=6), 2.58 (3H, s), 1.50-1.27 (4H, m), 0.88 (3H, t, J=7); $\delta_c$ (100.6 MHz, $CDCl_3$) 172.3, 156.0, 129.2, 78.4, 36.0, 31.4, 29.9, 28.5, 22.6, 14.0, 11.8. HRMS: m/z found $[M+H]^+$ 272.1280, $C_{11}H_{18}N_3O_3$ requires 272.1246.

3-Methyl-4-nitro-5-(2-nitromethyl-nonyl)-isoxazole (25)

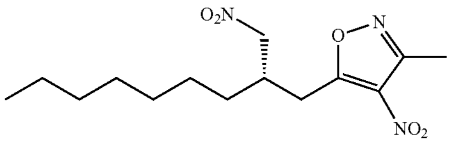

25

Compound 25: procedure A: 96% yield, 80% ee; procedure B, 91% yield, 91% ee. Colorless liquid; $R_f$=0.2 (Petroleum Ether/Ethyl Acetate, 90:10); $\delta_H$ (400 MHz, $CDCl_3$) 4.45 (1H, dd, J=8, J=6), 4.40 (1H, dd, J=8, J=6), 3.37 (1H, dd, J=15, J=7), 3.30 (1H, dd, J=15, J=7), 2.81 (1H, sept, J=6), 2.58 (3H, s), 1.50-1.27 (12H, m), 0.88 (3H, t, J=7); $\delta_c$ (100.6 MHz, $CDCl_3$) 172.3, 156.0, 78.4, 36.0, 31.8, 31.7, 29.9, 29.4, 29.1, 26.3, 22.7, 14.2, 11.8. HRMS: m/z found $[M+H]^+$314.1745, $C_{14}H_{24}N_3O_3$ requires 314.1716.

3-Methyl-4-nitro-5-(2-nitromethyl-decyl)-isoxazole (26)

26

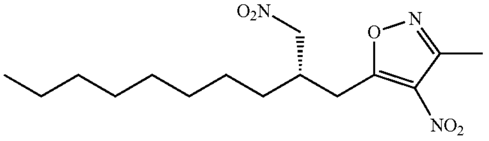

Compound 26: procedure A: 96% yield, 84% ee; procedure B, 91% yield, 94% ee. Colorless liquid; $R_f$=0.2 (Petroleum Ether/Ethyl Acetate, 90:10); $\delta_H$ (400 MHz, $CDCl_3$) 4.45 (1H, dd, J=8, J=6), 4.40 (1H, dd, J=8, J=6), 3.36 (1H, dd, J=15, J=7), 3.30 (1H, dd, J=15, J=7), 2.81 (1H, sept, J=6), 2.58 (3H, s), 1.48-1.26 (14H, m), 0.86 (3H, t, J=7); $\delta_c$ (100.6 MHz, $CDCl_3$) 172.3, 156.0, 78.4, 36.0, 31.9, 31.7, 29.9, 29.8, 28.4, 29.4, 26.3, 22.7, 14.2, 11.8. HRMS: m/z found $[M+H]^+$328.1849, $C_{15}H_{26}N_3O_5$ requires 328.1872.

The invention claimed is:

1. A process for the preparation of a compound of formula (I), or a pharmaceutically acceptable salt or solvate thereof:

(I)

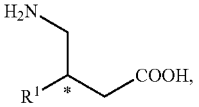

wherein:

$R^1$ is selected from the group consisting of an alkyl group, an alkenyl group, an alkynyl group and a cycloalkyl group, each of which may be optionally substituted; and

* denotes a chiral centre;

which process comprises the step of preparing a compound of formula (IV):

(IV)

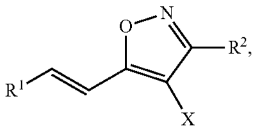

by reacting a compound of formula (III):

(III)

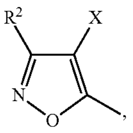

with a compound of formula (II):

(II)

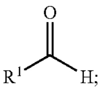

reacting the compound of formula (IV) with nitromethane in the presence of a catalyst to provide a compound of formula (V);

(V)

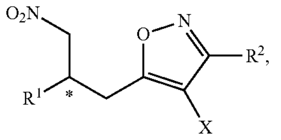

wherein $R^1$ and * are as defined above and $R^2$ is an alkyl group or aryl group, each of which may be optionally substituted; and X is $NO_2$, and converting the compound of formula (V) to the compound of formula (I), or a pharmaceutically acceptable salt or solvate thereof.

2. A process for the preparation of a compound of formula (I), or a pharmaceutically acceptable salt or solvate thereof:

(I)

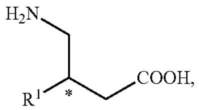

wherein:

$R^1$ is selected from the group consisting of an alkyl group, an alkenyl group, an alkynyl group and a cycloalkyl group, each of which may be optionally substituted; and

* denotes a chiral centre;

which process comprises preparing a compound of formula (IV):

(IV)

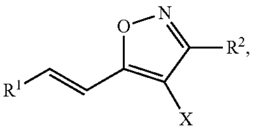

by reacting a compound of formula (IIIA):

(IIIA)

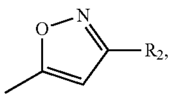

with a compound of formula (II):

(II)

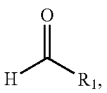

to form an intermediate hydroxyl compound of the following formula:

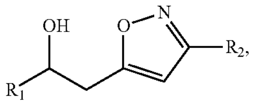

converting the intermediate hydroxyl compound to a compound of formula (IIIB):

(IIIB)

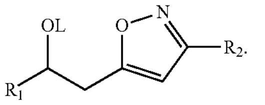

with or without isolating the intermediate hydroxyl compound, wherein L is a hydroxyl activating group, $R^1$ is selected from the group consisting of an alkyl group, an alkenyl group, an alkynyl group and a cycloalkyl group, each of which may be optionally substituted, and $R^2$ is an alkyl group or aryl group, each of which may be optionally substituted;

converting the compound of formula (IIIB) to a compound of formula (IIIC):

(IIIC)

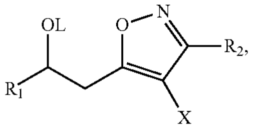

wherein X is $NO_2$; and converting the compound of formula (IIIC) to a compound of formula (IV):

(IV)

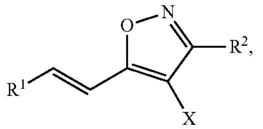

reacting the compound of formula (IV) with nitromethane in the presence of a catalyst to form a compound of formula (V):

(V)

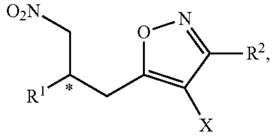

and converting the compound of formula (V) to the compound of formula (I), or a pharmaceutically acceptable salt or solvate thereof.

3. The process according to claim 1, wherein said converting the compound of formula (V) to the compound of formula (I), or a pharmaceutically acceptable salt or solvate thereof, comprises the step of hydrolysing the compound of formula (V) to provide a compound of formula (VI):

(VI)

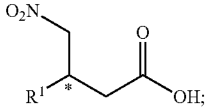

and converting the compound of formula (VI) to the compound of formula (I), or a pharmaceutically acceptable salt or solvate thereof.

4. The process according to claim 3; wherein said converting the compound of formula (VI) to the compound of formula (I), or a pharmaceutically acceptable salt or solvate thereof, comprises the step of reducing the compound of formula (VI) to the compound of formula (I).

5. The process according to claim 1 wherein $R^1$ is an optionally substituted alkyl group.

6. The process according to claim 1 wherein $R^1$ and $R^2$ are independently selected from the group consisting of methyl, ethyl, n-propyl, iso-propyl, n-butyl, sec-butyl, iso-butyl, tert-butyl, n-pentyl, n-hexyl, n-heptyl and n-octyl.

7. The process according to claim 6 wherein $R^1$ is iso-butyl and $R^2$ is methyl.

8. The process according to claim 1 wherein the compound of formula (I) is isolated with an enantiomeric excess of greater than about 70%.

9. The process according to claim 1 wherein the catalyst is a cinchona alkaloid derivative.

10. The process according to claim 1 wherein the catalyst is a compound of formula (VIIa) or (VIIb)

(VIIa)

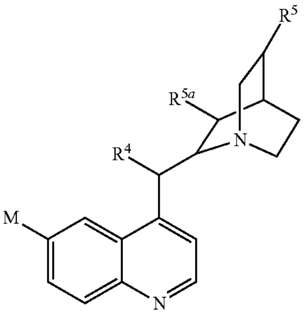

(VIIb)

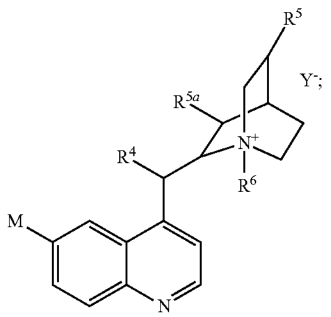

wherein, M is selected from the group consisting of H, hydroxy, alkoxy, O-alkenyl, $O(CH_2)_n$-aryl, $O(CH_2)_n$-heteroaryl, $O(CH_2)_n$-cycloalkyl, amino, $NR^{11}C(=O)R^{12}$, $C(=O)NR^{13}R^{14}$, $C(=O)R^{12}$, $O(C=O)R^{12}$, $C(=O)OR^{12}$, $NR^{11}SO_2R^{12}$, and $R^7$; in which each aryl, heteroaryl and cycloalkyl groups may be optionally substituted;

$R^4$ is selected from the group consisting of hydroxy, alkoxy, O-alkenyl, $O(CH_2)_n$-aryl, $O(CH_2)_n$-heteroaryl, $O(CH_2)_n$-cycloalkyl, amino, $NR^{11}C(=O)R^{12}$, $C(=O)NR^{13}R^{14}$, $C(=O)R^{12}$, $O(C=O)R^{12}$, $C(=O)OR^{12}$, $NR^{11}SO_2R^{12}$, and $R^7$; in which each aryl, heteroaryl and cycloalkyl groups may be optionally substituted;

$R^{11}$, $R^{12}$, $R^{13}$ and $R^{14}$ are independently selected from the group consisting of H, an alkyl group, an alkenyl group, an alkynyl group, an aryl group, a heteroaryl group and a cycloalkyl group, each of which may be optionally substituted; or $R^{13}$ and $R^{14}$ may together define an optionally substituted $C_3$-$C_{20}$ cycloalkyl group or $C_5$-$C_{15}$ heteroaryl group;

$R^5$ and $R^{5a}$ are independently selected from the group consisting of H, alkyl and alkenyl, each of which may be optionally substituted;

$R^6$ is selected from the group consisting of an alkyl group, an alkenyl group, an alkynyl group, an aryl group, a heteroaryl group, a cycloalkyl group, a $(CH_2)_n$-aryl group, a $(CH_2)_n$-heteroaryl group and a $(CH_2)_n$-cycloalkyl group; each of which may be optionally substituted;

n=0 to 6;

$R^7$ is

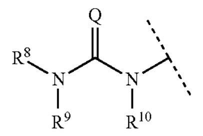

wherein Q is O or S; and $R^8$, $R^9$ and $R^{10}$ are independently selected from the group consisting of H, an alkyl group, an alkenyl group, an alkynyl group, an aryl group, a heteroaryl group and a cycloalkyl group, each of which may be optionally substituted, or $R^8$ and $R^9$ may together define an optionally substituted $C_3$-$C_{20}$ cycloalkyl group or an optionally substituted $C_5$-$C_{15}$ heteroaryl group; and $Y^-$ is a counterion.

11. The process according to claim 10 wherein the catalyst is a compound of formula (VIIa) wherein:

M is selected from the group consisting of H, hydroxy, alkoxy, $O(CH_2)_n$-aryl, $O(CH_2)_n$-heteroaryl, $O(CH_2)_n$-cycloalkyl and $R^7$;

$R^4$ is selected from the group consisting of hydroxy, alkoxy, O-alkenyl, $O(CH_2)_n$-aryl, $C(=O)OR^{12}$, amino, $NR^{11}SO_2R^{12}$, and $R^7$;

Q is S;

$R^5$ and $R^{5a}$ are independently selected from the group consisting of H, methyl, ethyl, propyl, ethenyl, propenyl;

$R^8$ is selected from the group consisting of an alkyl group, an aryl group and a cycloalkyl group each of which may be optionally substituted by one or more of halo, $CF_3$, Me and OMe;

$R^9$, $R^{10}$, $R^{11}$ are independently selected from the group consisting of H and alkyl; and $R^{12}$ is selected from the group consisting of H, alkyl, aryl and cycloalkyl; each of which may be optionally substituted by one or more of halo, $CF_3$, Me and OMe.

12. The process according to claim 10 wherein the catalyst is a compound of formula (VIIb) wherein:

M is selected from the group consisting of H, hydroxy, alkoxy, $O(CH_2)_n$-aryl, $O(CH_2)_n$-heteroaryl, $O(CH_2)n$-cycloalkyl and $R^7$;

$R^4$ is selected from the group consisting of hydroxy, alkoxy, O-alkenyl, $O(CH_2)_n$-aryl, C(=O)OR12, amino, $NR^{11}SO_2R^{12}$, and $R^7$;

Q is S;

$R^5$ and $R^{5a}$ are independently selected from the group consisting of H, methyl, ethyl, propyl, ethenyl, propenyl;

$R^6$ is selected from the group consisting of $(CH_2)_n$-aryl groups, $(CH_2)_n$-heteroaryl groups and $(CH_2)_n$-cycloalkyl groups, each of which may optionally be substituted with one or more halo, alkyl, $NO_2$, haloalkyl and methoxy groups;

$R^8$ is selected from the group consisting of an alkyl group, an aryl group and a cycloalkyl group each of which may be optionally substituted by one or more of halo, $CF_3$, Me and OMe;

$R^9$, $R^{10}$, $R^{11}$ are independently selected from the group consisting of H and alkyl; and $R^{12}$ is selected from the group consisting of H, alkyl, aryl and cycloalkyl; each of which may be optionally substituted by one or more of halo, $CF_3$, Me and OMe.

13. The process according to claim 1 wherein the catalyst is selected from the group consisting of:

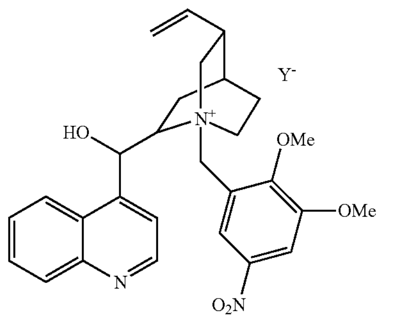

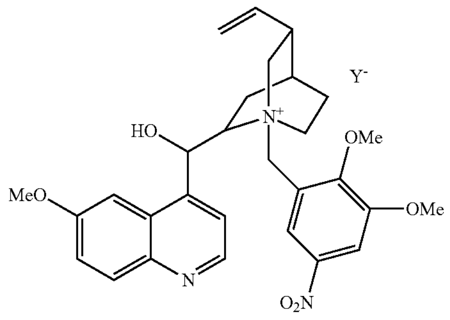

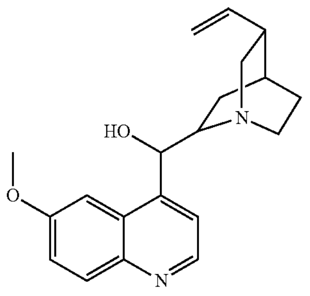

-continued
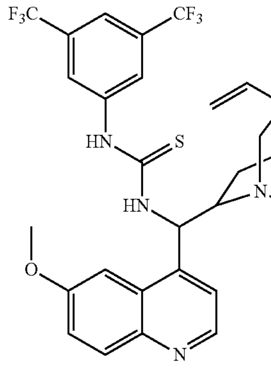
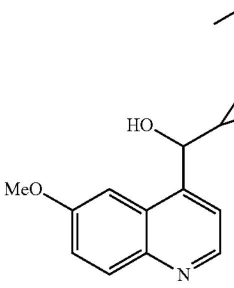
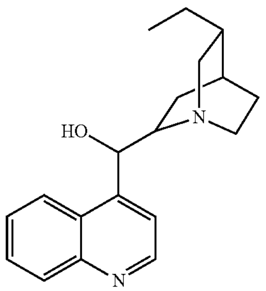
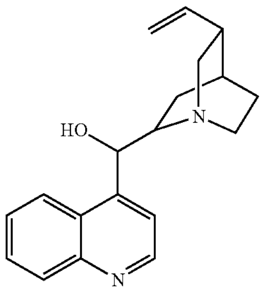
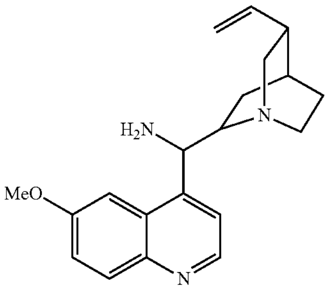
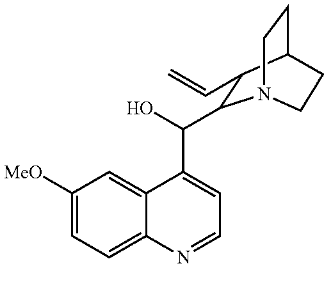
-continued
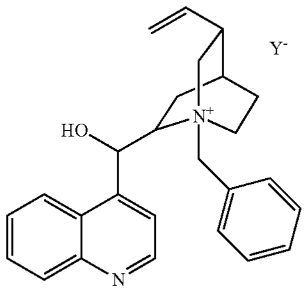
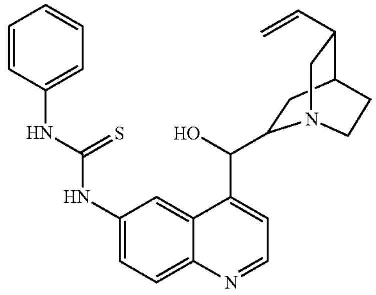
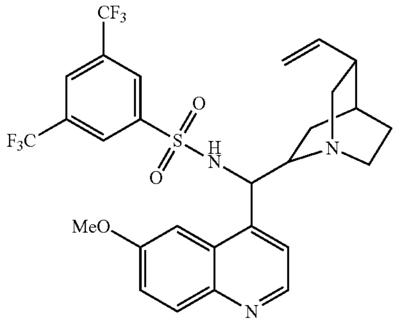
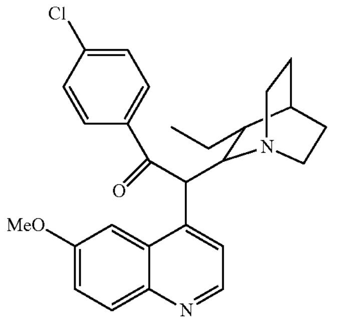
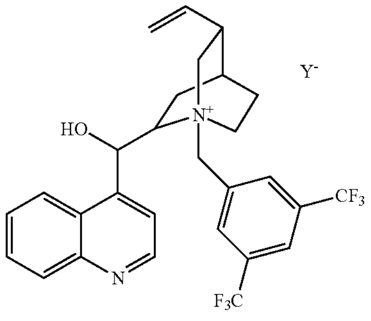

-continued
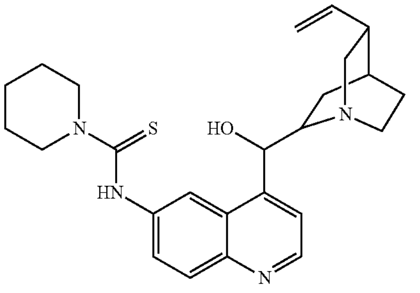
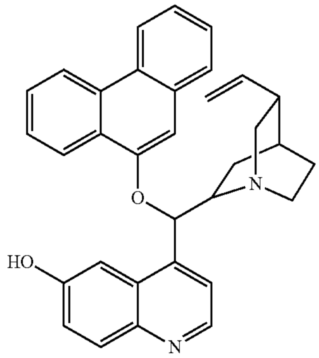
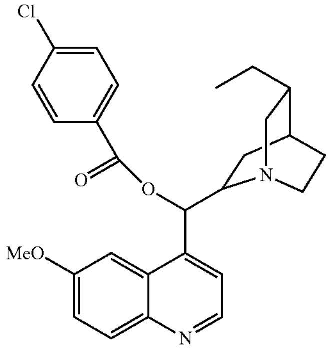
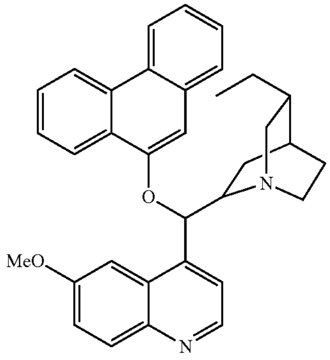
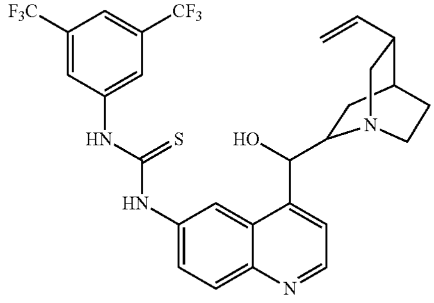
-continued
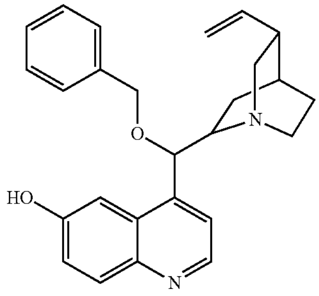
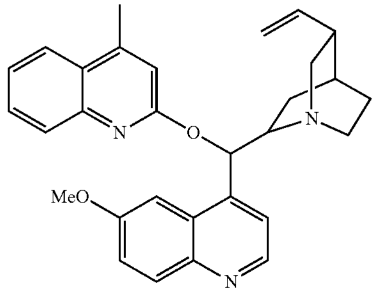
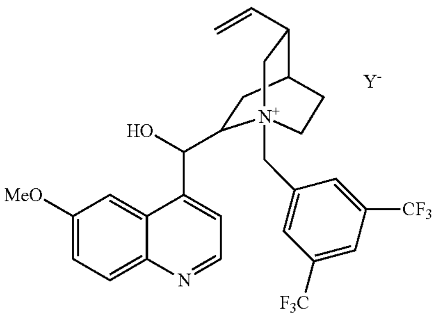
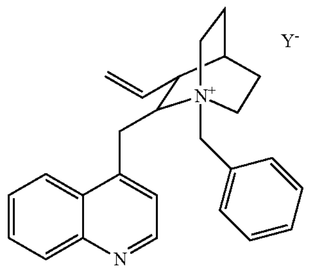
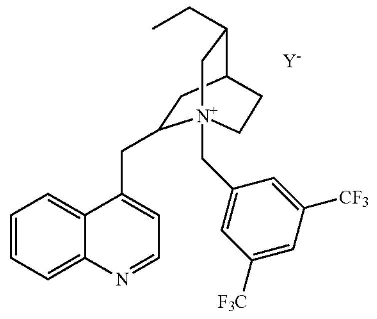

-continued
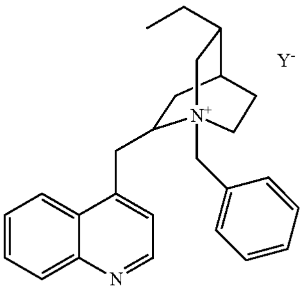
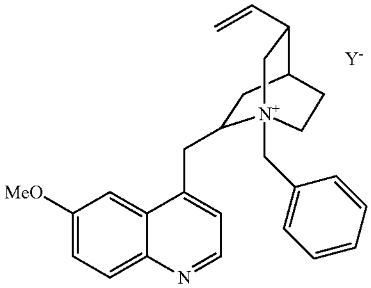
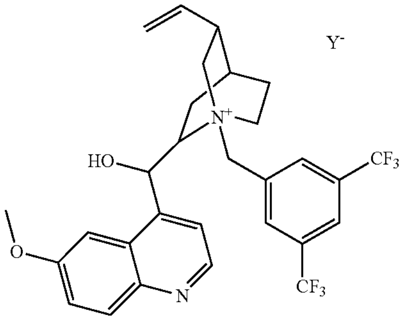
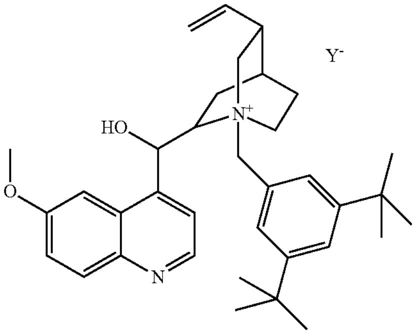
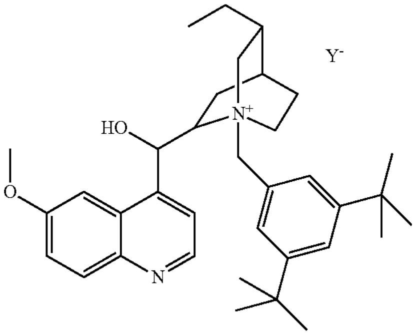
-continued
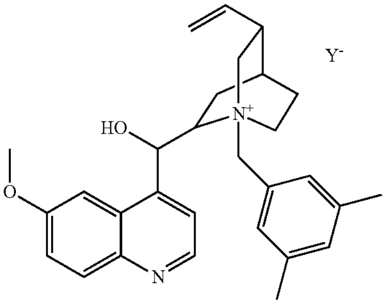
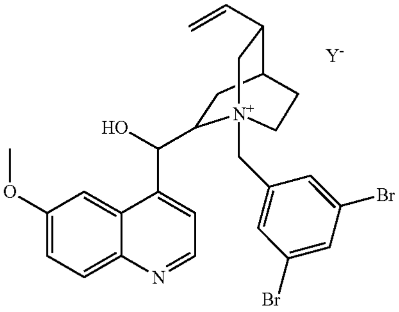
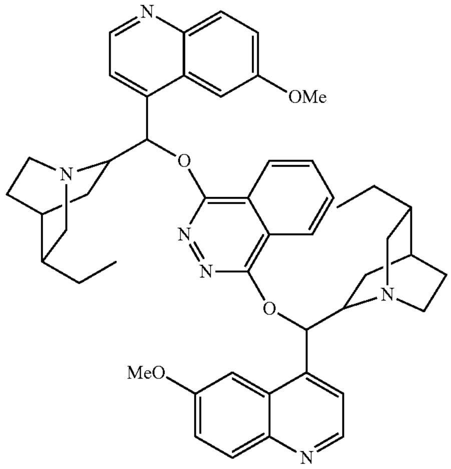
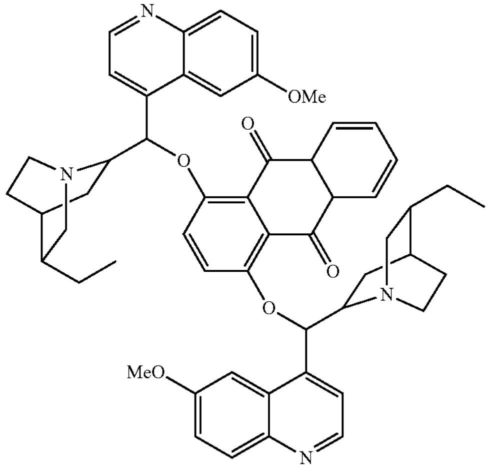

-continued

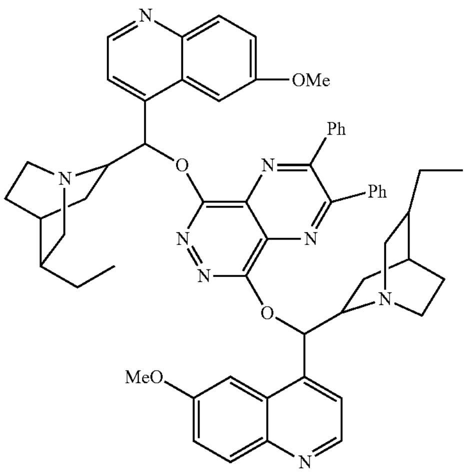

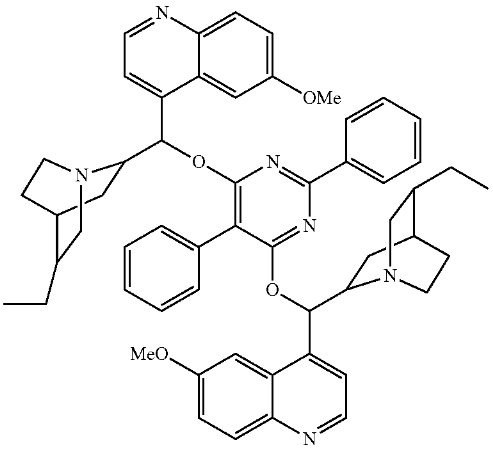

-continued

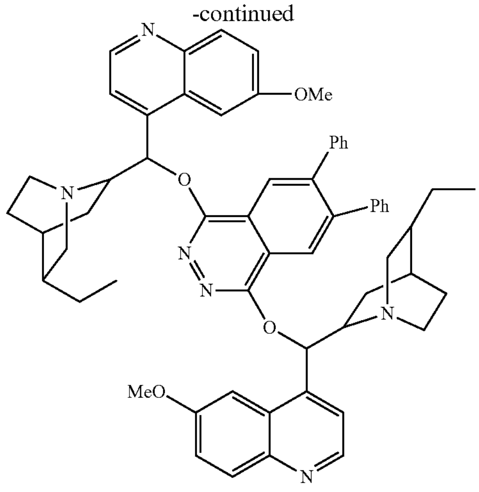

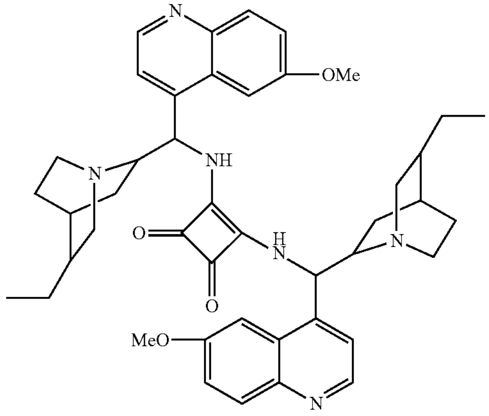

wherein $Y^-$ is a counterion.

14. The process according to claim 1 wherein the catalyst is selected from the group consisting of N-(3,5-ditrifluoromethylbenzyl)quinidinium bromide, N-(3,5-ditertbutylbenzyl)quinidinium bromide, N-(3,5-ditertbutylbenzyl)dihydroquinidinium bromide, N-(3,5-dimethylbenzyl)quinidinium bromide, N-(3,5-dibromobenzyl)quinidinium bromide, N-benzylcinchonidinium bromide, N-(4,5-dimethoxy-2-nitrobenzyl)cinchonidinium bromide, N-(3,5-bis(trifluoromethyl)benzyl)cinchonidinium bromide, N-benzylquinidinium bromide, N-(2-nitro-4,5-dimethoxybenzyl)quinidinium bromide.

15. The process according to claim 1 wherein the step of reacting a compound of formula (IV) with nitromethane in the presence of a catalyst is carried out in the presence of a base.

16. A process according to claim 1 wherein the catalyst is a chiral catalyst.

* * * * *